(12) United States Patent
Yamauchi et al.

(10) Patent No.: US 6,273,887 B1
(45) Date of Patent: Aug. 14, 2001

(54) HIGH-FREQUENCY TREATMENT TOOL

(75) Inventors: Kouji Yamauchi; Naomi Sekino, both of Hachioji; Koji Iida, Sagamihara, all of (JP)

(73) Assignee: Olympus Optical Co., Ltd., Tokyo (JP)

( * ) Notice: Subject to any disclaimer, the term of this patent is extended or adjusted under 35 U.S.C. 154(b) by 0 days.

(21) Appl. No.: 09/234,161

(22) Filed: Jan. 21, 1999

(30) Foreign Application Priority Data

| | | | |
|---|---|---|---|
| Jan. 23, 1998 | (JP) | ................................................. | 10-011199 |
| Aug. 27, 1998 | (JP) | ................................................. | 10-241561 |
| Sep. 2, 1998 | (JP) | ................................................. | 10-248625 |
| Sep. 2, 1998 | (JP) | ................................................. | 10-248673 |
| Oct. 16, 1998 | (JP) | ................................................. | 10-295372 |
| Jan. 21, 1999 | (JP) | ................................................. | 11-012914 |

(51) Int. Cl.$^7$ ................................................. A61B 18/14
(52) U.S. Cl. ................................................. 606/48; 606/51
(58) Field of Search ................................................. 606/51, 52, 45, 606/48, 46, 50

(56) References Cited

U.S. PATENT DOCUMENTS

| | | | | |
|---|---|---|---|---|
| 4,492,231 | * | 1/1985 | Auth ........................................ | 606/51 |
| 5,853,412 | * | 12/1998 | Mayenberger .......................... | 606/51 |
| 5,891,142 | * | 4/1999 | Eggers et al. .......................... | 606/51 |
| 6,024,744 | * | 2/2000 | Kese et al. .............................. | 606/51 |
| 6,187,003 | * | 2/2001 | Buysee et al. .......................... | 606/49 |

FOREIGN PATENT DOCUMENTS

| | | |
|---|---|---|
| 40 32 471 C2 | 4/1992 | (DE) . |
| 41 38 116 A1 | 6/1993 | (DE) . |
| 0 598 348 A1 | 5/1994 | (EP) . |
| 8-317936 | 12/1996 | (JP) . |

* cited by examiner

*Primary Examiner*—Lee Cohen
(74) *Attorney, Agent, or Firm*—Frishauf, Holtz, Goodman, Langer & Chick, P.C.

(57) ABSTRACT

A high-frequency treatment tool includes an insertion portion which can be inserted into a body, a pair of gripping portions arranged at a distal end portion of the insertion portion and having gripping surfaces for gripping vital tissue, a driving mechanism for opening/closing the gripping portions between closing positions where the gripping portions abut against each other and open positions where the gripping portions are separated from each other, electrode portions formed on the gripping surfaces of the gripping portions, to which a high-frequency current is flowed to coagulate/incise the vital tissue gripped by the gripping portions, and a short circuit prevention portion for preventing a short circuit between the electrode portions of the gripping portions when the gripping portions are placed at least at the closing positions.

10 Claims, 40 Drawing Sheets

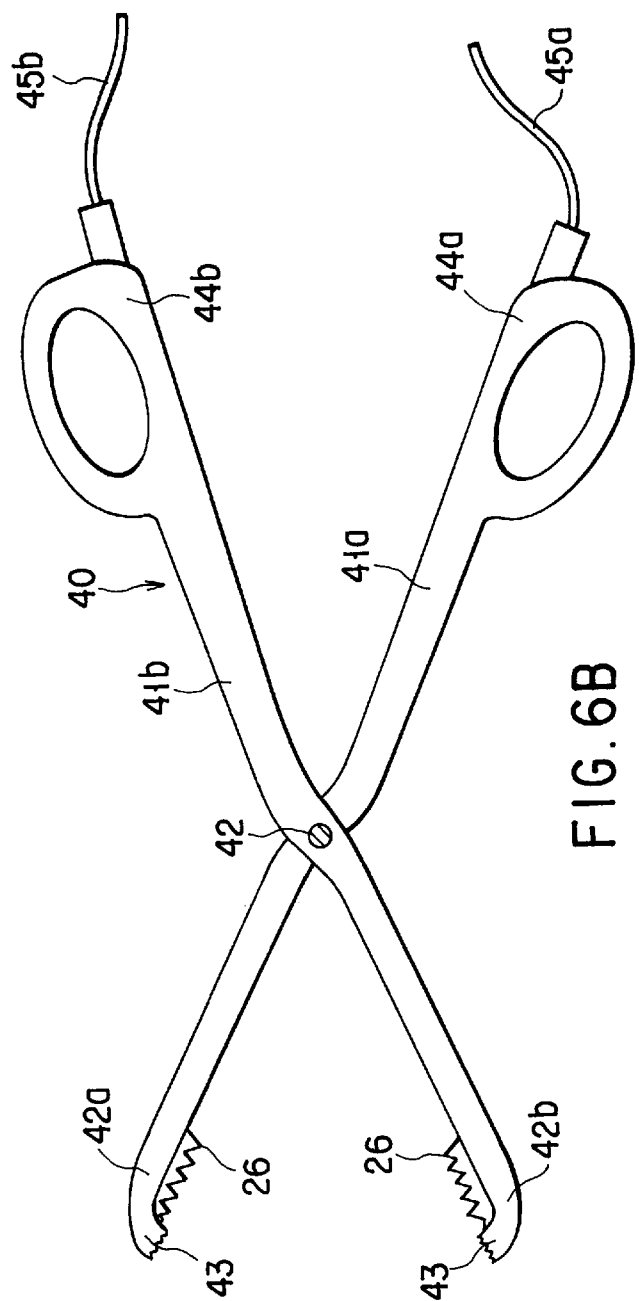
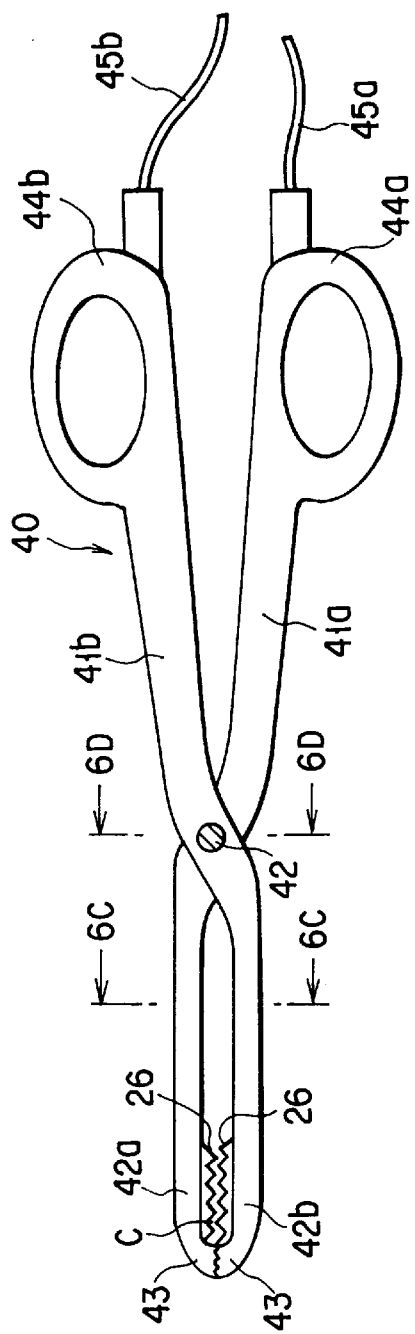
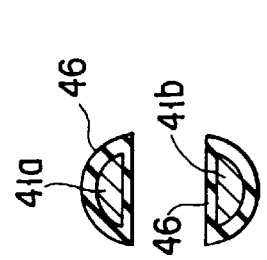
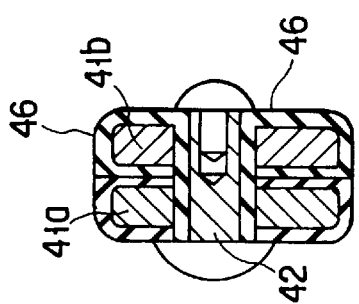

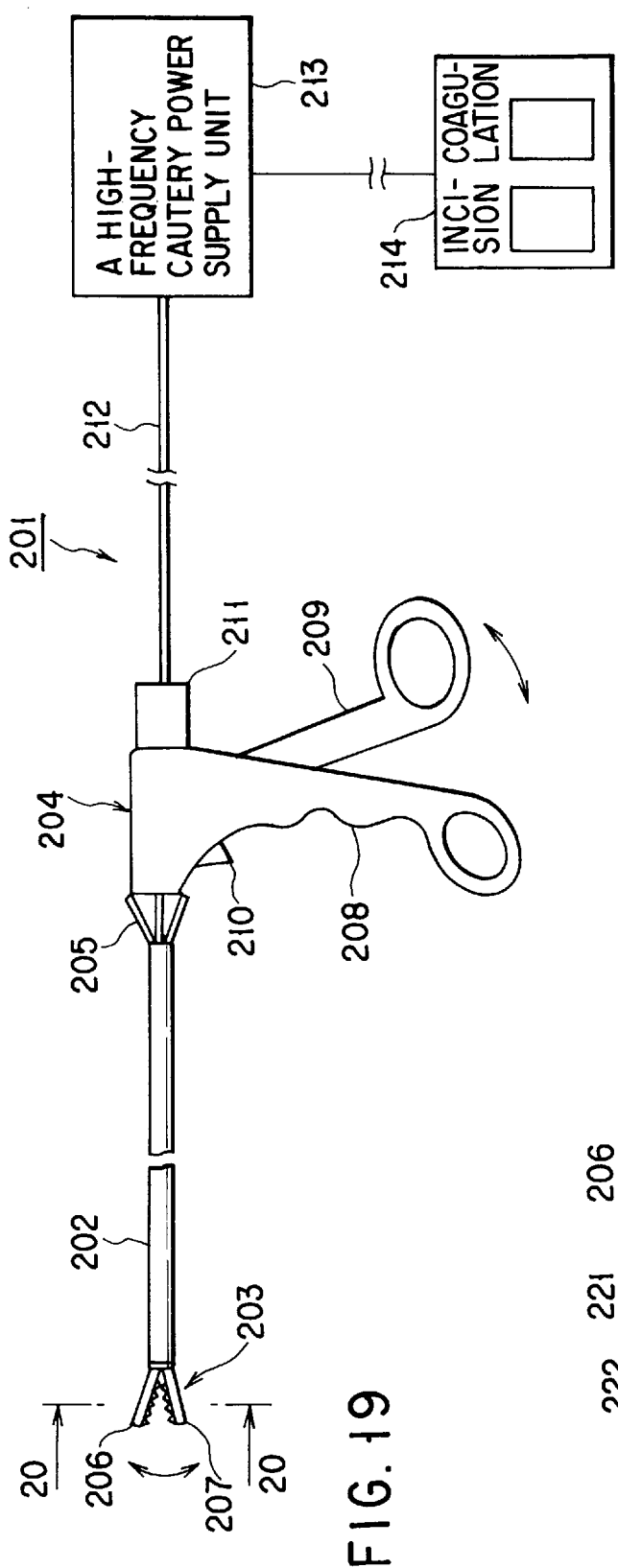
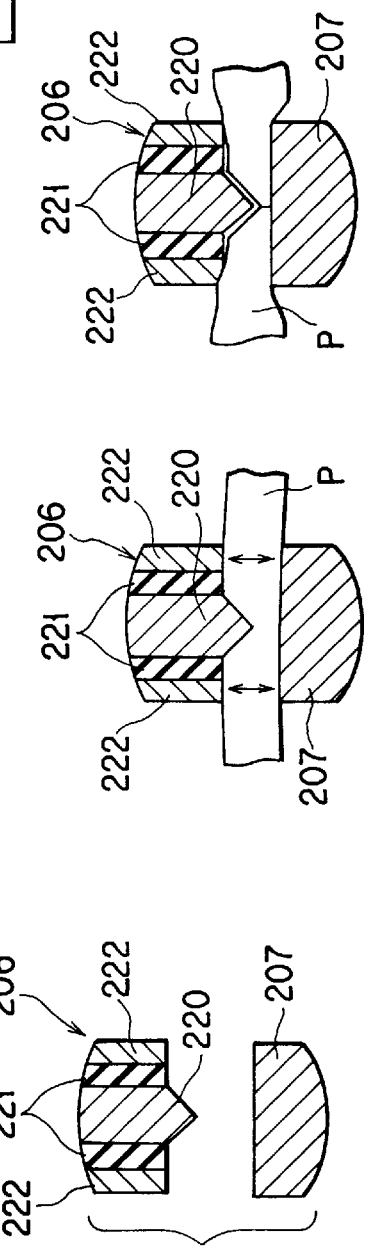
FIG. 19
FIG. 20
FIG. 21A
FIG. 21B

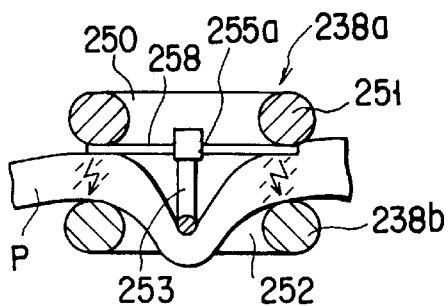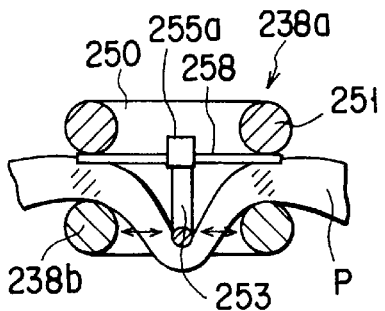
FIG. 34A  FIG. 34B
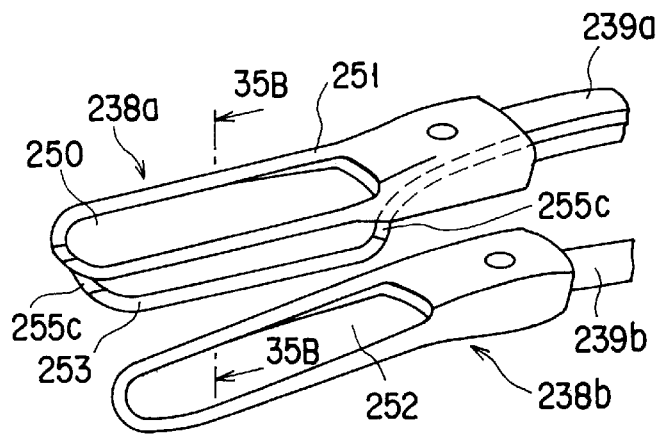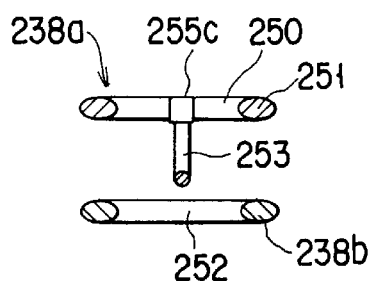
FIG. 35A  FIG. 35B
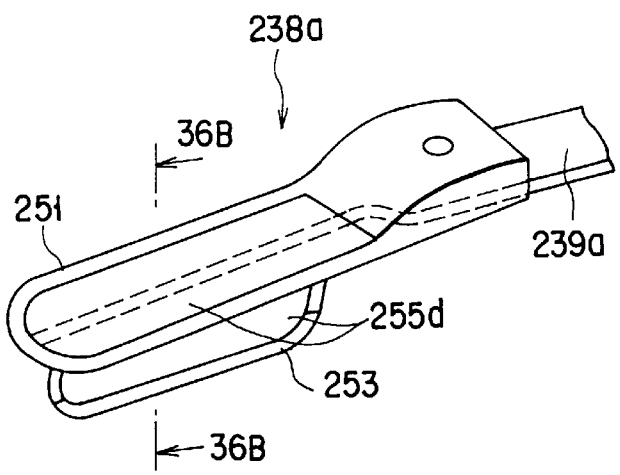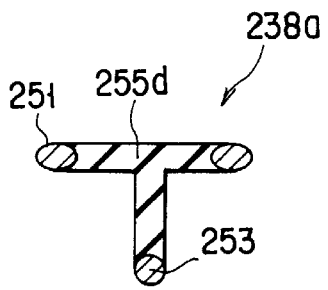
FIG. 36A  FIG. 36B

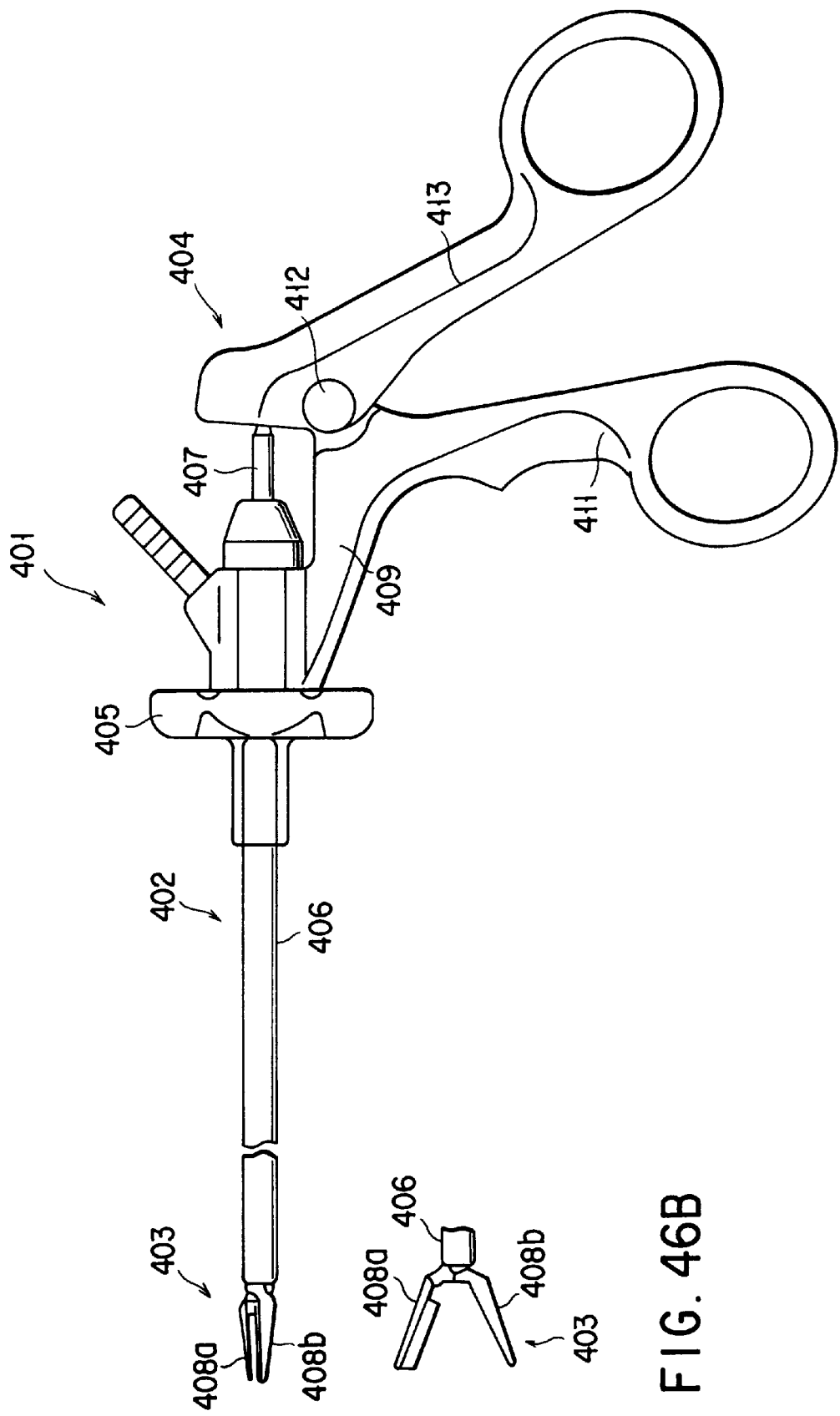

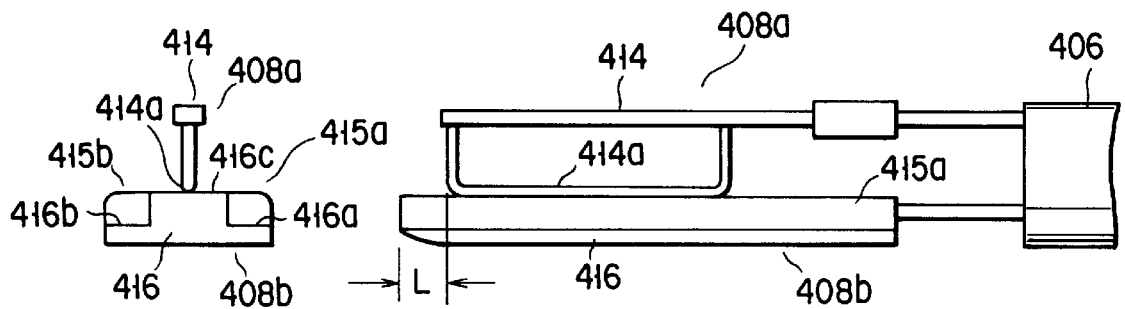
FIG. 47C
FIG. 47A
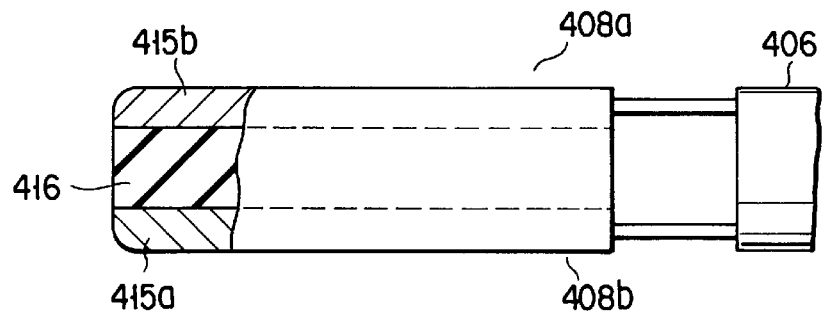
FIG. 47B
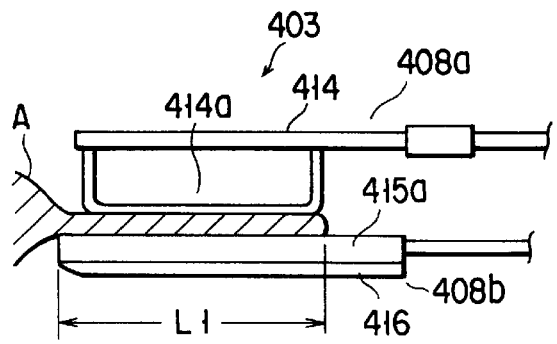
FIG. 48A
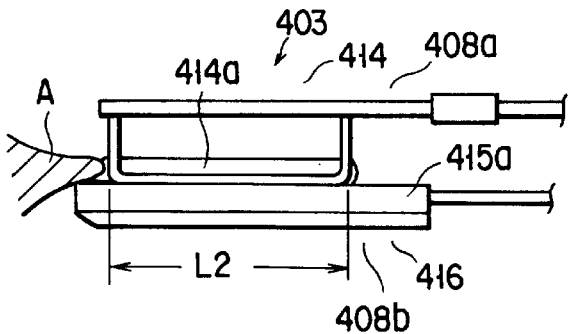
FIG. 48B

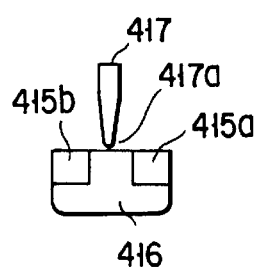
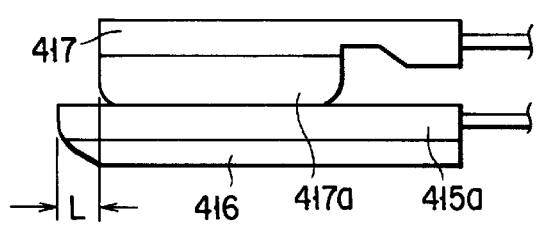
FIG. 49B          FIG. 49A
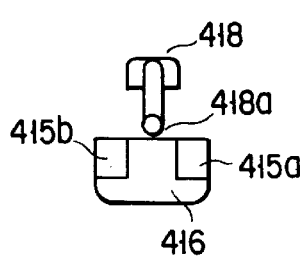
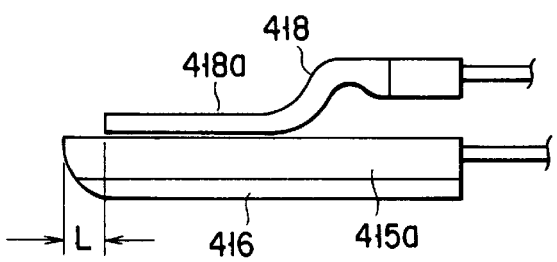
FIG. 50B          FIG. 50A
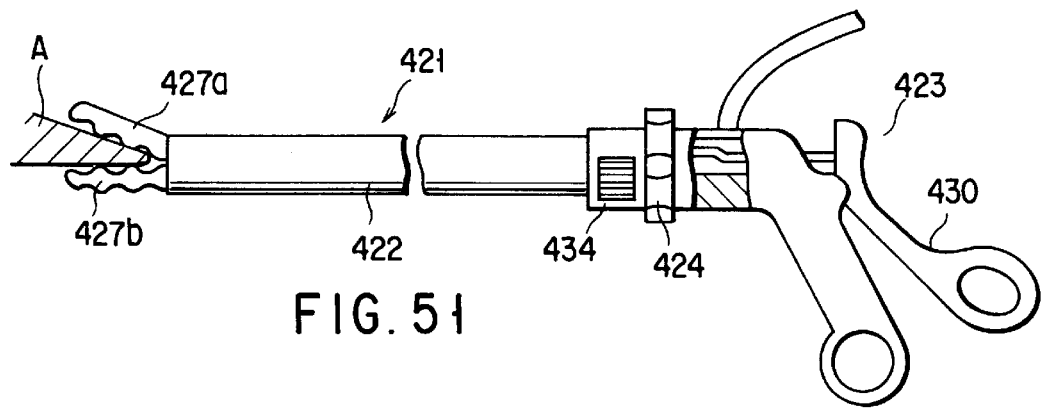
FIG. 51
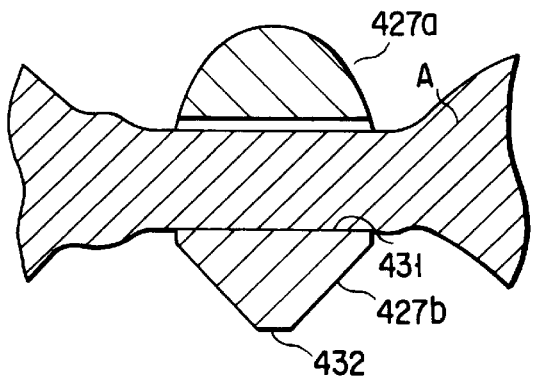
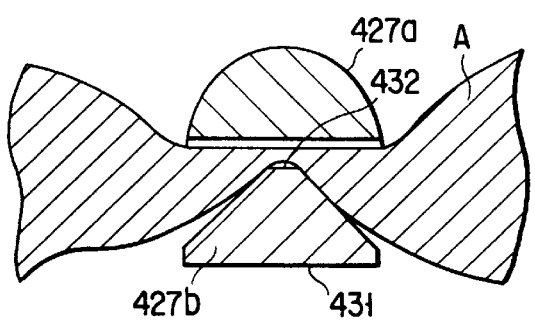
FIG. 52A          FIG. 52B

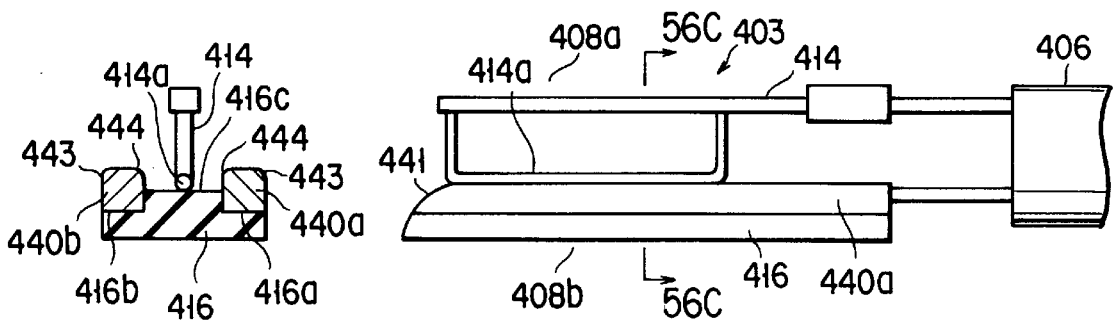
FIG. 56C  FIG. 56A
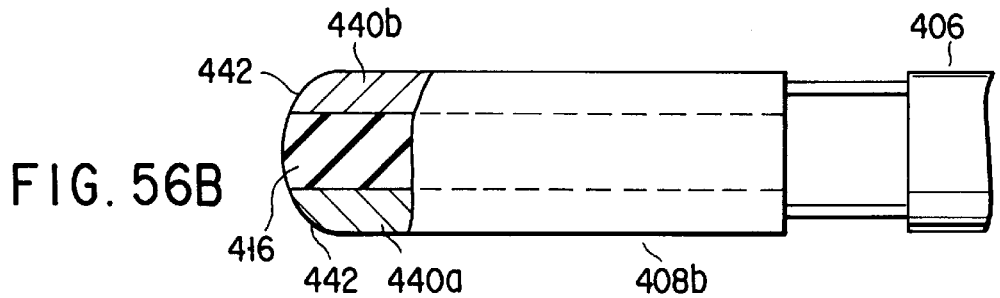
FIG. 56B
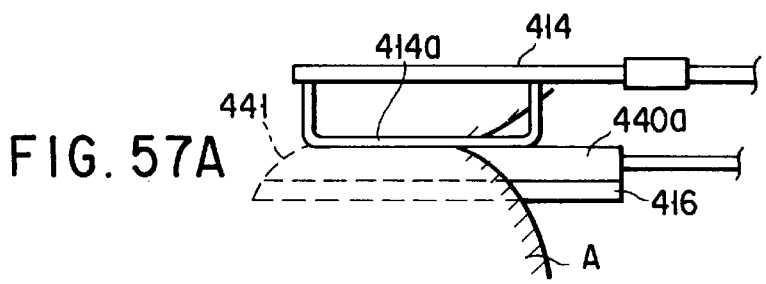
FIG. 57A
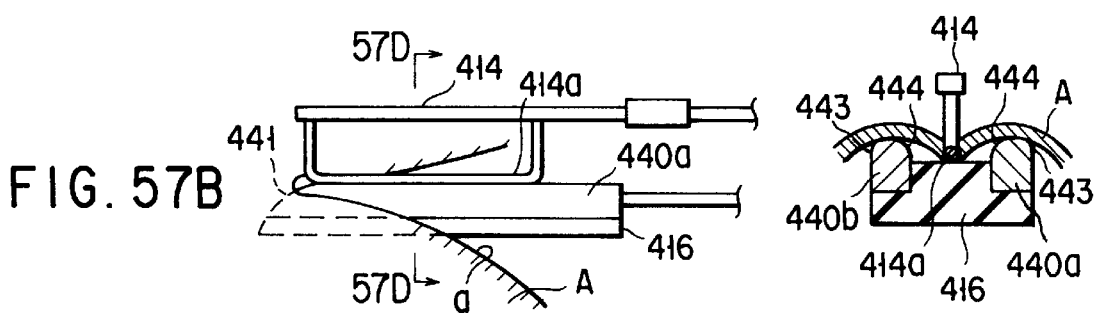
FIG. 57B
FIG. 57D
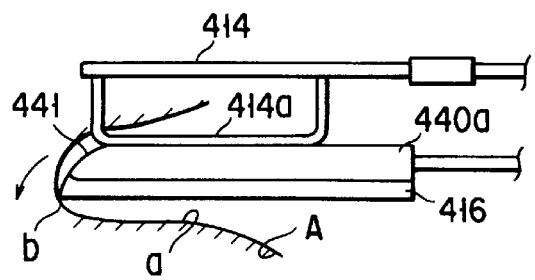
FIG. 57C

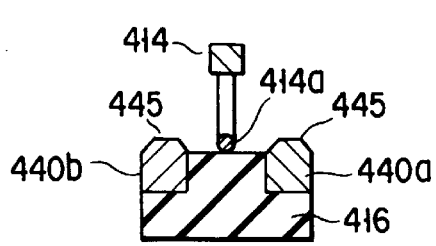
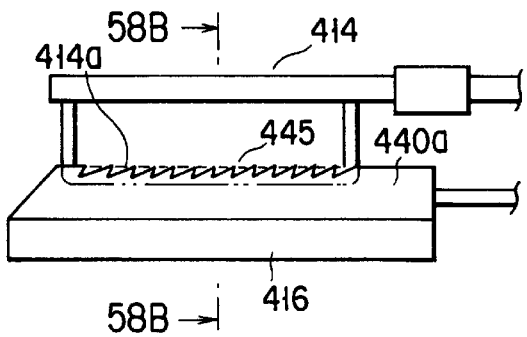
FIG. 58B
FIG. 58A
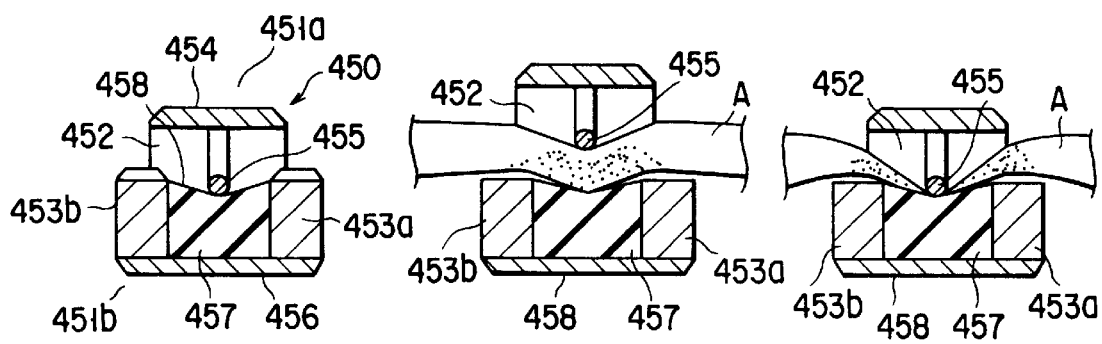
FIG. 59
FIG. 60A
FIG. 60B
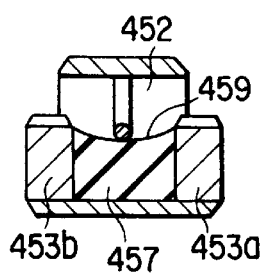
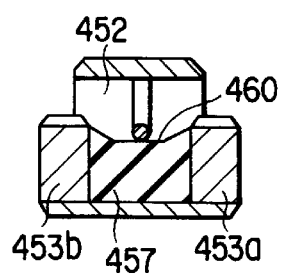
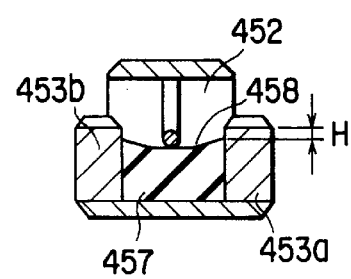
FIG. 61A
FIG. 61B
FIG. 61C
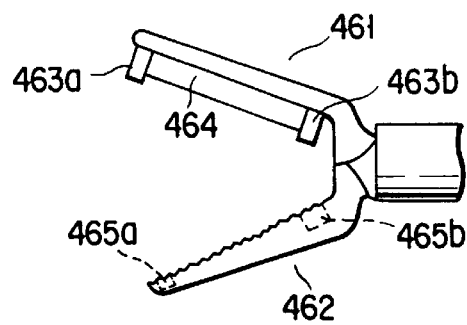
FIG. 62

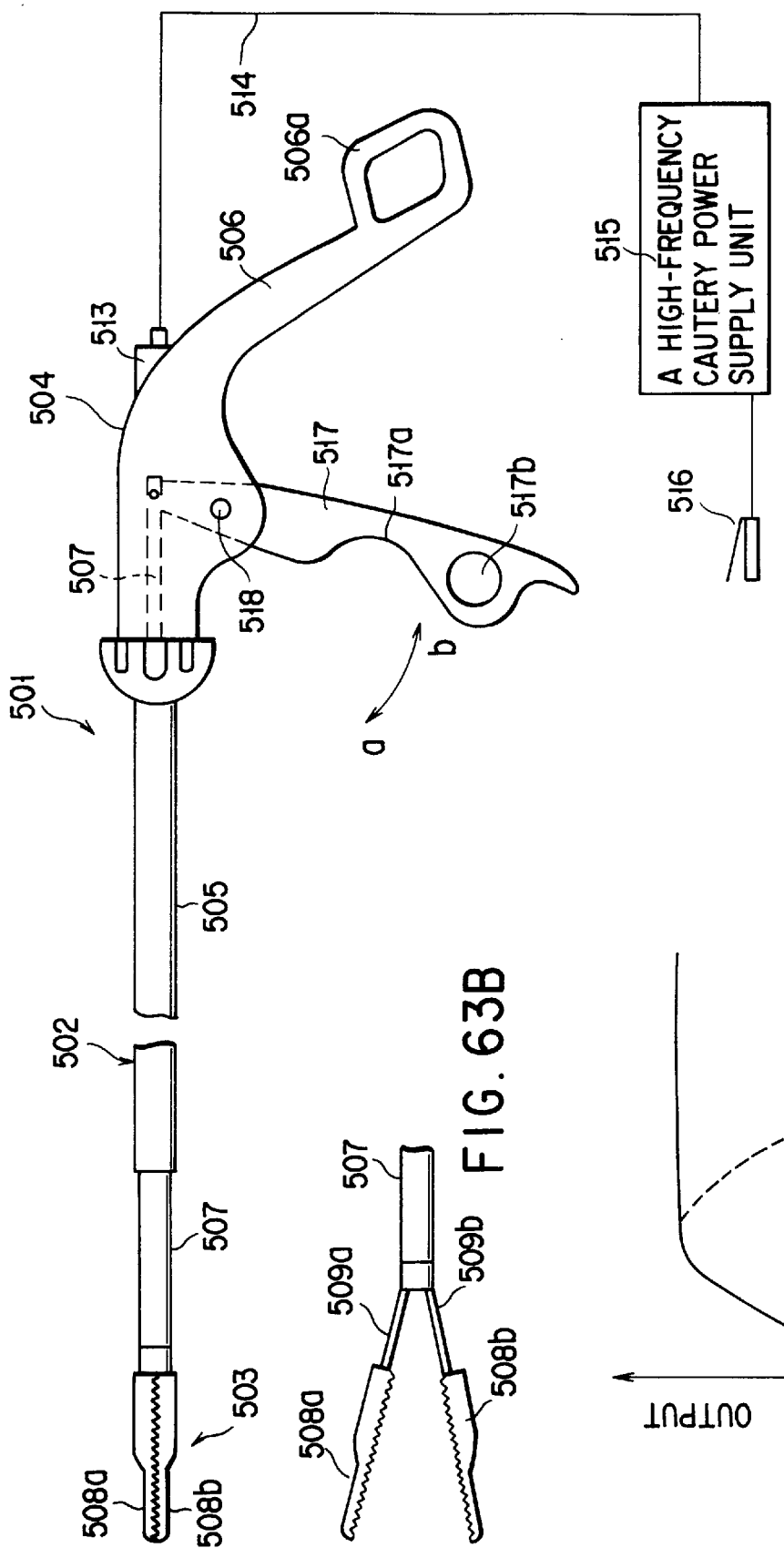

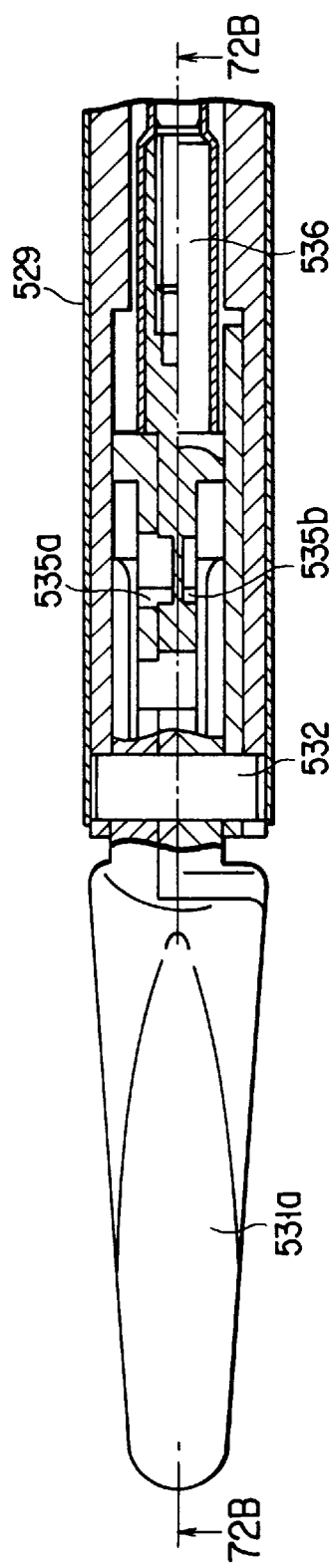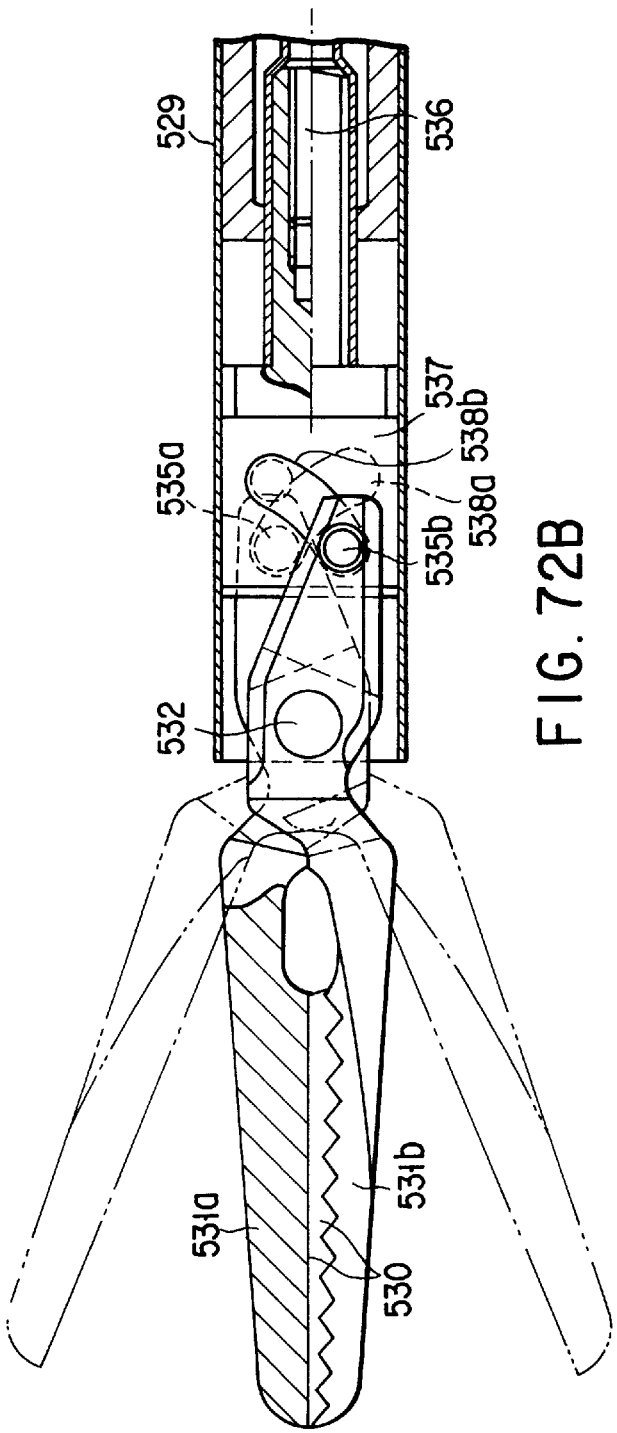
FIG. 72A
FIG. 72B

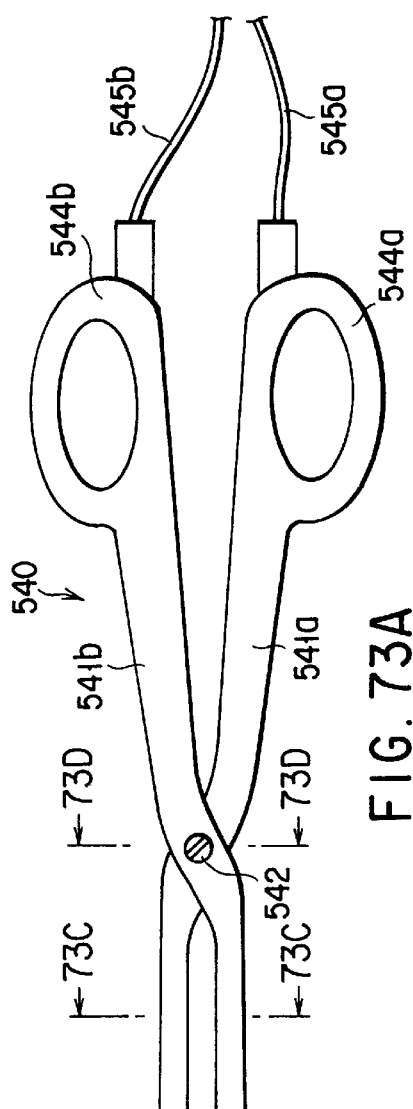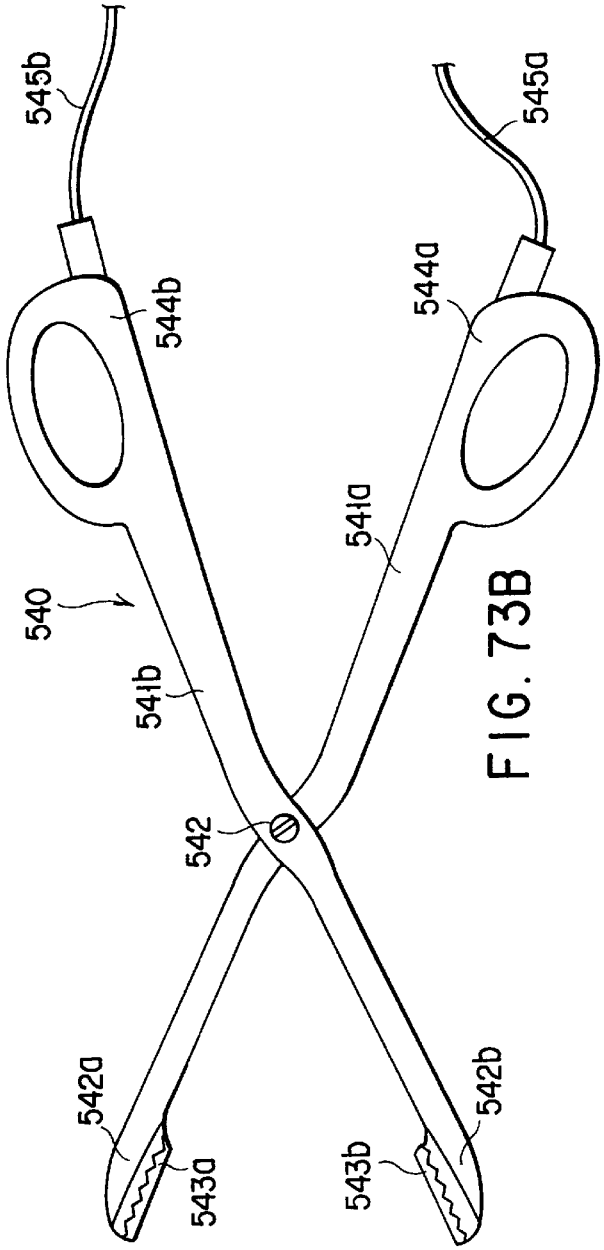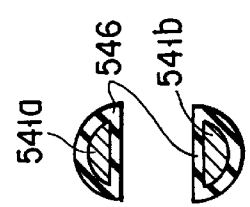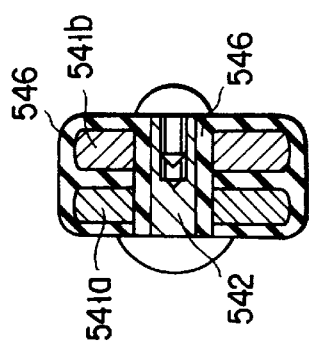

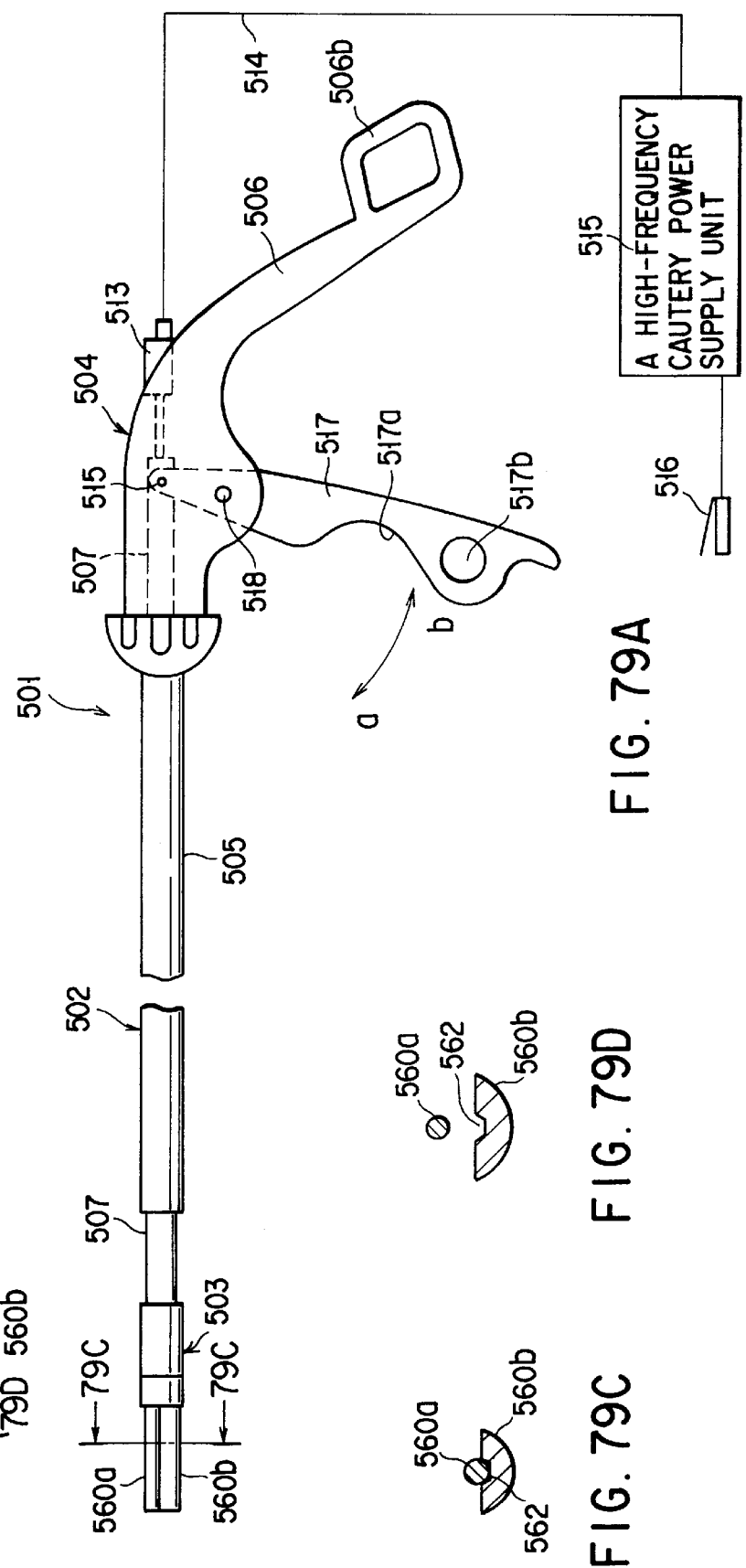

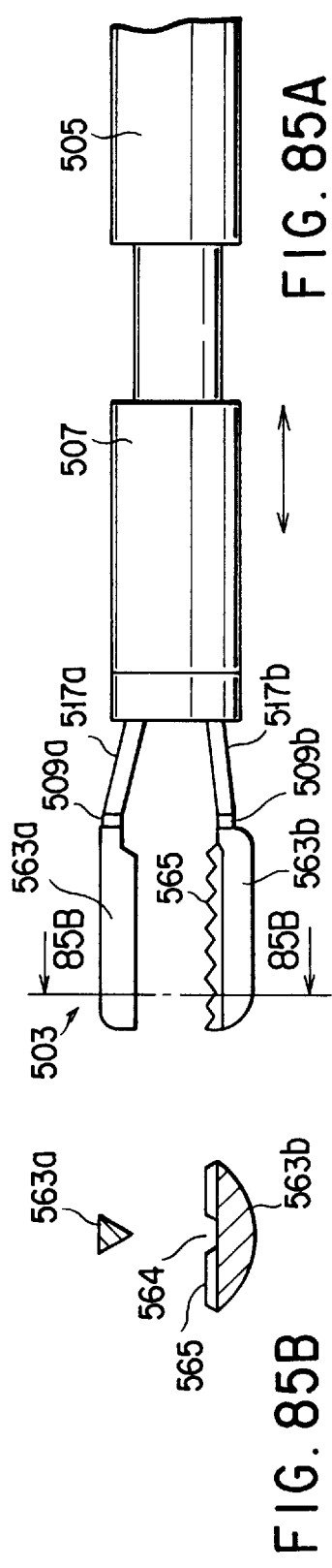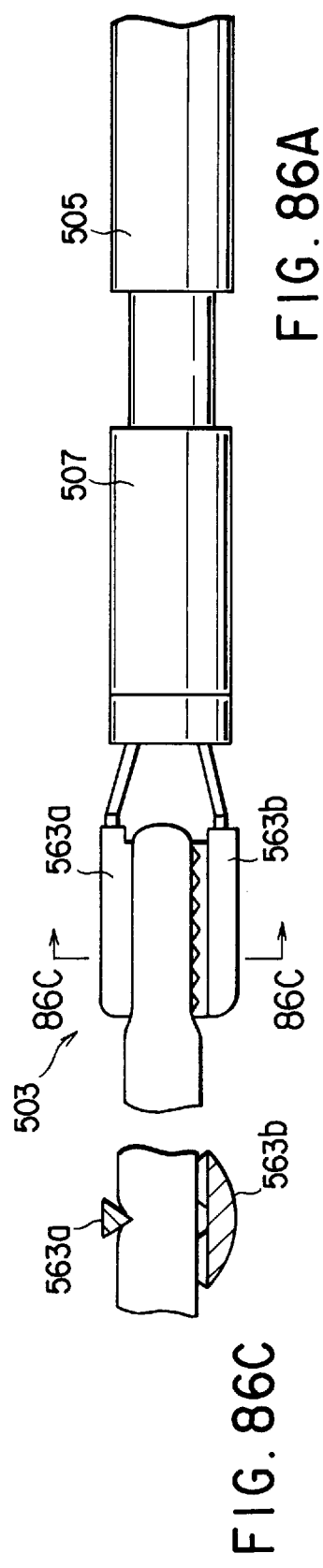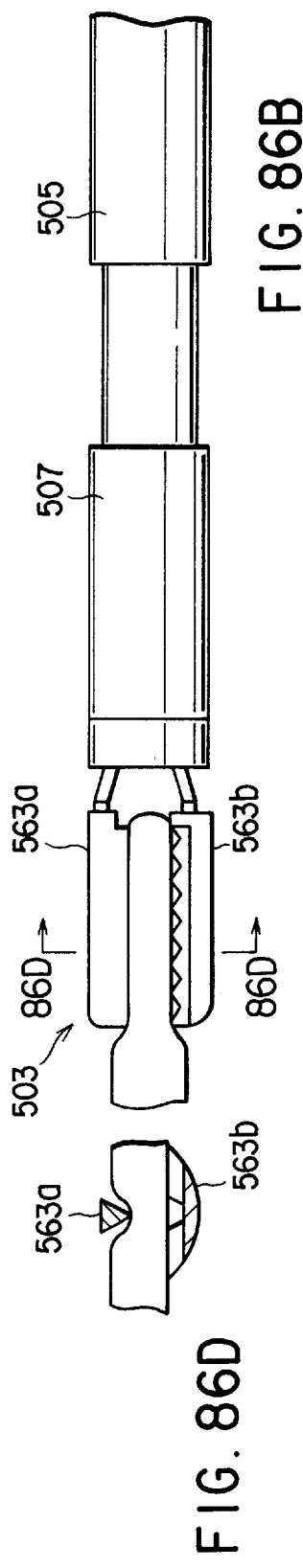

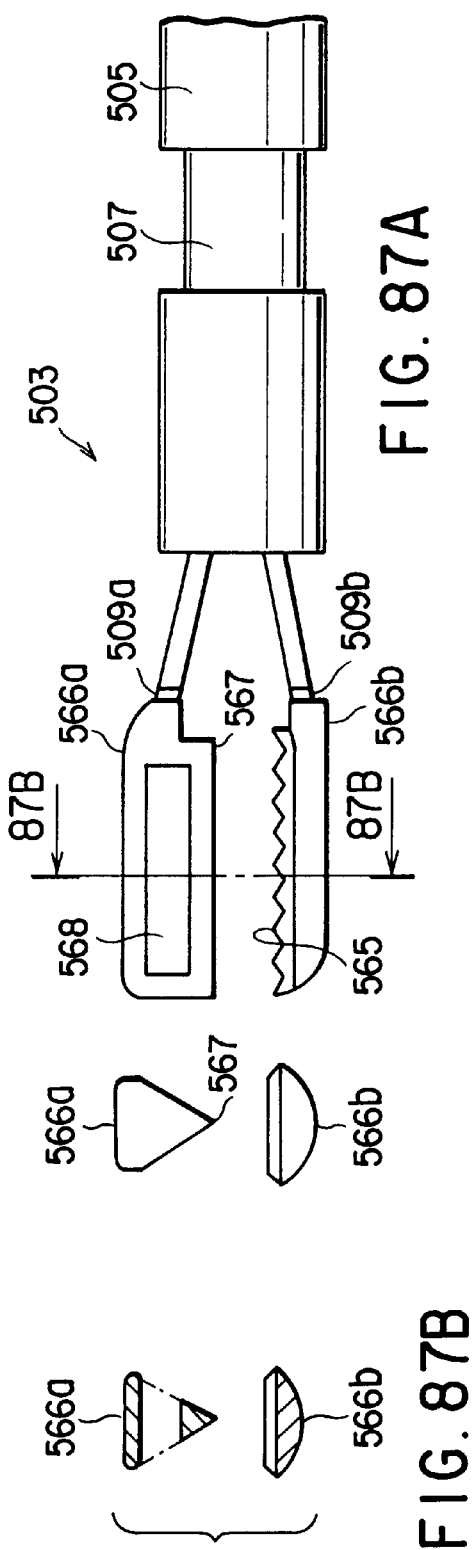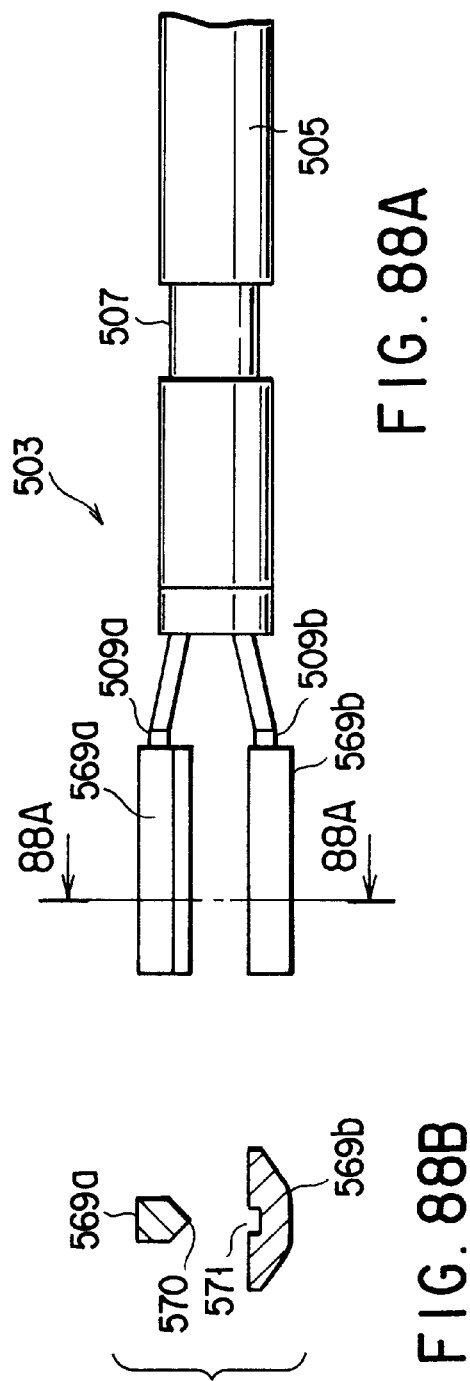

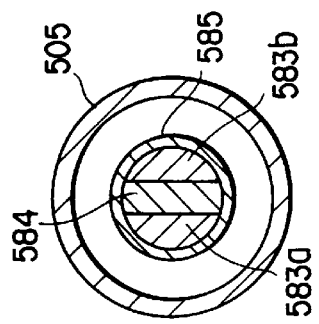
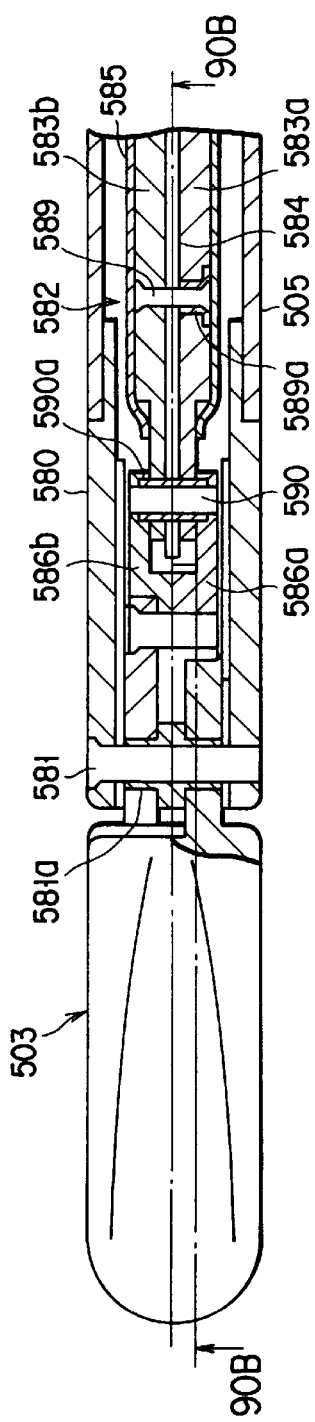
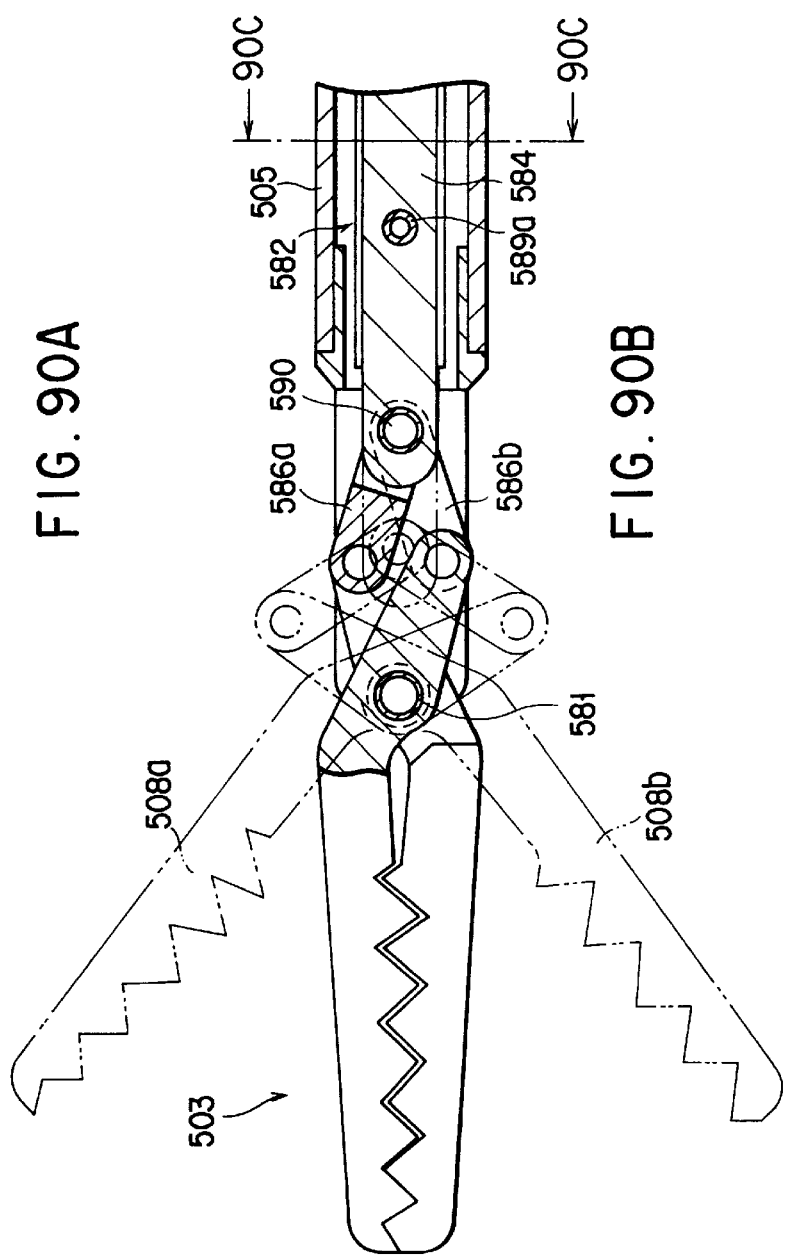

HIGH-FREQUENCY TREATMENT TOOL

BACKGROUND OF THE INVENTION

The present invention relates to a high-frequency treatment tool which can be inserted into a body to grip tissue and coagulate/incise it.

Generally, as a high-frequency treatment tool capable of gripping vital tissue and coagulating/incising it, a bipolar forceps having jaws as a pair of gripping members for gripping vital tissue and high-frequency current supply electrodes formed on the jaws is known. In this bipolar forceps, when vital tissue to be treated is gripped between the pair of jaws, and a high-frequency current is provided across the electrodes of the jaws, the vital tissue between the jaws is coagulated or incised.

Bipolar forceps of this type are normally used for various purposes, e.g., to stop bleeding from blood vessels included in vital tissue, cauterize a morbid portion or bleeding point on the surface of vital tissue, or close a uterine tube for contraception, and disclosed in, e.g., Jpn. Pat. Appln. KOKAI Publication No. 8-317936, Ger. Publication DE 4138116 A1, Ger. Publication DE 4032471 C2, or EP 0598348 A1.

In the conventional bipolar forceps, especially, when thin membranous tissue is gripped by the jaws, the metal portions of the jaws may come into contact with each other to flow a high-frequency current across the metal portions in contact. That is, the jaws electrically short-circuit. In this case, the high-frequency current does not flow to the tissue gripped between the jaws, so the tissue cannot be reliably coagulated or incised. In addition, if complete coagulation cannot be performed, bleeding may occur during the subsequent incision.

In the bipolar forceps disclosed DE 4138116 A1 or DE 4032471 C2, tissue is gripped by three rod electrodes. For this reason, the tissue escapes upon gripping and cannot be reliably gripped. Hence, coagulation/incision cannot be satisfactorily performed.

In the bipolar forceps disclosed in DE 4032471 C2 (FIG. 2) or DE 4138116 A1 (FIGS. 5 and 6), the far ends of the coagulation and incision electrodes are at the same position to incise the entire coagulation region. This may cause bleeding. In addition, a bipolar high-frequency incision tool disclosed in EP 059348 A1 incises the entire gripped region.

BRIEF SUMMARY OF THE INVENTION

It is the first object of the present invention to provide a high-frequency treatment tool capable of preventing an electrical short circuit between a pair of gripping members and reliably coagulating/incising tissue. It is the second object of the present invention to provide a high-frequency treatment tool capable of reliably gripping tissue to coagulate/incise it. It is the third object of the present invention to provide a high-frequency treatment tool capable of incising only coagulated tissue and preventing bleeding.

The objects of the present invention are achieved by the following high-frequency treatment tool. A high-frequency treatment tool according to the present invention comprises an insertion portion which can be inserted into a body; a pair of gripping portions arranged at a distal end portion of the insertion portion and having gripping surfaces for gripping vital tissue; a driving mechanism for opening/closing the gripping portions between closing positions where the gripping portions abut against each other and open positions where the gripping portions are separated from each other; electrode portions formed on the gripping surfaces of the gripping portions, to which a high-frequency current is flowed to coagulate/incise the vital tissue gripped by the gripping portions; and short circuit prevention means for preventing a short circuit between the electrode portions of the gripping portions when the gripping portions are placed at least at the closing positions.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 6A is a side view of a high-frequency treatment tool according to the fifth embodiment of the present invention in the closed state;

FIG. 6B is a side view of the high-frequency treatment tool shown in FIG. 6A in the open state;

FIG. 6C is a sectional view taken along a line 6C—6C in FIG. 6A;

FIG. 6D is a sectional view taken along a line 6D—6D in FIG. 6A;

FIG. 19 is a side view of a high-frequency treatment tool according to the 12th embodiment of the present invention;

FIG. 20 is a sectional view taken along a line 20—20 in FIG. 19;

FIGS. 21A and 21B are sectional views showing a use form of the high-frequency treatment tool shown in FIG. 19;

FIGS. 34A and 34B are sectional views showing a use form of the high-frequency treatment tool shown in FIG. 31A;

FIG. 35A is a perspective view showing the first modification of the treatment portion of the high-frequency treatment tool shown in FIG. 31A;

FIG. 35B is a sectional view taken along a line 35B—35B in FIG. 35A;

FIG. 36A is a perspective view showing the second modification of the treatment portion of the high-frequency treatment tool shown in FIG. 31A;

FIG. 36B is a sectional view taken along a line 36B—36B in FIG. 36A;

FIG. 46A is a view showing the overall arrangement of a high-frequency treatment tool according to the 18th embodiment of the present invention;

FIG. 46B is a side view of the treatment portion of the high-frequency treatment tool shown in FIG. 46A in the open state;

FIG. 47A is a side view of the treatment portion of the high-frequency treatment tool shown in FIG. 46A;

FIG. 47B is a plan view of the treatment portion of the high-frequency treatment tool shown in FIG. 46A;

FIG. 47C is a front view of the treatment portion of the high-frequency treatment tool shown in FIG. 46A;

FIGS. 48A and 48B are views showing a use form of the high-frequency treatment tool shown in FIG. 46A;

FIG. 49A is a side view of the treatment portion of a high-frequency treatment tool according to the 19th embodiment of the present invention;

FIG. 49B is a front view of the treatment portion shown in FIG. 49A;

FIG. 50A is a side view of the treatment portion of a high-frequency treatment tool according to the 20th embodiment of the present invention;

FIG. 50B is a front view of the treatment portion shown in FIG. 50A;

FIG. 51 is a view showing the overall arrangement of a high-frequency treatment tool according to the 21st embodiment of the present invention;

FIG. 52A is a sectional view of tissue coagulated by the high-frequency treatment tool shown in FIG. 51;

FIG. 52B is a sectional view of tissue incised by the high-frequency treatment tool shown in FIG. 51;

FIG. 56A is a side view of the treatment portion of a high-frequency treatment tool according to the 23rd embodiment of the present invention;

FIG. 56B is a plan view of a treatment portion shown in FIG. 56A;

FIG. 56C is a sectional view taken along a line 56C—56C in FIG. 56A;

FIGS. 57A to 57C are views showing a use form of the high-frequency treatment tool shown in FIG. 56A;

FIG. 57D is a sectional view taken along a line 57D—57D in FIG. 57B;

FIG. 58A is a side view of a treatment portion of a high-frequency treatment tool according to the 24th embodiment of the present invention;

FIG. 58B is a sectional view taken along a line 58B—58B in FIG. 58A;

FIG. 59 is a sectional view of the treatment portion of a high-frequency treatment tool according to the 25th embodiment of the present invention;

FIGS. 60A and 60B are sectional views showing a use form of the high-frequency treatment tool shown in FIG. 59;

FIGS. 61A to 61C are sectional views showing a modification of the 25th embodiment;

FIG. 62 is a view showing a disclosure example of the treatment portion;

FIG. 63A is a side view showing the overall arrangement of a high-frequency treatment tool according to the 26th embodiment of the present invention;

FIG. 63B is a side view of the treatment portion of the high-frequency treatment tool shown in FIG. 63A in the open state;

FIG. 63C is a graph showing the relationship between the output and the impedance;

FIG. 72A is a partially longitudinally cutaway plan view of the distal end portion of a high-frequency treatment tool according to the 34th embodiment of the present invention;

FIG. 72B is a sectional view taken along a line 72B—72B in FIG. 72A;

FIG. 73A is a side view of a high-frequency treatment tool according to the 35th embodiment of the present invention in the closed state;

FIG. 73B is a side view of the high-frequency treatment tool shown in FIG. 73A in the open state;

FIG. 73C is a sectional view taken along a line 73C—73C in FIG. 73A;

FIG. 73D is a sectional view taken along a line 73D—73D in FIG. 73A;

FIG. 78A is a perspective view of the treatment portion of a high-frequency treatment tool according to the 40th embodiment of the present invention;

FIG. 78B is a sectional view showing a state wherein tissue is coagulated/incised by the high-frequency treatment tool shown in FIG. 78A;

FIG. 78C is a sectional view of tissue incised by the high-frequency treatment tool shown in FIG. 78A;

FIG. 79A is a side view of a high-frequency treatment tool according to the 41st embodiment of the present invention;

FIG. 79B is a side view of the high-frequency treatment tool shown in FIG. 79A in the open state;

FIG. 79C is a sectional view taken along a line 79C—79C in FIG. 79A;

FIG. 79D is a sectional view taken along a line 79D—79D in FIG. 79B;

FIG. 80A is a side view of the distal end side of the high-frequency treatment tool shown in FIG. 79A;

FIG. 80B is a sectional view taken along a line 80B—80B in FIG. 80A;

FIG. 81A is a sectional view of tissue coagulated by the high-frequency treatment tool shown in FIG. 79A;

FIG. 81B is a sectional view of tissue incised by the high-frequency treatment tool shown in FIG. 79A;

FIG. 82A is a graph showing the relationship between the output and the impedance upon coagulation;

Figure 82A:
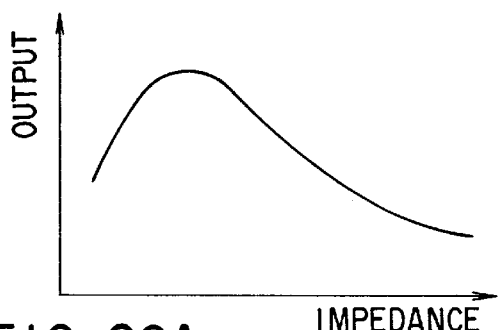
Figure 82B:
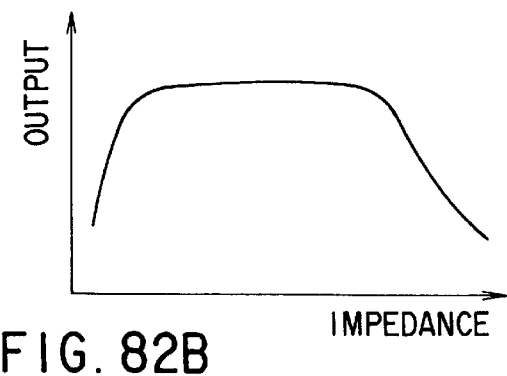
Figure 82C:
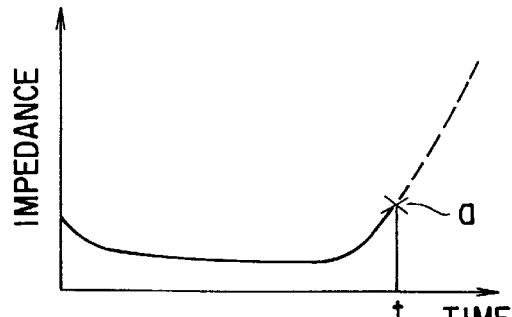
Figure 83A:
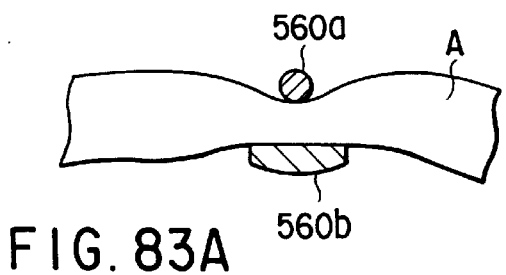
Figure 83B:
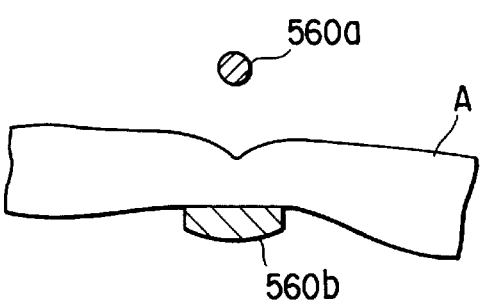
Figure 83C:
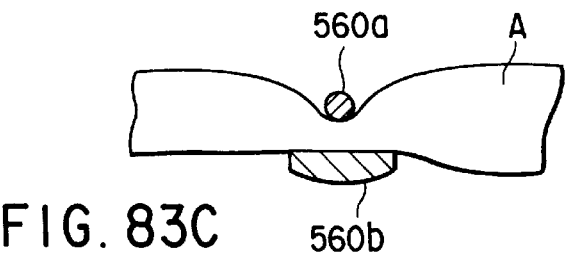
Figure 84A:
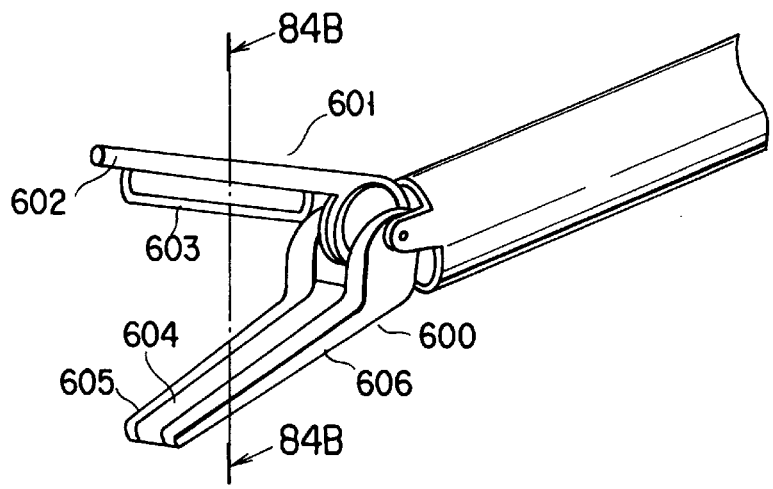
Figure 84B:
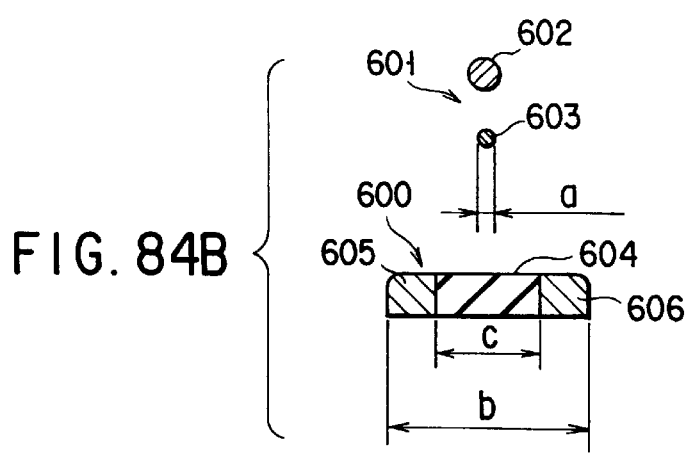
Figure 89A:
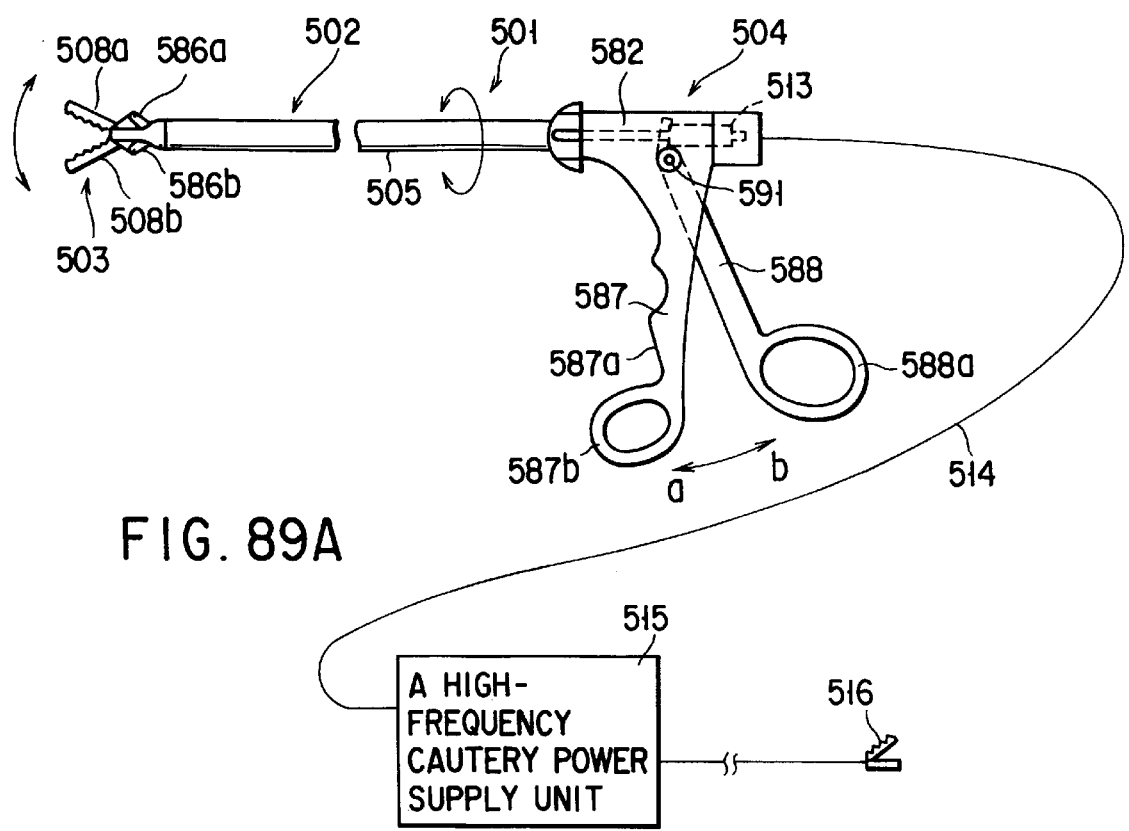
Figure 89B:
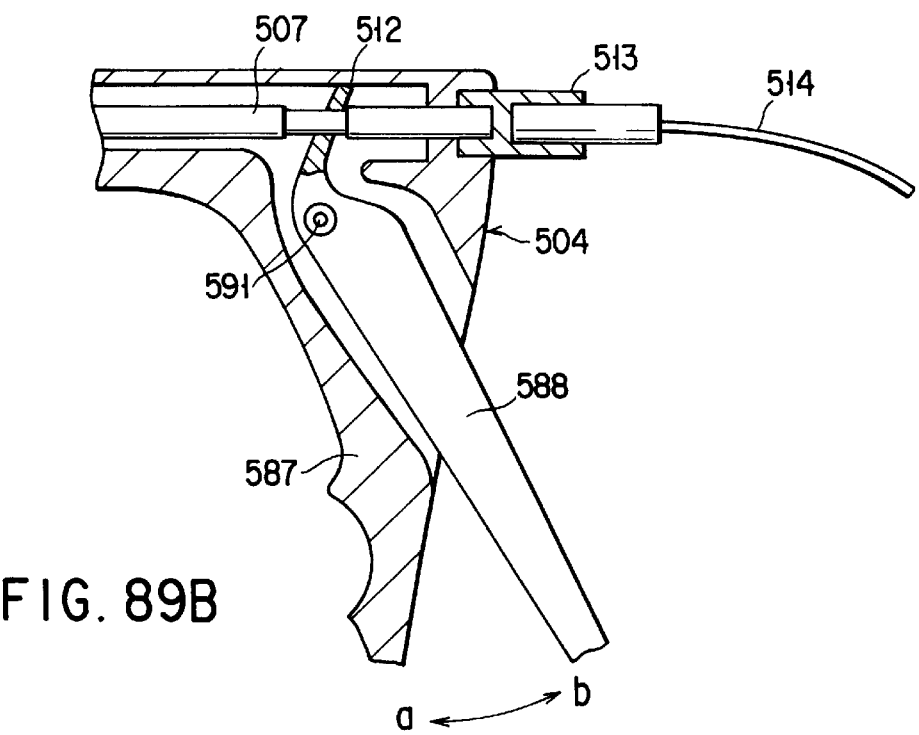

FIG. 82B is a graph showing the relationship between the output and the impedance upon incision;

FIG. 82C is a graph showing a change in impedance by power supply upon coagulation;

FIGS. 83A to 83C are sectional views showing a use form of a high-frequency treatment tool according to the first modification of the 41st embodiment;

FIG. 84A is a perspective view of the distal end side of a high-frequency treatment tool according to the second modification of the 41st embodiment;

FIG. 84B is a sectional view taken along a line 84B—84B in FIG. 84A;

FIG. 85A is a side view of the distal end side of a high-frequency treatment tool according to the 42nd embodiment of the present invention;

FIG. 85B is a sectional view taken along a line 85B—85B in FIG. 85A;

FIGS. 86A and 86B are side views showing a use form of the high-frequency treatment tool shown in FIG. 85A;

FIGS. 86C and 86D are sectional views taken along line 86C—86C in FIG. 86A and line 86D—86D in FIG. 86B;

FIG. 87A is a side view of the distal end side of a high-frequency treatment tool according to the 43rd embodiment of the present invention;

FIG. 87B is a sectional view taken along a line 87B—87B in FIG. 87A;

FIG. 88A is a side view of the distal end side of a high-frequency treatment tool according to the 44th embodiment of the present invention;

FIG. 88B is a sectional view taken along a line 88B—88B in FIG. 88A;

FIG. 89A is a view showing the overall arrangement of a high-frequency treatment tool according to the 45th embodiment of the present invention;

FIG. 89B is a sectional view of an operation portion of the high-frequency treatment tool shown in FIG. 89A;

FIG. 90A is a cross-sectional view of the high-frequency treatment tool shown in FIG. 89A;

FIG. 90B is a sectional view taken along a line 90B—90B in FIG. 90A; and

FIG. 90C is a sectional view taken along a line 90C—90C in FIG. 90B.

DETAILED DESCRIPTION OF THE INVENTION

The embodiments of the present invention will be described below with reference to the accompanying drawing.

Figure 1:
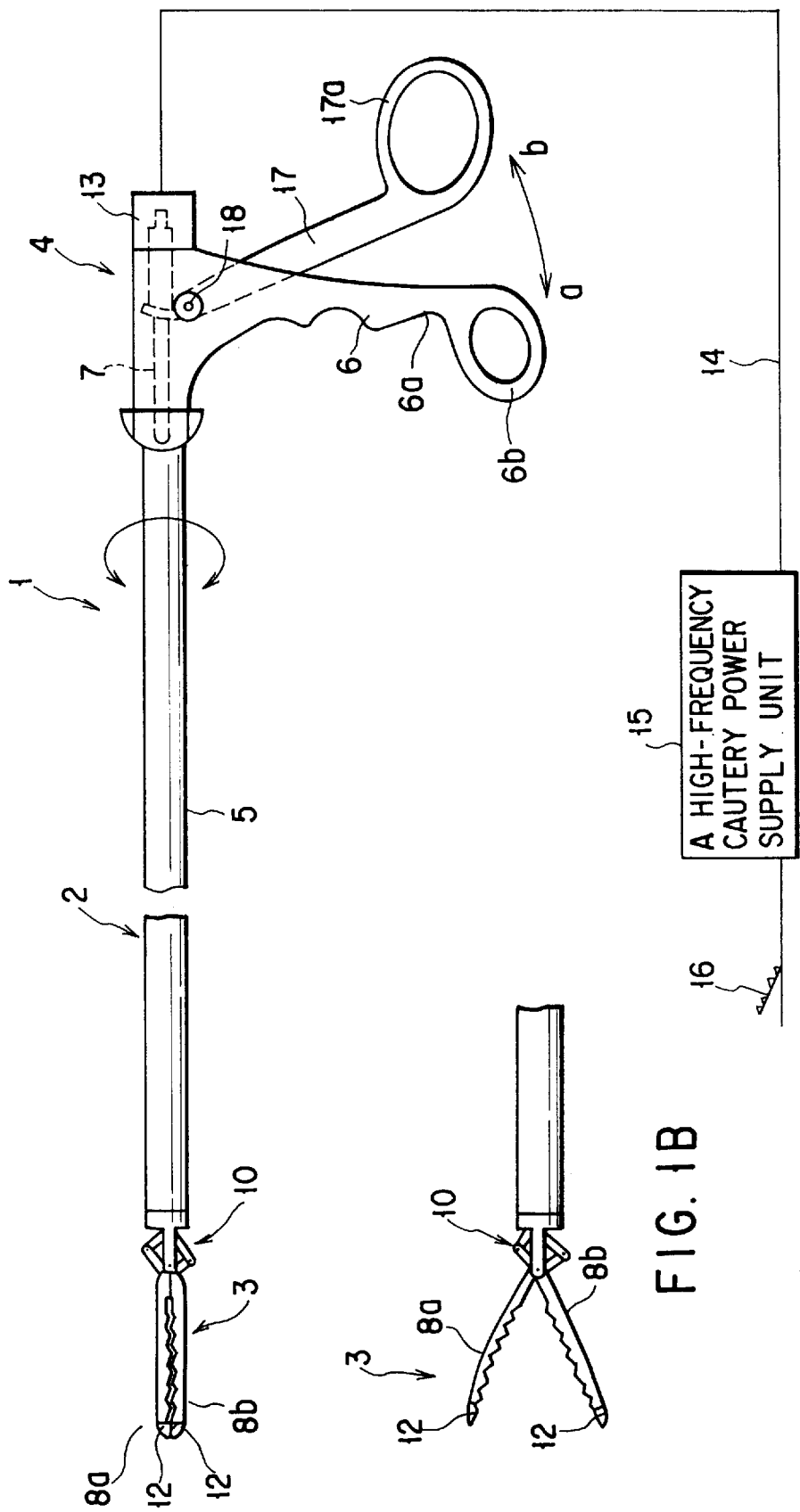
FIGS. 1A and 1B are side views of a high-frequency treatment tool according to the first embodiment of the present invention.
Figure 2:
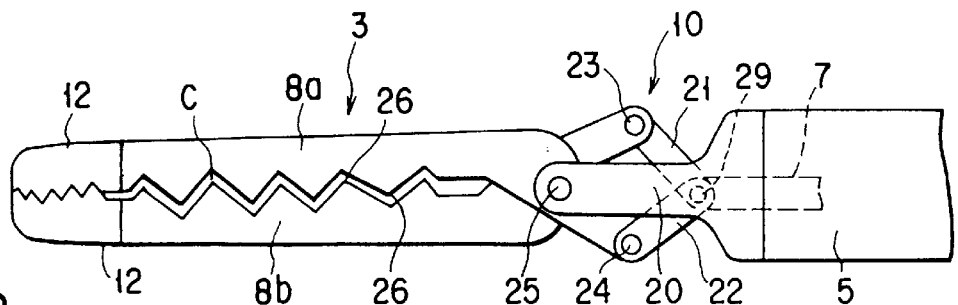
FIG. 2 is an enlarged side view of the treatment portion of the high-frequency treatment tool shown in FIG. 1A.

FIGS. 1A, 1B, and 2 show the first embodiment of the present invention. As shown in FIGS. 1A and 1B, a bipolar forceps 1 as a high-frequency treatment tool of this embodiment comprises a long insertion portion 2 to be inserted into the body cavity of a patient, a treatment portion 3 attached to the distal end portion of the insertion portion 2 to grip vital tissue and coagulate or incise it, and an operation portion 4 coupled to the proximal end portion of the insertion portion 2. A high-frequency current is supplied to the treatment portion 3 through a conductive member (not shown), so vital tissue gripped by the treatment portion 3 is coagulated or incised.

The insertion portion 2 has a rotatable sheath 5. A rod 7 movable back and forth is arranged in the sheath 5. A pair of jaws 8a and 8b forming the treatment portion 3 are coupled to the distal end of the rod 7 through a link mechanism 10. These jaws 8a and 8b function as gripping members for gripping tissue and electrodes for flowing a high-frequency current to the gripped tissue.

As more specifically shown in FIG. 2, the link mechanism 10 has a pair of links 21 and 22 pivotally coupled to the distal end of the rod 7 through a pivot pin 29. The first link 21 is pivotally coupled to the proximal end portion of one jaw 8b through a pivot pin 23. The second link 22 is pivotally coupled to the proximal end portion of the other jaw 8a through a pivot pin 24. The pair of jaws 8a and 8b are pivotally coupled to each other through a pin 25 supported by a pair of arms 20 extending from both sides of the distal end portion of the sheath 5. According to this arrangement, when the rod 7 moves back and forth, the link mechanism 10 operates to pivot the jaws 8a and 8b about the pin 25 (the treatment portion 3 is opened/closed). To reliably grip vital tissue with the jaws 8a and 8b, serrate portions 26 meshing each other upon closing the treatment portion 3 are formed on the inner gripping surfaces of the jaws 8a and 8b.

The distal end portions of the jaws 8a and 8b are formed as insulating portions 12. The insulating portions 12 may be formed by forming the entire distal end portions of the jaws 8a and 8b from a material having electrical insulating properties. The insulating portions 12 may be made entirely of material having electrical insulating properties wherein the thickness of the insulating portions at at least one point is equal to a thickness of the corresponding jaw 8a, 8b. Alternatively, the insulating portions 12 may be formed by insulating coating on the outer surfaces of the distal end portions of the jaws 8a and 8b. As the material having electrical insulating properties and used for the insulating portions 12, a ceramic having the highest heat resistance and free from degradation in electrical insulating properties is preferably used. In this embodiment, in the state shown in FIG. 2 in which the treatment portion 3 is completely closed, only the insulating portions 12 of the jaws 8a and 8b mesh and contact each other, and a predetermined gap C is formed between the gripping surfaces (serrate portions 26) of the jaws 8a and 8b except the insulating portions 12. That is, when tissue is gripped, the conductive portions of the jaws 8a and 8b to which a high-frequency current is supplied do not come into contact with each other (no electrical short circuit occurs between the jaws 8a and 8b).

As shown in FIG. 1A, the conductive member electrically connected to the jaws 8a and 8b extends through the sheath 5 and is connected to a connector receptacle 13 of the operation portion 4. A cable 14 extending from a high-frequency cautery power supply unit 15 is connected to the connector receptacle 13. The high-frequency cautery power supply unit 15 has a foot switch 16 for turning on/off the power supply unit 15.

The operation portion 4 has a grip 6 which can be gripped with a hand. The grip 6 has a finger hook portion 6a on which the operator places the thumb and a finger hook portion 6b on which the operator places the middle finger. The grip 6 also has a trigger 17 as a forceps operation means. This trigger 17 is pivotally coupled to the upper end portion of the grip 6 through a pivot pin 18. The trigger 17 is coupled to the proximal end portion of the rod 7. The trigger 17 has finger hook portions 17a on which the operator places the index finger.

A case in which tissue is coagulated using the bipolar forceps 1 with the above arrangement will be described next.

First, the cable 14 is connected to the connector receptacle 13 of the bipolar forceps 1 to electrically connect the bipolar forceps 1 to the high-frequency cautery power supply unit 15. Subsequently, the trigger 17 of the operation portion 4 is pivoted in a direction indicated by an arrow a to move the rod 7 backward to the hand side and close the jaws 8a and 8b (treatment portion 3) through the link mechanism 10. In this state, the insertion portion 2 of the bipolar forceps 1 is inserted into the body of a patient, and the treatment portion 3 at the distal end of the insertion portion 2 is moved close to the tissue to be treated in the body.

When the treatment portion 3 is positioned near the tissue to be treated, the trigger 17 is pivoted in a direction indicated by an arrow b to move the rod 7 forward and open the jaws 8a and 8b (treatment portion 3) through the link mechanism 10 (FIG. 1B). The vital tissue is inserted between the opened jaws 8a and 8b. When the trigger 17 is operated to close the jaws 8a and 8b again, the vital tissue is gripped by the jaws 8a and 8b. Even when the vital tissue is membranous tissue, the conductive portions of the jaws 8a and 8b to which the high-frequency current is supplied do not come into contact with each other (no electrical short circuit occurs between the jaws 8a and 8b). This is because when the treatment portion 3 is completely closed, only the insulating portions 12 of the jaws 8a and 8b mesh and contact each other, and the predetermined gap C is formed between the gripping surfaces (serrate portions 26) of the jaws 8a and 8b except the insulating portions 12.

In this state, when a high-frequency current is supplied from the high-frequency cautery power supply unit 15 to the connector receptacle 13 through the cable 14, a coagulation current having a predetermined frequency is flowed across the jaws 8a and 8b, so the vital tissue can be coagulated. Subsequently, when the trigger 17 is pivoted in the direction a to close the jaws 8a and 8b, and an incision current having a predetermined frequency is flowed across the jaws 8a and 8b, the tissue can be incised by the jaws 8a and 8b.

As described above, in the bipolar forceps 1 of this embodiment, when the treatment portion 3 is completely closed, only the insulating portions 12 of the jaws 8a and 8b mesh and contact each other, and the predetermined gap C is formed between the gripping surfaces (serrate portions 26) of the jaws 8a and 8b except the insulating portions 12. That is, when tissue is gripped, the conductive portions of the jaws 8a and 8b to which a high-frequency current is supplied do not come into contact with each other. Hence, when tissue is gripped by the jaws 8a and 8b, no electrical short circuit occurs between the jaws 8a and 8b. For this reason, even thin membranous tissue can be reliably coagulated or incised. As a prior art, Jpn. Pat. Appln, KOKAI Publication No. 8-317936 discloses an arrangement in which a U-shaped insulating member is arranged on the gripping surface of a jaw. This insulating member aims at applying a pressure to the gripped tissue for proper coagulation and cannot prevent an electrical short circuit between the jaws.

In the bipolar forceps 1 of this embodiment, the insulating portions 12 are formed only at the distal end portions of the jaws 8a and 8b. Hence, the tissue coagulation range can be increased without any short circuit between the conductive portions (the conductive tissue area can be increased).

In this embodiment, the insulating portions 12 are formed on the jaws 8a and 8b. However, the insulating portion may be formed on only one jaw 8a (8b). It is only necessary that at least one of portions of the jaws 8a and 8b which come into contact with each other upon closing the treatment portion 3 is formed as the insulating portion 12.

Figure 3:
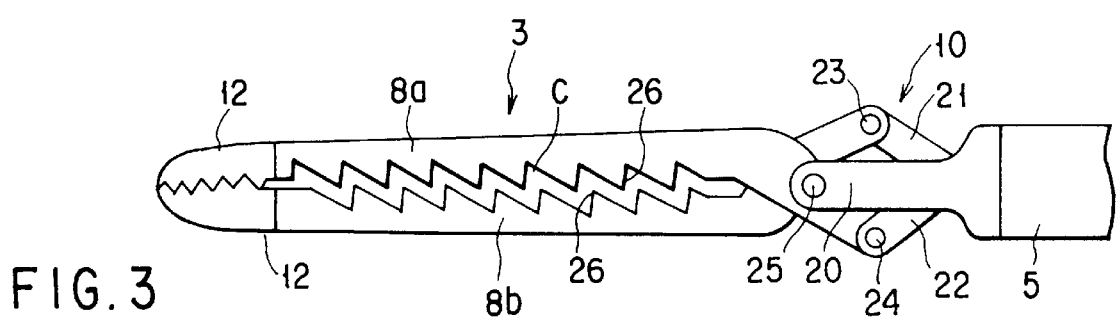
FIG. 3 is an enlarged side view of the treatment portion of a high-frequency treatment tool according to the second embodiment of the present invention.

FIG. 3 shows the second embodiment of the present invention. A high-frequency treatment tool of this embodiment has the same arrangement as that of the first embodiment except the shape of serrate portions 26 formed on the gripping surfaces of jaws 8a and 8b. Hence, the same function and effect as in the first embodiment can be obtained.

Figure 4A:
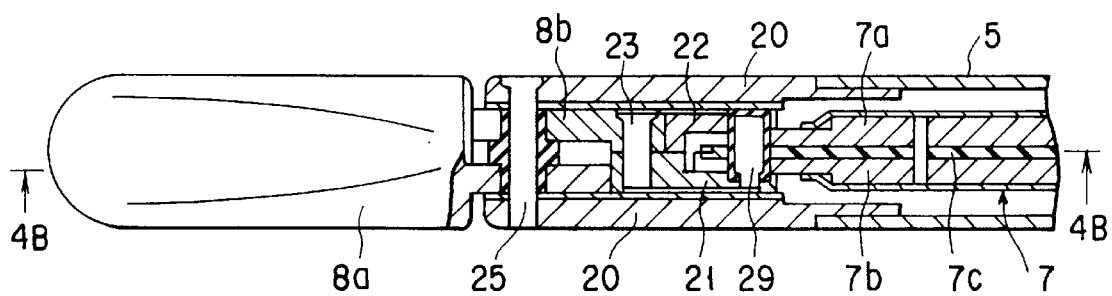
FIG. 4A is a cross-sectional view showing a high-frequency treatment tool according to the third embodiment of the present invention.
Figure 4B:
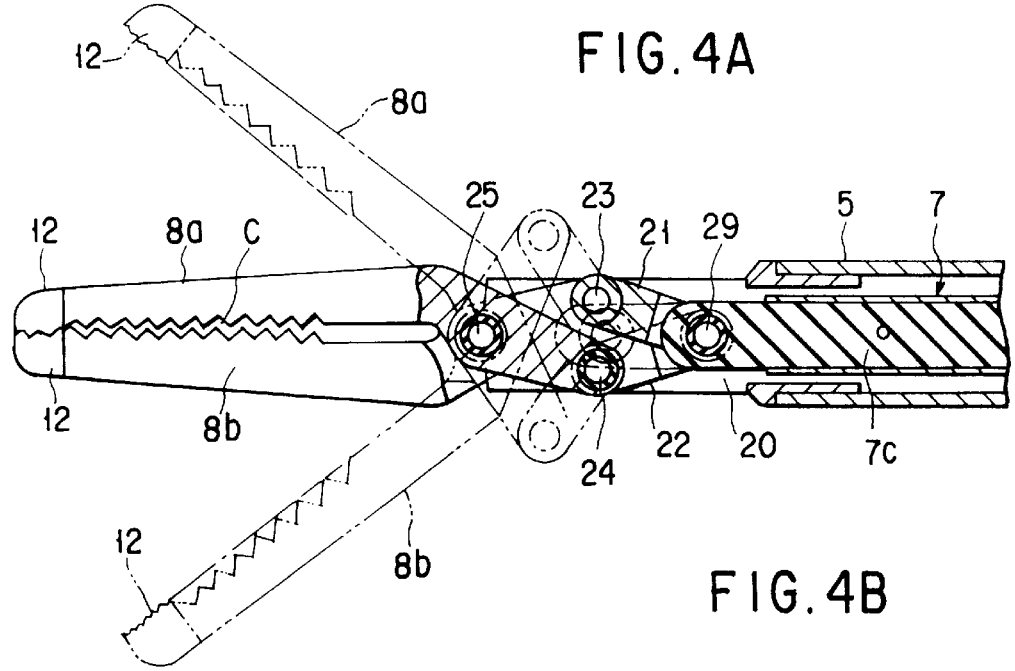
FIG. 4B is a longitudinal sectional view taken along a line 4B—4B in FIG. 4A.

FIGS. 4A and 4B show the third embodiment of the present invention. For a high-frequency treatment tool of this embodiment, the conductive path of a high-frequency current to jaws 8a and 8b is formed by a rod 7 and links 21 and 22 in the arrangement of the first embodiment. More specifically, the pair of links 21 and 22 are pivotally coupled to the distal end of the rod 7 through a pivot pin 29. The first link 21 is pivotally coupled to the proximal end portion of one jaw 8b through a pivot pin 23. The second link 22 is pivotally coupled to the proximal end portion of the other jaw 8a through a pivot pin 24. The pair of jaws 8a and 8b are pivotally coupled to each other through a pin 25 supported by a pair of arms 20 extending from both sides of the distal end portion of a sheath 5.

The rod 7 has two conductive regions 7a and 7b electrically insulated from each other by an insulating member 7c. The conductive region 7a is electrically connected to one jaw 8a through the second link 22. The conductive region 7b is electrically connected to the other jaw 8b through the first link 21. To electrically insulate the conductive path formed by the conductive region 7a and second link 22 from the conductive path formed by the conductive region 7b and first link 21, the pivot pins 24, 25, and 29 are covered with insulating tubes. The remaining portions including insulating portions 12 have the same arrangement as in the first embodiment.

According to this embodiment, the same function and effect as in the first embodiment can be obtained. Additionally, the conductive paths to the jaws 8a and 8b can be simplified.

Figure 5A:
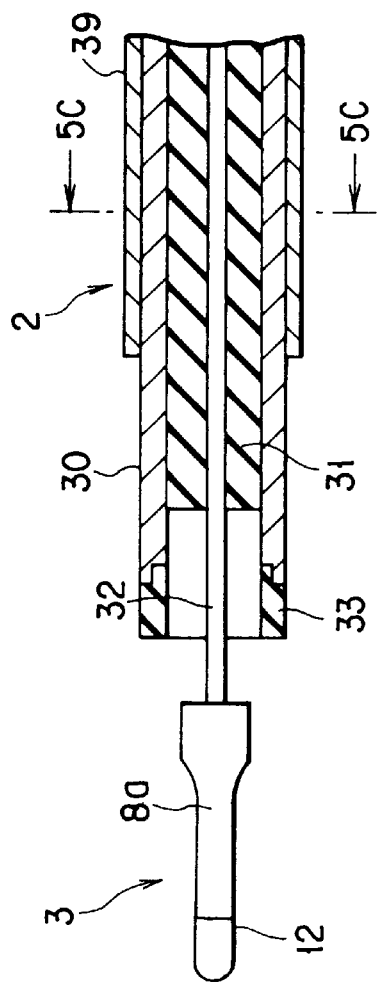
FIG. 5A is a cross-sectional view showing a high-frequency treatment tool according to the fourth embodiment of the present invention.
Figure 5B:
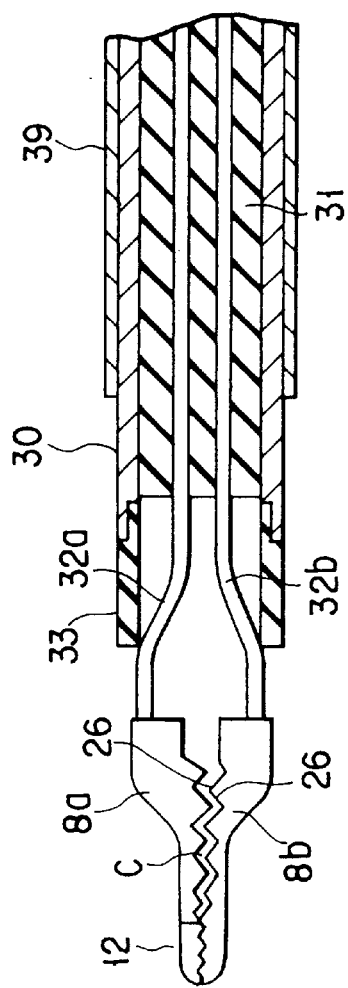
FIG. 5B is a longitudinal sectional view of the high-frequency treatment tool shown in FIG. 5A.
Figure 5C:
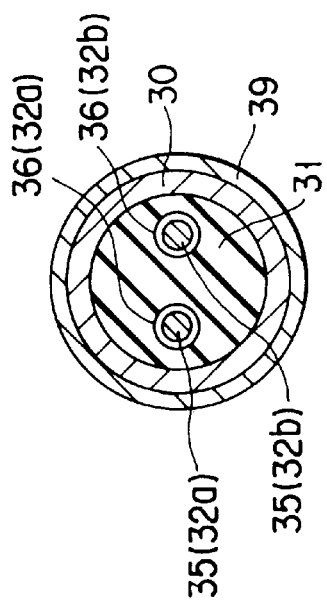
FIG. 5C is a sectional view taken along a line 5C—5C in FIG. 5A.

FIGS. 5A to 5C show the fourth embodiment of the present invention. A bipolar forceps as a high-frequency treatment tool of this embodiment comprises a long insertion portion 2 to be inserted into the body cavity of a patient, a treatment portion 3 attached to the distal end portion of the insertion portion 2 to grip vital tissue and coagulate or incise it, and an operation portion (not shown) coupled to the proximal end portion of the insertion portion 2. The operation portion of this embodiment has the same arrangement as that of the operation portion 4 of the first embodiment. Hence, for the operation portion, the same reference numerals as in the first embodiment denote the same parts in the fourth embodiment, and a detailed description thereof will be omitted.

The insertion portion 2 is comprised of a rotatable outer sheath 39 and an inner sheath 30 inserted in the outer sheath 39 to move back and forth. The inner sheath 30 is inserted into a grip 6 of the operation portion. The proximal end portion of the inner sheath 30 is coupled to a trigger 17. A cap 33 having electrical insulating properties is connected and fixed to the distal end portion of the inner sheath 30.

A gripping member 31 having electrical insulating properties is fitted in the inner sheath 30. A pair of elastic members 32a and 32b are stationarily held by the holding member 31. The elastic members 32a and 32b are comprised of conductive rods 35 formed from a spring steel or the like. Each conductive rod 35 is covered with an insulating tube 36. The proximal end portions of the conductive rods 35 of the elastic members 32a and 32b are connected to a connector receptacle 13 of an operation portion 4. The elastic members 32a and 32b have jaws 8a and 8b at their distal ends, respectively, and always bias the jaws 8a and 8b in the opening direction.

In this arrangement, when the trigger 17 is pulled to the grip 6 side (in a direction b in FIG. 1A), the inner sheath 30 moves forward in the axial direction, and the elastic members 32a and 32b are relatively retracted into the inner sheath 30 (FIG. 5B). At this time, the elastic members 32a and 32b are pressed inward by the inner wall of the inner sheath 30 to close the jaws 8a and 8b. On the other hand, when the trigger 17 is pivoted and separated from the grip 6 (in a direction a in FIG. 1A), the elastic members 32a and 32b relatively project from the inner sheath 30, so the jaws 8a and 8b are opened by the restoring force of the elastic members 32a and 32b.

The distal end portion of one jaw 8a is formed as an insulating portion 12. The insulating portion 12 may be formed by forming the entire distal end portion of the jaw 8a from a material having electrical insulating properties. Alternatively, the insulating portion 12 may be formed by insulating coating of the outer surface of the distal end portion of the jaw 8a. In this embodiment, in the state shown in FIG. 5B in which the treatment portion 3 is completely closed, only the insulating portion 12 of the jaw 8a meshes and contacts the distal end portion of the other jaw 8b, and a predetermined gap C is formed between the gripping surface (serrate portion 26) of the jaw 8a except the insulating portion 12 and the gripping surface (serrate portion 26) of the jaw 8b. That is, when tissue is gripped, the conductive portions of the jaws 8a and 8b to which a high-frequency current is supplied do not come into contact with each other (no electrical short circuit occurs between the jaws 8a and 8b). The remaining portions have the same arrangement as that of the first embodiment.

According to the bipolar forceps of this embodiment, the same function and effect as in the first embodiment can be obtained.

FIGS. 6A to 6D show the fifth embodiment of the present invention. A high-frequency treatment tool of this embodiment is a ventromy forceps 40 in the form of scissors and has a pair of forceps members 41a and 41b with the same shape. The forceps members 41a and 41b are formed from conductive members and are pivotally coupled to each other through a pivot shaft 42 at almost middle portions. The proximal end portions of the forceps members 41a and 41b are formed as finger hook portions 44a and 44b, respectively. Cables 45a and 45b connected to a high-frequency cautery power supply unit (not shown) are connected to the finger hook portions 44a and 44b, respectively.

The forceps members 41a and 41b have jaws 42a and 42b at their distal end portions, respectively. To reliably grip vital tissue with the jaws 42a and 42b, serrate portions 26 meshing each other upon closing the jaws 42a and 42b are formed on the inner gripping surfaces of the jaws 42a and 42b.

The pair of forceps members 41a and 41b and pivot shaft 42 are covered with insulating members 46. Only the serrate portions 26 formed on the jaws 42a and 42b are exposed from the insulating members 46 to form electrode portions. Bent portions 43 bent inward are formed at the distal end portions of the jaws 42a and 42b.

In this embodiment, in the state shown in FIG. 6A in which the jaws 42a and 42b are completely closed, only the bent portions 43 (corresponding to the insulating portions 12 in the first embodiment) of the jaws 42a and 42b covered with the insulating members 46 mesh and contact each other, and a predetermined gap C is formed between the gripping surfaces (serrate portions 26) of the jaws 42a and 42b except the bent portions 43. That is, when tissue is gripped, the conductive portions (serrate portions 26) of the jaws 42a and 42b to which a high-frequency current is supplied do not come into contact with each other (no electrical short circuit occurs between the jaws 42a and 42b).

In the ventromy forceps 40 having the above arrangement, when vital tissue is gripped between the serrate portions 26 of the jaws 42a and 42b, and a coagulation current or incision current is flowed to the serrate portions 26 through the conductive portions of the forceps members 41a and 41b, the vital tissue can be coagulated or incised.

As described above, in the ventromy forceps 40 of this embodiment, when the jaws 42a and 42b are completely closed, only the bent portions (insulating portions) 43 of the jaws 42a and 42b mesh and contact each other, and the predetermined gap C is formed between the gripping surfaces (serrate portions 26) of the jaws 42a and 42b except the bent portions 43. Hence, when tissue is gripped by the jaws 42a and 42b, no electrical short circuit occurs between the jaws 42a and 42b. For this reason, even thin membranous tissue can be reliably coagulated or incised.

Figure 7A:
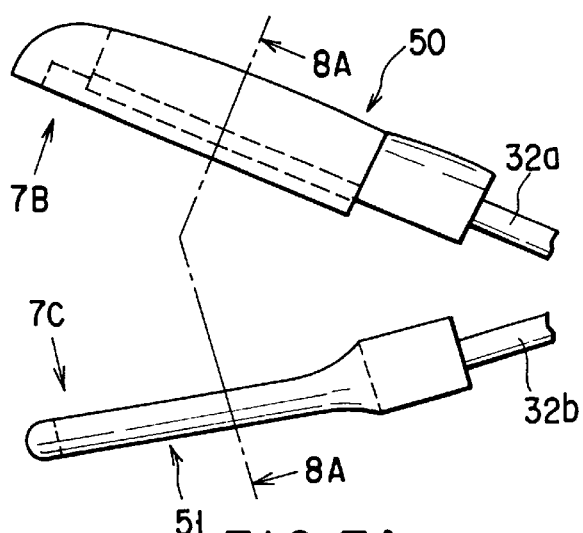
FIG. 7A is a side view of a high-frequency treatment tool according to the sixth embodiment of the present invention.

FIGS. 7A to 9C show the sixth embodiment of the present invention. As shown in FIG. 7A, a high-frequency treatment tool of this embodiment has a pair of gripping members 50 and 51 for gripping vital tissue to coagulate or incise it. The gripping members 50 and 51 are opened/closed by, e.g., the same mechanism as in the fourth embodiment shown in FIGS. 5A to 5C. The insertion and operation portions for supporting the gripping members 50 and 51 also have the same arrangement as in the fourth embodiment. For the insertion and operation portions, the same reference numerals as in the fourth embodiment denote the same parts in the sixth embodiment, and a detailed description thereof will be omitted.

Figure 7B:
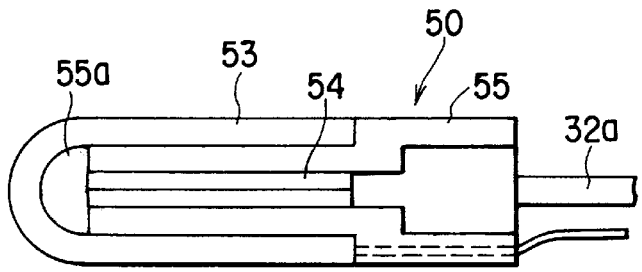
FIG. 7B is a view seen from a direction indicated by an arrow 7B in FIG. 7A.
Figure 7C:
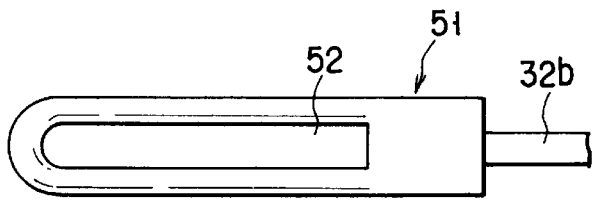
FIG. 7C is a view seen from a direction indicated by an arrow 7C in FIG. 7A.

As shown in FIG. 7C, one gripping member 51 is formed as a first electrode portion consisting of a conductive material. The first electrode portion 51 has a through hole 52 extending in the longitudinal direction and therefore has an almost loop shape.

Figure 8A:
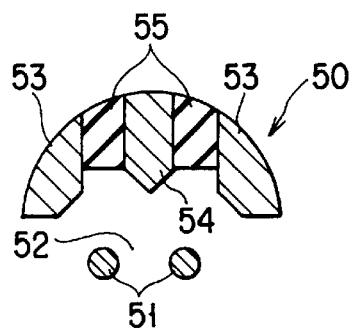
FIGS. 8A and 8B are sectional views taken along a line 8—8 in FIG. 7A.
Figure 8B:
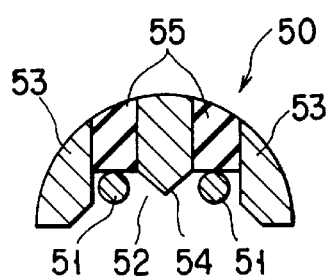

As shown in FIG. 7B, the other gripping member 50 has two electrode portions 53 and 54 electrically insulated from each other by an insulating member 55. The insulating member 55 has a shape almost conforming to the first electrode portion 51 and comes into contact with the first electrode portion 51 when the gripping members 50 and 51 are closed, as shown in FIG. 8B. The second electrode portion 53 outside the insulating member 55 functions as a coagulation electrode. The electrode portion 53 extends in an almost U shape along the insulating member 55 and is also positioned on both sides of the first electrode portion 51 to surround it when the gripping members 50 and 51 are closed as shown in FIG. 8B. The third electrode portion 54 inside the insulating member 55 functions as an incision electrode. The electrode portion 54 projects in a chevron shape from the gripping surface of the insulating member 55 and also enter the through hole 52 of the first electrode portion 51 when the gripping members 50 and 51 are closed, as shown in FIG. 8B.

The electrode portions 51, 53, and 54 are connected to a connector receptacle 13 of an operation portion 4 through conductive rods 35 of elastic members 32a and 32b, so a high-frequency current is supplied from a high-frequency cautery power supply unit 15 through a cable 14.

Figure 9A:
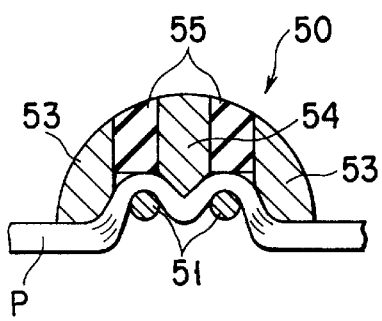
FIGS. 9A to 9C are sectional views showing a use form of the high-frequency treatment tool shown in FIG. 7A.
Figure 9B:
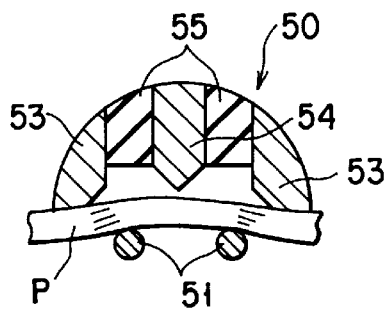
Figure 9C:
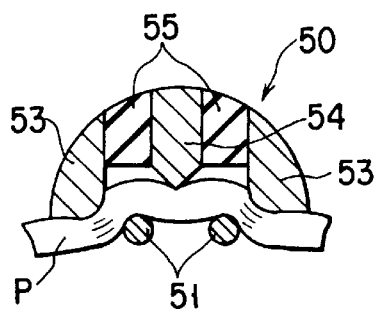

FIGS. 9A to 9C show steps of coagulating/incising vital tissue P using the gripping members 50 and 51 having the above arrangement. FIG. 9A shows a state wherein the gripping members 50 and 51 are opened to position the vital tissue P between the gripping members 50 and 51, and then, the gripping members 50 and 51 are closed to sandwich the vital tissue P between the gripping members 50 and 51. Even when the vital tissue P is membranous tissue, the electrode portions 51 and 53 or electrode portions 51 and 54 to which a high-frequency current is supplied do not come into contact. This is because when the gripping members 50 and 51 are completely closed, the first electrode portion 51 comes into contact with only the insulating member 55. In this state, a coagulation current is flowed across the second electrode portion 53 as the coagulation electrode and the first electrode portion 51 to coagulate the vital tissue P.

Upon completing coagulation, the gripping members 50 and 51 are slightly opened, as shown in FIG. 9B, to switch the power to an incision current. The gripping members 50 and 51 are closed again, and the incision current is flowed across the third electrode portion 54 as the incision electrode and the first electrode portion 51 to incise the vital tissue P, as shown in FIG. 9C.

As described above, in the high-frequency treatment tool of this embodiment, when the gripping members 50 and 51 are completely closed, the first electrode portion 51 comes into contact with only the insulating member 55. That is, when tissue is gripped by the gripping members 50 and 51, the electrode portions 51 and 53 or electrode portions 51 and 54 to which a high-frequency current is supplied do not come into contact with each other. Hence, no electrical short circuit occurs between the gripping members 50 and 51, and even thin membranous tissue can be reliably coagulated or incised.

In this embodiment, even when the operator strongly grips a trigger 17 of the operation portion, the electrode portions do not short-circuit. For this reason, proper coagulation or incision can be performed. In addition, since the operation force of the trigger 17 need not be finely adjusted, the operability is good.

In this embodiment, an insulating member 55 is inserted between the electrode portions 53 and 54 of the gripping member 50, so the tissue can also be gripped by the insulating portion 55. Hence, the operator can reliably grip and coagulate/incise the tissue without missing it.

In this embodiment, to prevent short circuit between the electrode portions 51, 53, and 54, a distal end region 55a of the gripping surface of the insulating member 55 may be formed at a higher level than that of the remaining regions instead of forming the entire gripping surface of the insulating member 55 at the uniform level. With this setting, when the gripping members 50 and 51 are completely closed, the distal end portion of the first electrode portion 51 comes into contact with only the distal end region 55a, and a predetermined gap is formed between the gripping surfaces of the gripping members 50 and 51, as in the first embodiment.

Figures 10, 11:
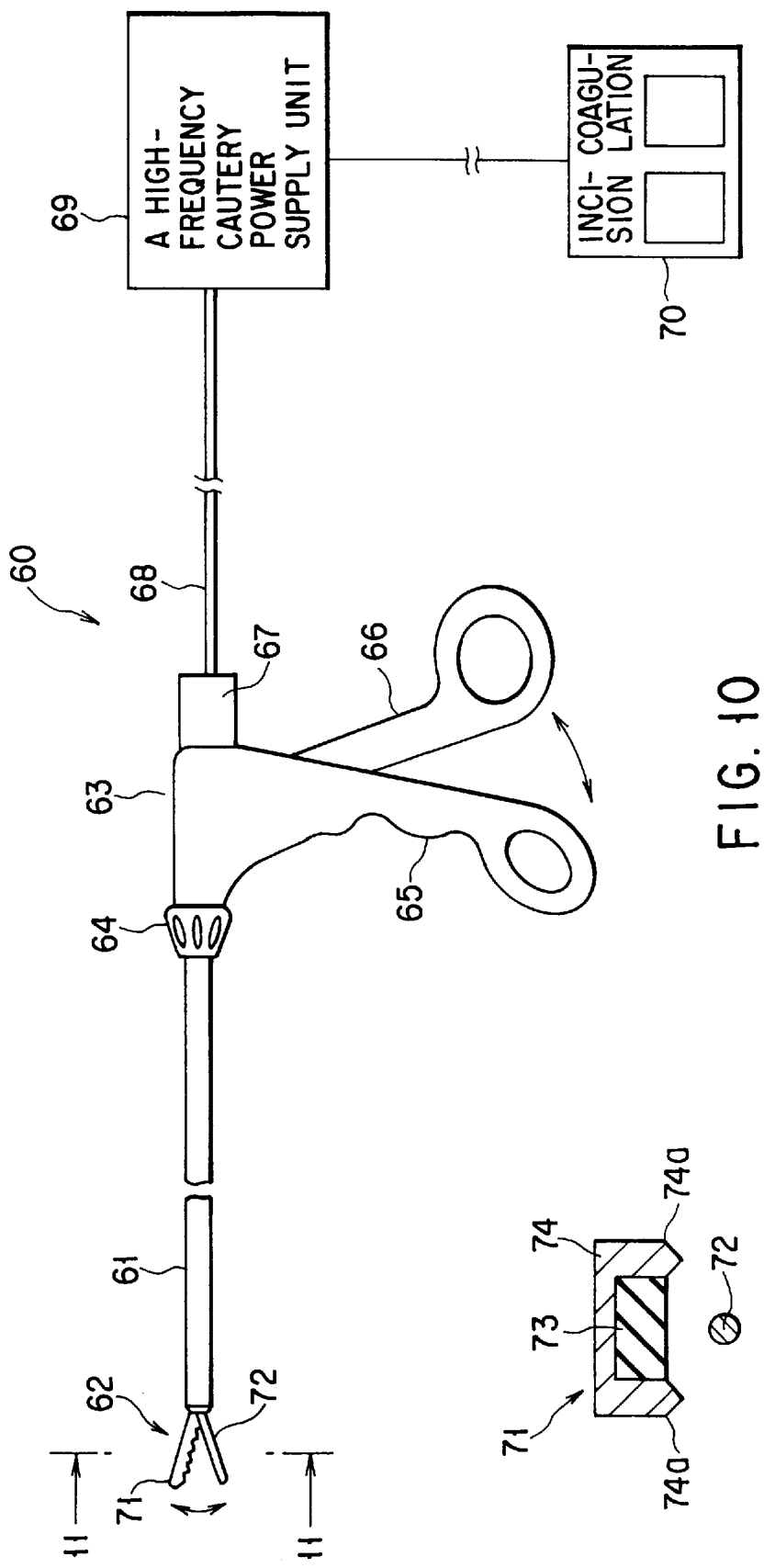
FIG. 10 is a side view of a high-frequency treatment tool according to the seventh embodiment of the present invention.
FIG. 11 is a sectional view taken along a line 11—11 in FIG. 10.

FIGS. 10 to 12B show the seventh embodiment of the present invention. As shown in FIG. 10, a bipolar forceps 60 as a high-frequency treatment tool of this embodiment comprises a sheath 61 as an insertion portion to be inserted into the body cavity of a patient, a treatment portion 62 attached to the distal end portion of the sheath 61 to grip vital tissue and coagulate or incise it, and an operation portion 63 coupled to the proximal end portion of the sheath 61. The sheath 61 is rotated by operating a rotary operation portion 64 on the operation portion 63 side.

The treatment portion 62 has a pair of jaws 71 and 72 which can be opened/closed. The operation portion 63 has a fixed handle 65 and a movable handle 66. The jaws 71 and 72 are opened/closed by pivoting the movable handle 66.

A conductive member serving as a path for supplying a high-frequency current is electrically connected to the jaws 71 and 72. This conductive member extends through the sheath 61 and is connected to a connector receptacle 67 of the operation portion 63. A cable 68 extending from a high-frequency cautery power supply unit 69 is connected to the connector receptacle 67. The high-frequency cautery power supply unit 69 has a foot switch 70 for turning on/off the power supply unit 69. The foot switch 70 has an incision switch portion and a coagulation switch portion.

As shown in FIG. 11 in detail, the first jaw 71 on one side of the treatment portion 62 comprises a main body portion 74 formed from a conductive material and having a U-shaped section. Serrate gripping portions 74a are formed on both sides of the main body portion 74. In the main body portion 74, an insulating member 73 for gripping tissue together with the gripping portions 74a is fixed between the gripping portions 74a. This insulating member 73 is substantially arranged throughout the total length of the main body portion 74. The second jaw 72 on the other side of the treatment portion 62 has formed as a rod consisting of a conductive material and having a circular section. The second jaw 72 is located to come into contact with only the insulating member 73 when the treatment portion 62 is closed.

Figure 12A:
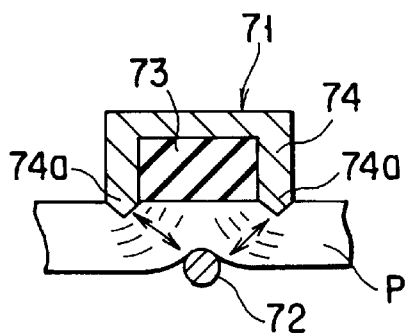
FIGS. 12A and 12B are sectional views showing a use form of the high-frequency treatment tool shown in FIG. 10.
Figure 12B:
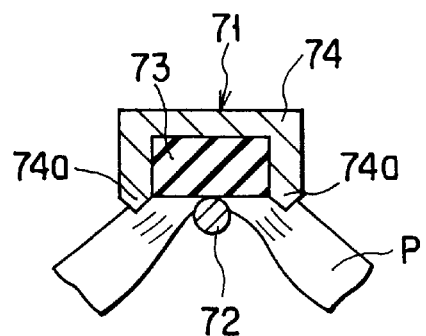

FIGS. 12A and 12B show steps of coagulating/incising tissue P using the bipolar forceps 60 having the above arrangement. FIG. 12A shows a state wherein the tissue P is sandwiched by the gripping portions 74a of the first jaw 71 and second jaw 72. Even when the tissue P is membranous one, the jaws 71 and 72 to which a high-frequency current is supplied do not come into contact. This is because when the treatment portion 62 is completely closed, the second jaw 72 comes into contact with only the insulating member 73. In this state, a coagulation current is flowed across the jaws 72 and 72 to coagulate the tissue P.

Upon completing coagulation, the treatment portion 62 is more tightly closed to sandwich the tissue P by the gripping portions 74a of the first jaw 71, insulating member 73, and second jaw 72. At this time as well, the jaws 71 and 72 do not come into contact with each other. In this state, an incision current is flowed across the jaws 71 and 72 to incise the tissue P.

As described above, in the bipolar forceps 60 of this embodiment, when the treatment portion 62 is completely closed, the second jaw 72 comes into contact with only the insulating member 73 of the first jaw 71. That is, when tissue is gripped by the jaws 71 and 72, the electrode portions to which a high-frequency current is supplied do not come into contact with each other. Hence, no electrical short circuit occurs between the jaws 71 and 72, and even thin membranous tissue can be reliably coagulated or incised.

In the bipolar forceps 60 of this embodiment, the insulating member 73 is sandwiched by the gripping portions 74a of the first jaw 71, and the tissue is also gripped by this insulating member 73. Hence, the operator can reliably grip the tissue without missing it and coagulate/incise it (This also applies to the sixth embodiment. Especially, when the tissue is gripped by part of the jaws or the jaw has a rod shape, as in this embodiment, an insulating member commonly used as a gripping means and a short circuit prevention means is very effective). To the contrary, a high-frequency treatment tool disclosed in DE 4032471 C2 grips tissue by three rod electrodes. For this reason, the tissue is missed upon gripping and cannot be reliably gripped, and coagulation or incision cannot be reliably performed.

Figure 13A:
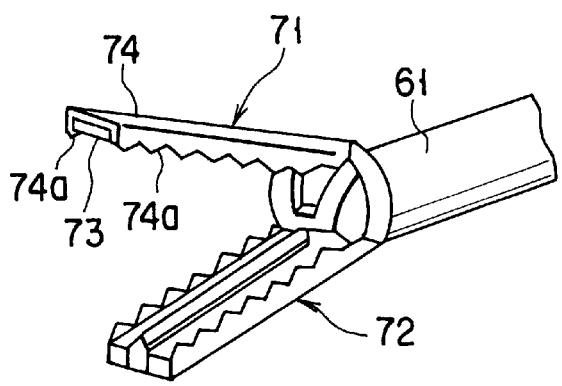
FIG. 13A is a perspective view of a high-frequency treatment tool according to the eighth embodiment of the present invention.
Figure 13B:
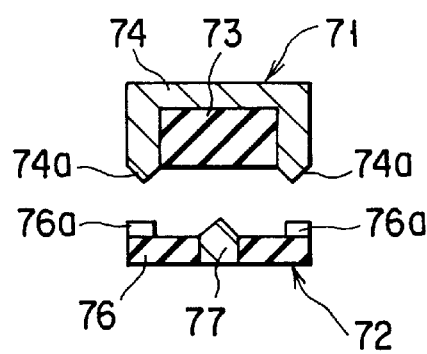
FIG. 13B is a sectional view of a treatment portion of the high-frequency treatment tool shown in FIG. 13A.

FIGS. 13A and 13B show the eighth embodiment of the present invention. In a high-frequency treatment tool of this embodiment, the arrangement of a second jaw 72 is different from that in the seventh embodiment. More specifically, in this embodiment, the second jaw 72 comprises a main body portion 76 consisting of a material having electrical insulating properties and an electrode portion 77 consisting of a conductive material and arranged almost at the central portion of the main body portion 76 to substantially extend along the total length of the main body portion 76. Serrate gripping portions 76a meshing with gripping portions 74a of a first jaw 71 are formed on both sides of the main body portion 76. The arrangement of the remaining portions is the same as in the seventh embodiment.

According to this arrangement, since the second jaw 72 also has the gripping portions 76a, the tissue gripping area increases as compared to the seventh embodiment, so tissue can be reliably gripped.

Figure 14:
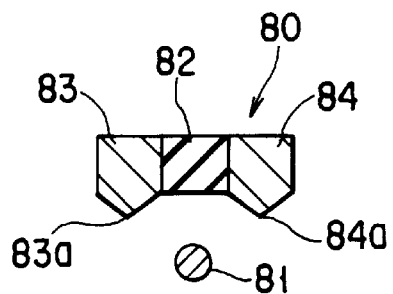
FIG. 14 is a sectional view of a treatment portion of a high-frequency treatment tool according to the ninth embodiment of the present invention.

FIGS. 14 to 16B show the ninth embodiment of the present invention. As shown in FIG. 14, a bipolar forceps as a high-frequency treatment tool of this embodiment has a treatment portion comprising a first jaw 80 and a second jaw 81. The first jaw 80 has two coagulation electrode portions 83 and 84 electrically insulated from each other by an insulating member 82. In this case, the first coagulation electrode portion 83 and second coagulation electrode portion 84 are positioned on both sides of the insulating member 82 to sandwich the insulating member 82. The distal ends of the electrode portions 83 and 84 are formed as serrate gripping portions 83a and 84a, respectively. The second jaw 81 comprises a rod consisting of a conductive material and having a circular section and is formed as an incision electrode portion. The second jaw (electrode portion) 81 is located to come into contact with only the insulating member 82 when the treatment portion is kept closed.

Figure 15:
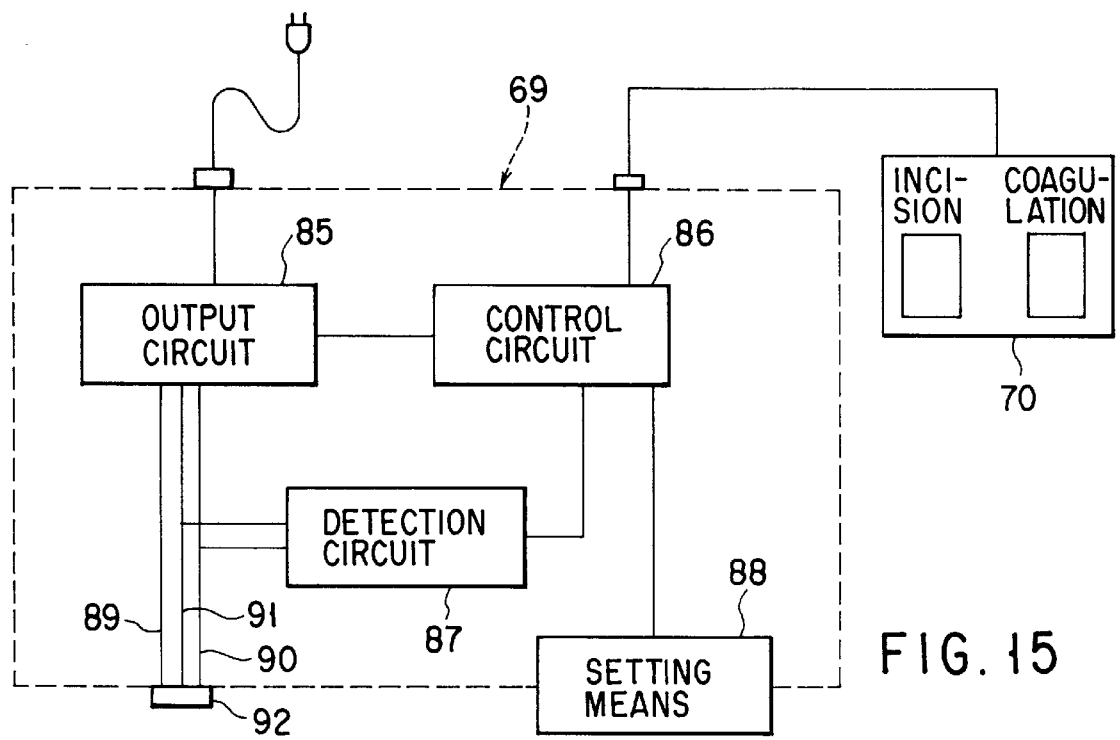
FIG. 15 is a block diagram showing the circuit arrangement of a power supply unit for supplying a high-frequency current to the treatment portion shown in FIG. 14.

A high-frequency cautery power supply unit 69 for supplying a high-frequency current to the electrode portions 81, 83, and 84 has an arrangement shown in FIG. 15. Referring to FIG. 15, reference numeral 85 denotes an output circuit for supplying a high-frequency current; 86, a control circuit for controlling the high-frequency output from the output circuit 85 in accordance with a control signal from a foot switch 70; 88, a setting means for inputting a predetermined output condition to the control circuit 86 as an electrical signal; 92, a connector to which a power supply cable from the bipolar forceps is connected; 89, 90, and 91, lines for connecting the output circuit 85 to the connector 92 in correspondence with the electrode portions 81, 83, and 84, respectively; and 87, a detection circuit for detecting the high-frequency current flowing through the lines 89, 90, and 91 and sending a detection signal to the line 89. The arrangement of the remaining portions is the same as in the seventh embodiment.

Figure 16A:
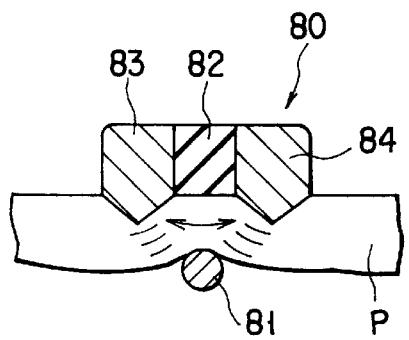
FIGS. 16A and 16B are sectional views showing a use form of the treatment portion shown in FIG. 14.
Figure 16B:
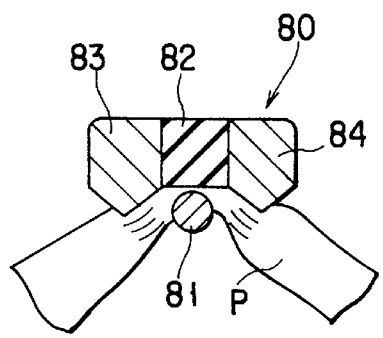

FIGS. 16A and 16B show steps of coagulating/incising tissue P using the bipolar forceps having the above arrangement. FIG. 16A shows a state wherein the tissue P is sandwiched by the first jaw 80 and second jaw 81. Even when the tissue P has a thin film shape, the jaws 80 and 81 to which a high-frequency current is supplied do not come into contact with each other. This is because when the treatment portion is completely closed, the second jaw 81 comes into contact with only the insulating member 82. In this state, a coagulation current is flowed across the two coagulation electrode portions 83 and 84 of the first jaw 80 to coagulate the tissue P.

Upon completing coagulation, the treatment portion is further tightly closed, and the tissue P is pressed against the insulating member 82 by the second jaw 81. In this case as well, the jaws 80 and 81 do not come into contact with each other. In this state, an incision current is flowed across the first coagulation electrode portion 83 and the incision electrode portion (second jaw) 81 and across the second coagulation electrode portion 84 and the incision electrode portion (second jaw) 81 to incise the tissue P.

As described above, in the bipolar forceps of this embodiment, when the treatment portion is completely closed, the second jaw 81 comes into contact with only the insulating member 82 of the first jaw 80. That is, when the tissue is gripped by the jaws 80 and 81, the electrode portions to which a high-frequency current is supplied do not come into contact with each other. Hence, no electrical short circuit occurs between the jaws 8a and 8b, and even thin membranous tissue can be reliably coagulated or incised.

In the bipolar forceps of this embodiment, the insulating member 82 is sandwiched by the two electrode portions 83 and 84 of the first jaw 80, and the tissue is also gripped by this insulating member 82. Hence, the operator can reliably grip the tissue without missing it and coagulate/incise it.

In this embodiment, the three lines 89, 90, and 91 corresponding to the electrode portions 81, 83, and 84, respectively, are arranged in the high-frequency cautery power supply unit 69. Hence, the switch for switching between incision and coagulation need not be provided on the operation portion side of the bipolar forceps.

In this embodiment, since a large distance is ensured between the two coagulation electrode portions 83 and 84 by the insulating member 82, the coagulation range can be increased as compared to the seventh and eighth embodiments.

Figure 17:
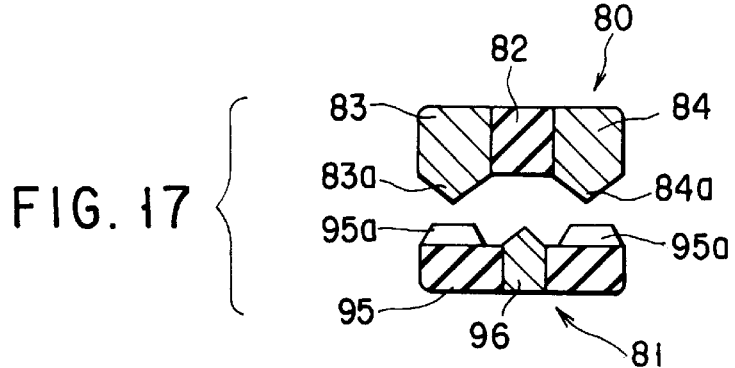
FIG. 17 is a sectional view of a treatment portion of a high-frequency treatment tool according to the 10th embodiment of the present invention.

FIG. 17 shows the 10th embodiment of the present invention. In a high-frequency treatment tool of this embodiment, the arrangement of a second jaw 81 is different from that in the ninth embodiment. More specifically, the second jaw 81 comprises a main body portion 95 consisting of a material having electrical insulating properties, and an electrode portion 96 consisting of a conductive material and arranged almost at the central portion of the main body portion 95 to substantially extend throughout the total length of the main body portion 95. Serrate gripping portions 95a meshing with gripping portions 83a and 84a of a first jaw 80 are formed on both sides of the main body portion 95. The arrangement of the remaining portions is the same as in the ninth embodiment.

According to this arrangement, since the second jaw 81 also has the gripping portions 95a, the tissue gripping area increases as compared to the ninth embodiment, so tissue can be reliably gripped.

Figure 18:
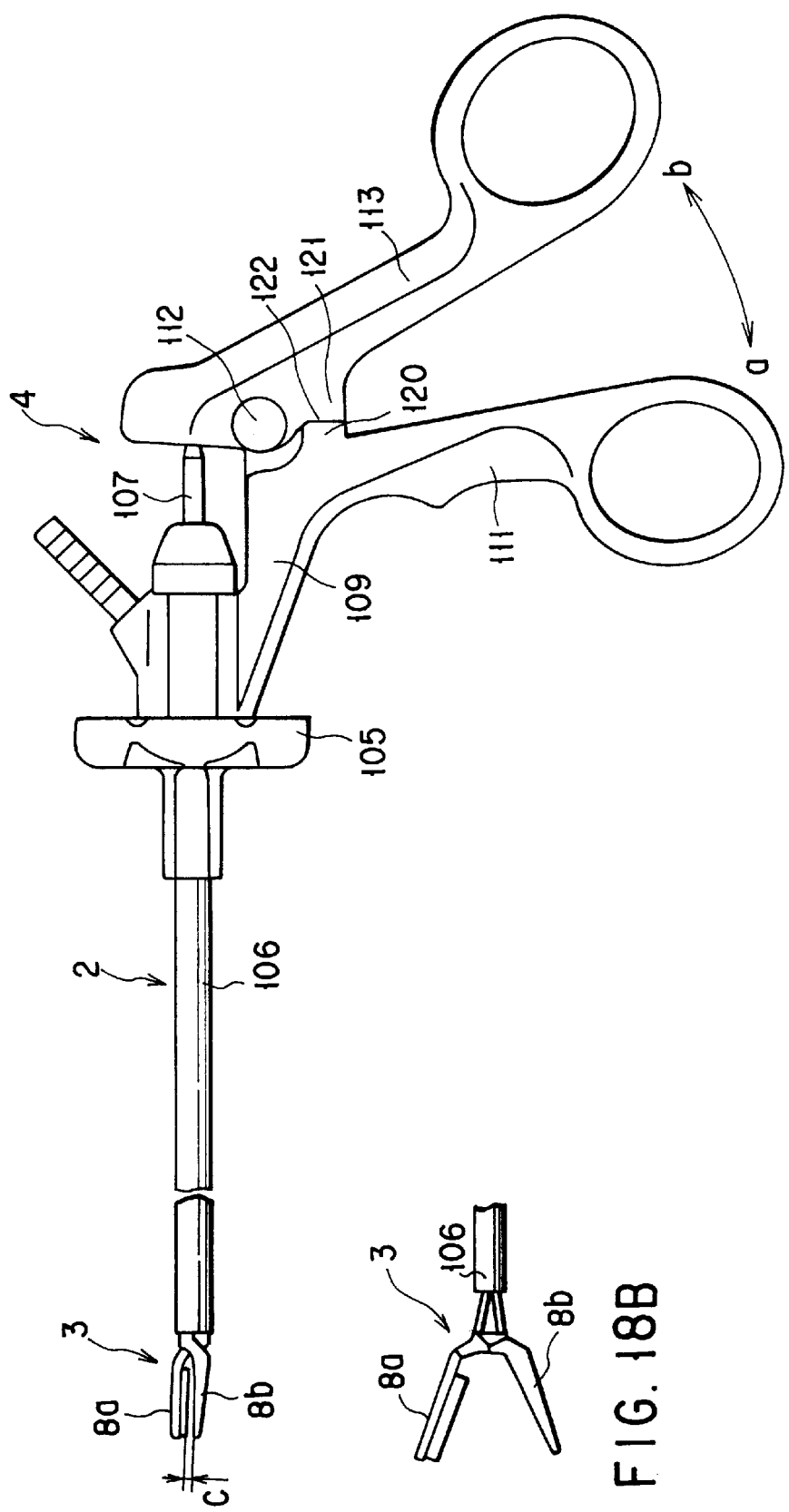
FIGS. 18A and 18B are side views of a high-frequency treatment tool according to the 11th embodiment of the present invention.

FIGS. 18A and 18B show the 11th embodiment of the present invention. A high-frequency treatment tool of this embodiment comprises a long insertion portion 2 to be inserted into the body cavity of a patient, a treatment portion 3 attached to the distal end portion of the insertion portion 2 to grip vital tissue and coagulate or incise it, and an operation portion 4 coupled to the proximal end portion of the insertion portion 2. The insertion portion 2 has a sheath 106 rotatably supported by a rotary operation portion 105 of the operation portion 4. A driving shaft 107 extending into the operation portion 4 is inserted into the sheath 106 to freely move back and forth. First and second jaws 8a and 8b as electrodes constituting the treatment portion 3 are fixed at the distal end portion of the driving shaft 107 while being biased in the opening direction. The operation portion 4 has a fixed handle 111 integrated with an operation portion main body 109 and a movable handle 113 attached to the operation portion main body 109 through a pivot pin 112 as a fulcrum to freely pivot. The proximal end portion of the driving shaft 107 is fixed to the movable handle 113. A projecting portion 120 is formed on a surface of the fixed handle 111 opposing the movable handle 113. The movable handle 113 has an abutment portion 121 which can abut against the projecting portion 120 when the movable handle 113 is pivoted to the fixed handle 111 side.

In this arrangement, when the movable handle 113 is pivoted in a direction b shown in FIG. 18A, i.e., in a direction in which the movable handle 113 is separated from the fixed handle 111, the driving shaft 107 is pushed forward by the movable handle 113, and the first and second jaws 8a and 8b project forward from the sheath 106. Hence, the first and second jaws 8a and 8b biased in the opening direction are separated from each other to open the treatment portion 3.

On the other hand, when the movable handle 113 is pivoted in a direction a shown in FIG. 18A, i.e., to the fixed handle 111 side, the driving shaft 107 is pulled back by the movable handle 113, so the proximal sides of the first and second jaws 8a and 8b are accommodated in the sheath 106. More specifically, the first and second jaws 8a and 8b biased in the opening direction are forcibly pressed by the inner wall of the sheath 106 in a direction in which the jaws 8a and 8b are close to each other to start to close the treatment portion 3. However, when the abutment portion 121 of the movable handle 113 abuts against the projecting portion 120 of the fixed handle 111 at a contact portion 122, the treatment portion 3 is not closed anymore, and a predetermined gap C is formed between the first jaw 8a and second jaw 8b. That is, when tissue is gripped, the conductive portions of the jaws 8a and 8b to which a high-frequency current is supplied do not come into contact with each other. Hence, when tissue is gripped by the jaws 8a and 8b, no electrical short circuit occurs between the jaws 8a and 8b. For this reason, even thin membranous tissue can be reliably coagulated or incised.

FIGS. 19 to 25 show the 12th embodiment of the present invention. As shown in FIG. 19, a bipolar forceps 201 as a high-frequency treatment tool of this embodiment comprises a sheath 202 as an insertion portion 2 to be inserted into the body cavity of a patient, a treatment portion 203 attached to the distal end portion of the sheath 202 to grip vital tissue and coagulate or incise it, and an operation portion 204 coupled to the proximal end portion of the sheath 202. The sheath 202 is rotated by operating a rotary operation portion 205 provided on the operation portion 204 side.

The treatment portion 203 has a pair of jaws 206 and 207 which can be opened/closed. The operation portion 204 comprises a fixed handle 208 and a movable handle 209. When the movable handle 209 is pivoted, the jaws 206 and 207 are opened/closed.

A conductive member as a high-frequency current supply path is electrically connected to the jaws 206 and 207 (more accurately, electrode portions to be described later). This conductive member extends through the sheath 202 and is connected to a connector receptacle 211 of the operation portion 204. A cable 212 extending from a high-frequency cautery power supply unit 213 is connected to the connector receptacle 211. The high-frequency cautery power supply unit 213 has a foot switch 214 for turning on/off the power supply unit 213. The foot switch 214 has an incision switch portion and a coagulation switch portion. The operation portion 204 has a change-over switch 210 for switching the high-frequency current to be supplied to the jaws 206 and 207 between incision and coagulation (switching between the incision current and the coagulation current).

As shown in FIG. 20 in detail, the first jaw 206 on one side of the treatment portion 203 has two electrode portions 220 and 222 electrically insulated from each other by an insulating member 221. More specifically, the insulating member 221 is arranged on both sides of the first electrode portion 220. The second electrode portion 222 sandwiches the insulating member 221 from both sides. That is, the first jaw 206 has a structure in which the electrode portions 220 and 222 and insulating member 221 are sequentially stacked in the direction of width.

The first electrode portion 220 inside the insulating member 221 functions as an incision electrode and projects in a chevron shape from the gripping surface of the insulating member 221. The second electrode portion 222 located outside the insulating member 221 functions as a coagulation electrode.

The second jaw 207 on the other side of the treatment portion 203 is formed as a third electrode portion consisting of a conductive material. The third electrode portion 207 has a flat gripping portion opposing the first and second electrode portions 220 and 222 and insulating member 221.

Figure 25:
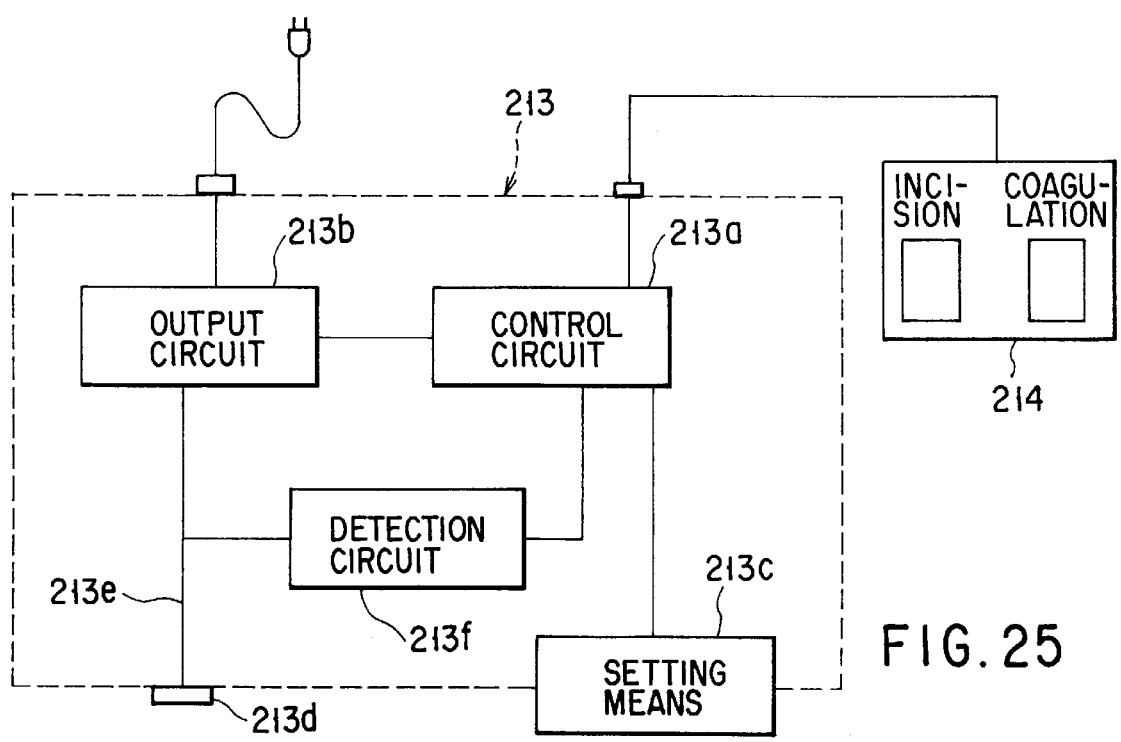
FIG. 25 is a block diagram showing the circuit arrangement of a power supply unit for supplying a high-frequency current.

The high-frequency cautery power supply unit 213 for supplying a high-frequency current to the electrode portions 207, 220, and 222 has an arrangement shown in FIG. 25. Referring to FIG. 25, reference numeral 213b denotes an output circuit for supplying a high-frequency current; 213a, a control circuit for controlling the high-frequency output from the output circuit 213b in accordance with a control signal from the foot switch 214; 213c, a setting means for inputting a predetermined output condition to the control circuit 213a as an electrical signal; 213d, an output connector connected to an electrical cable extending from the bipolar forceps; 213e, a high-frequency output line connecting the output circuit 213b to the output connector 213d; and 213f, a detection circuit for detecting the impedance of tissue from the high-frequency current flowing through the line 213e and sending a detection signal to the control circuit 213a.

Figure 22:
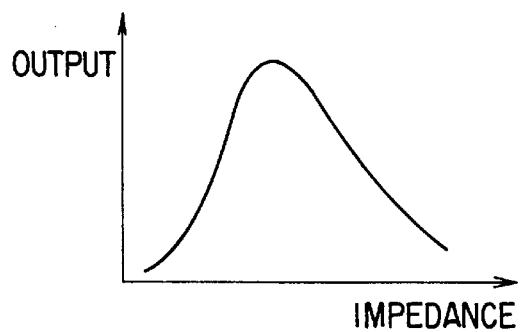
FIG. 22 is a graph showing the relationship between the high-frequency current output and the impedance of tissue upon coagulation output.

FIGS. 21A and 21B show steps of coagulating/incising vital tissue P using the jaws 206 and 207 having the above arrangement. FIG. 21A shows a state wherein the jaws 206 and 207 are closed to sandwich the vital tissue P between the jaws 206 and 207. At this time, the tissue P is gripped not only by the electrode portions 207, 220, and 222 but also by the insulating member 221. That is, the insulating member 221 between the electrode portions 220 and 222 prevents the tissue gripped by the electrode portions 207, 220, and 222 from escape. In this state, a second coagulation current is flowed across the second electrode portion 222 as a coagulation current and the third electrode portion 207 to coagulate the vial tissue P. The coagulation current is supplied from the output circuit 213b and has load characteristics representing that when the impedance of the vital tissue P increases upon coagulation, the output decreases, as shown in FIG. 22.

Figure 24:
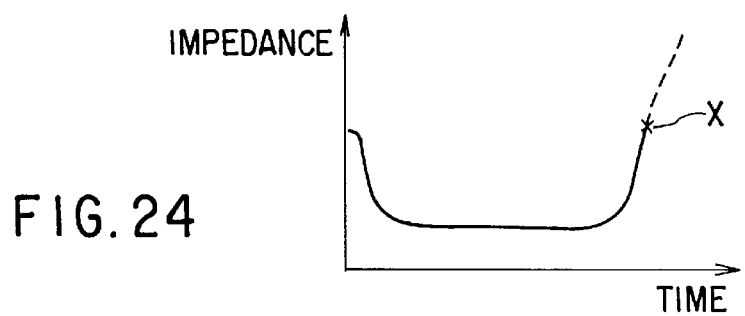
FIG. 24 is a graph showing a change in impedance of tissue upon coagulation output.

In outputting the coagulation current, the impedance of the vital tissue P changes over time, as shown in FIG. 24. This change in impedance of the vital tissue P is detected by the control circuit 213a through the detection circuit 213f. When the vital tissue P is completely coagulated (e.g., at a point X on the impedance curve shown in FIG. 24), the control circuit 213a stops outputting the coagulation current from the output circuit 213b.

In this embodiment, coagulation (output of the coagulation current) may be manually stopped using the foot switch 214. More specifically, an automatic mode in which coagulation is automatically stopped by the control circuit 213a and a manual mode in which output of the coagulation current is stopped not by the control circuit 213a but on the basis of operator's judgment can be selected by the setting means 213c. When the manual mode is selected by the setting means 213c, the operator is warned of the end of coagulation by a buzzer sound or the like at the time point when coagulation is completely performed (at the point X on the impedance curve shown in FIG. 24).

The control circuit 213a preferably allows incision output by the incision output operation of the foot switch 214 only after the coagulation output is performed by the coagulation output operation of the foot switch 214.

Figure 23:
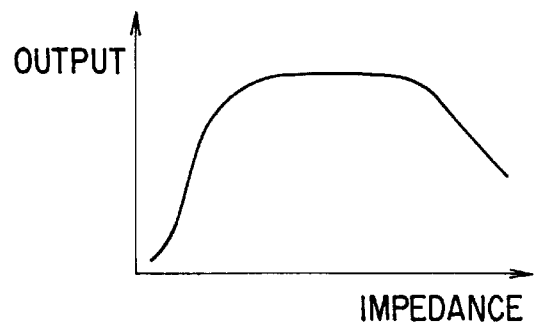
FIG. 23 is a graph showing the relationship between the high-frequency current output and the impedance of tissue upon incision output.

Upon completing coagulation, an incision current is flowed across the first electrode portion 220 as an incision electrode and the third electrode portion 207, as shown in FIG. 21B, to incise the vital tissue P. At this time, the contact area between the electrode portion 220 and the tissue is smaller than that between the electrode portion 222 and the tissue in coagulation. Hence, the tissue P after coagulation can be easily incised. FIG. 23 shows the output characteristics of the incision current.

As described above, in the bipolar forceps 201 of this embodiment, the insulating member 221 is inserted between the electrode portions 220 and 222 of the first jaw 206, so the tissue can also be gripped by the insulating member 221. Hence, the operator can reliably grip tissue without missing it and coagulate/incise it.

In this embodiment, when the automatic mode is selected by the setting means 213c, the coagulation current output is automatically stopped by the control circuit 213a at a time point when the vital tissue P is completely coagulated. When the manual mode is selected, the operator is warned of the end of coagulation by a buzzer sound or the like at a time point when coagulation is complete. That is, incision can be performed after the tissue is gripped and reliably coagulated. Hence, neither faulty coagulation nor bleeding during incision occurs. To the contrary, in a conventional bipolar forceps (scissors forceps) disclosed in, e.g., Jpn. Pat. Appln. KOKAI Publication No. 9-173347, incision can be performed by the operator's intention even when coagulation is incomplete, so bleeding may take place during incision.

In this embodiment as well, an electrical insulating portion may be formed on the gripping surface of at least one gripping portion (jaw 206 or 207), as in the first to fifth embodiments. In this case, a predetermined gap is formed between the gripping surfaces of the gripping portions when the gripping portions are completely closed to make the electrical insulating portion abut against the gripping surface of the other gripping portion, thereby preventing a short circuit between the electrode portions of the gripping portions. In addition, as in the sixth to 10th embodiments, an electrical insulating portion may be formed on the gripping surface of one gripping portion (jaw 206 or 207). In this case, a short circuit between the electrode portions of the gripping portions is prevented when the gripping portions are completely closed to bring the gripping surface of the other gripping portion into contact with only the electrical insulating portion. Furthermore, as in the 11th embodiment, an abutment portion 121 may be formed on the movable handle 209, and a projecting portion 120 may be formed on the fixed handle 208. When the projecting portion 120 abuts against the abutment portion 121, the treatment portion 203 is not closed anymore, and a predetermined gap C is formed between the first jaw 206 and the second jaw 207.

Figures 26, 27:
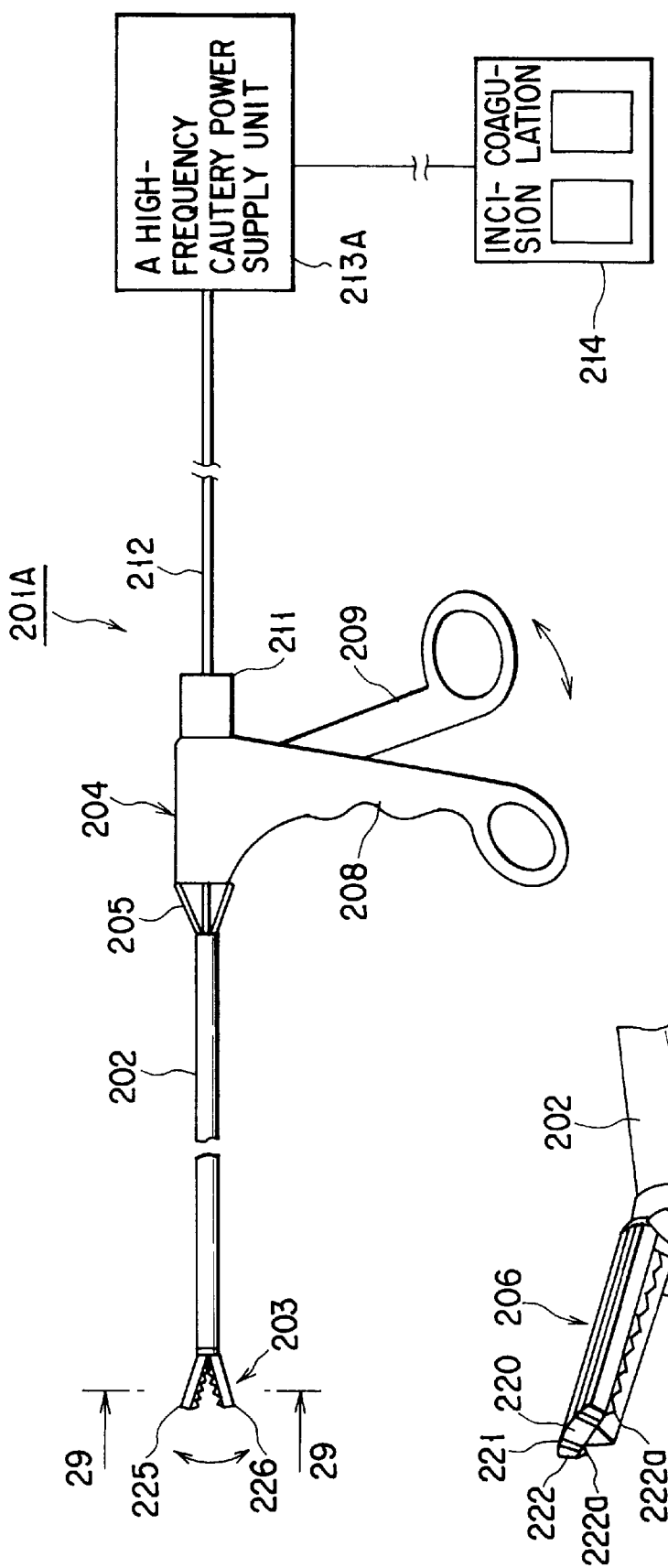
FIG. 26 is a perspective view of the distal end portion of a high-frequency treatment tool according to a modification of the 12th embodiment.
FIG. 27 is a side view of a high-frequency treatment tool according to the 13th embodiment of the present invention.

FIG. 26 shows a modification of the 12th embodiment. On both sides of the first jaw 206, serrate gripping portions 222a are formed almost across the total length of the first jaw 206 in the longitudinal direction. The gripping portions 222a are formed on the electrode portion 222 as a coagulation electrode. On both sides of the second jaw 207 as well, serrate gripping portions 207a meshing with the gripping portions 222a are formed almost across the total length of the second jaw 207 in the longitudinal direction. The arrangement of the remaining portions is the same as in the 12th embodiment.

FIGS. 27 to 30B show the 13th embodiment of the present invention. The same reference numerals as in the 12th embodiment denote the same parts in the 13th embodiment, and a detailed description thereof will be omitted. As shown in FIG. 27, a bipolar forceps 201A as a high-frequency treatment tool of this embodiment comprises a sheath 202, a treatment portion 203, and an operation portion 204. The treatment portion 203 comprises a pair of jaws 225 and 226 which can be opened/closed.

Figure 29:
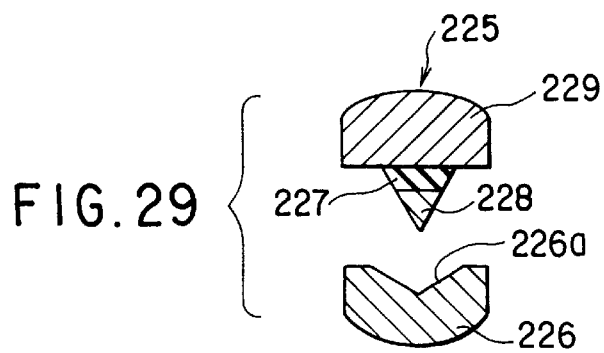
FIG. 29 is a sectional view taken along a line 29—29 in FIG. 27.

As shown in FIG. 29 in detail, the first jaw 225 on one side of the treatment portion 203 has two electrode portions 228 and 229 electrically insulated from each other by an insulating member 227. More specifically, the insulating member 227 is arranged on the upper surface of the first electrode portion 228, and the second electrode portion 229 wider than the insulating member 227 and first electrode portion 228 is arranged on the upper surface of the insulating member 227. That is, the first jaw 225 has a structure in which the electrode portions 228 and 229 and insulating member 227 are sequentially stacked in the direction of height.

The first electrode portion 228 on the lower side of the insulating member 227 functions as an incision electrode and is tapered downward together with the insulating member 227. The second electrode portion 229 on the upper side of the insulating member 227 functions as a coagulation electrode.

The second jaw 226 on the other side of the treatment portion 203 is formed as a third electrode portion consisting of a conductive material. A V-shaped mesh groove 226a which can engage with the insulating member 227 and first electrode portion 228 is formed in the gripping surface of the third electrode portion 226 in the longitudinal direction of the electrode portion 226.

Figure 28:
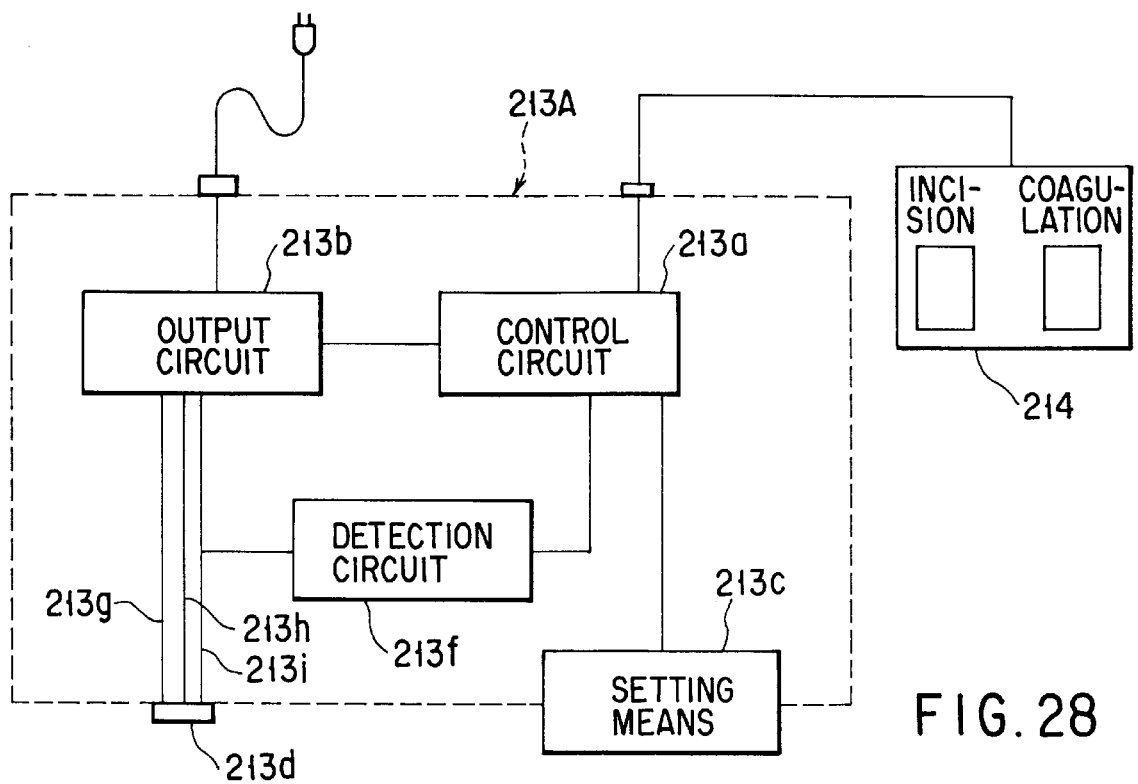
FIG. 28 is a block diagram showing the circuit arrangement of a power supply unit for supplying a high-frequency current.

A high-frequency cautery power supply unit 213A for supplying a high-frequency current to the electrode portions 226, 228, and 229 has an arrangement shown in FIG. 28. Referring to FIG. 28, reference numeral 213b denotes an output circuit for supplying a high-frequency current; 213a, a control circuit for controlling the high-frequency output from the output circuit 213b in accordance with a control signal from a foot switch 214; 213c, a setting means for inputting a predetermined output condition to the control circuit 213a as an electrical signal; 213d, an output connector connected to an electrical cable extending from the bipolar forceps 201A; 213g, 213h, and 213i, lines connecting the output circuit 213b to the output connector 213d and electrically connected to the electrode portions 226, 228, and 229, respectively; and 213f, a detection circuit for detecting the impedance of tissue from the high-frequency current flowing through the lines 213g, 213h, and 213i and sending a detection signal to the control circuit 213a.

Figure 30A:
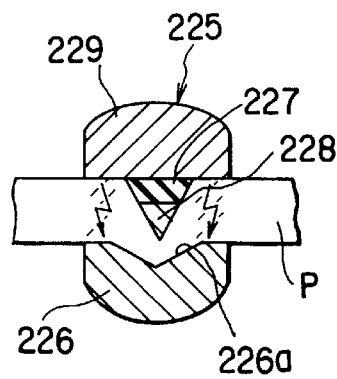
FIGS. 30A and 30B are sectional views showing a use form of the high-frequency treatment tool shown in FIG. 27.
Figure 30B:
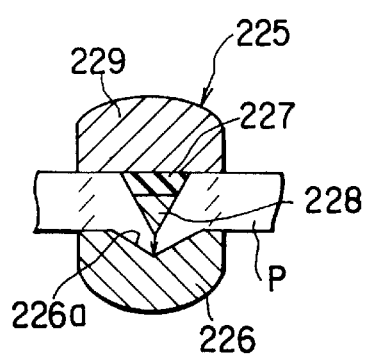

FIGS. 30A and 30B show steps of coagulating/incising vital tissue P using the jaws 225 and 226 having the above arrangement. FIG. 30A shows a state wherein the jaws 225 and 226 are closed to sandwich the vital tissue P between the jaws 225 and 226. At this time, the tissue P is gripped not only by the electrode portions 226, 228, and 229 but also by the insulating member 227. That is, the insulating member 227 and first electrode portion 228 move to mesh with the groove 226a of the third electrode portion 226, and the tissue P is sandwiched by the electrode portions 226, 228, and 229 and insulating member 227 to be pressed into the groove 226a and reliably gripped. In this state, a coagulation current is flowed across the second electrode portion 229 and the third electrode portion 226 to coagulate the vital tissue P.

In outputting the coagulation current, a change in impedance of the tissue P is detected by the control circuit 213a through the detection circuit 213f, as in the 12th embodiment. When the vital tissue P is completely coagulated (e.g., at a point X on the impedance curve shown in FIG. 24), the control circuit 213a stops outputting the coagulation current from the output circuit 213b. When a manual mode is selected by the setting means 213c, the operator is warned of the end of coagulation by a buzzer sound or the like at the time point when coagulation is completely performed (at the point X on the impedance curve shown in FIG. 24).

Upon completing coagulation, an incision current is flowed across the first electrode portion 228 as an incision electrode and the third electrode portion 226, as shown in FIG. 30B, to incise the vital tissue P.

As described above, in the bipolar forceps 201A, the insulating member 227 is inserted between the electrode portions 228 and 229 of the first jaw 225, so the tissue can also be gripped by the insulating member 227. Hence, the operator can reliably grip and coagulate/incise the tissue without missing it.

In this embodiment, when the automatic mode is selected by the setting means 213c, the coagulation current output is automatically stopped by the control circuit 213a at a time point when the vital tissue P is completely coagulated. When the manual mode is selected, the operator is warned of the end of coagulation by a buzzer sound or the like at a time point when coagulation is complete. That is, incision can be performed after the tissue is gripped and reliably coagulated. Hence, neither faulty coagulation nor bleeding during incision occurs.

In this embodiment as well, an electrical insulating portion may be formed on the gripping surface of at least one gripping portion (jaw 225 or 226), as in the first to fifth embodiments. In this case, a predetermined gap is formed between the gripping surfaces of the gripping portions when the gripping portions are completely closed to make the electrical insulating portion abut against the gripping surface of the other gripping portion, thereby preventing a short circuit between the electrode portions of the gripping portions. In addition, as in the sixth to 10th embodiments, an electrical insulating portion may be formed on the gripping surface of one gripping portion (jaw 225 or 226). In this case, a short circuit between the electrode portions of the gripping portions is prevented when the gripping portions are completely closed to bring the gripping surface of the other gripping portion into contact with only the electrical insulating portion. Furthermore, as in the 11th embodiment, an abutment portion 121 may be formed on a movable handle 209, and a projecting portion 120 may be formed on a fixed handle 208. When the projecting portion 120 abuts against the abutment portion 121, the treatment portion 203 is not closed anymore, and a predetermined gap C is formed between the first jaw 225 and the second jaw 226.

Figures 31A, 31B:
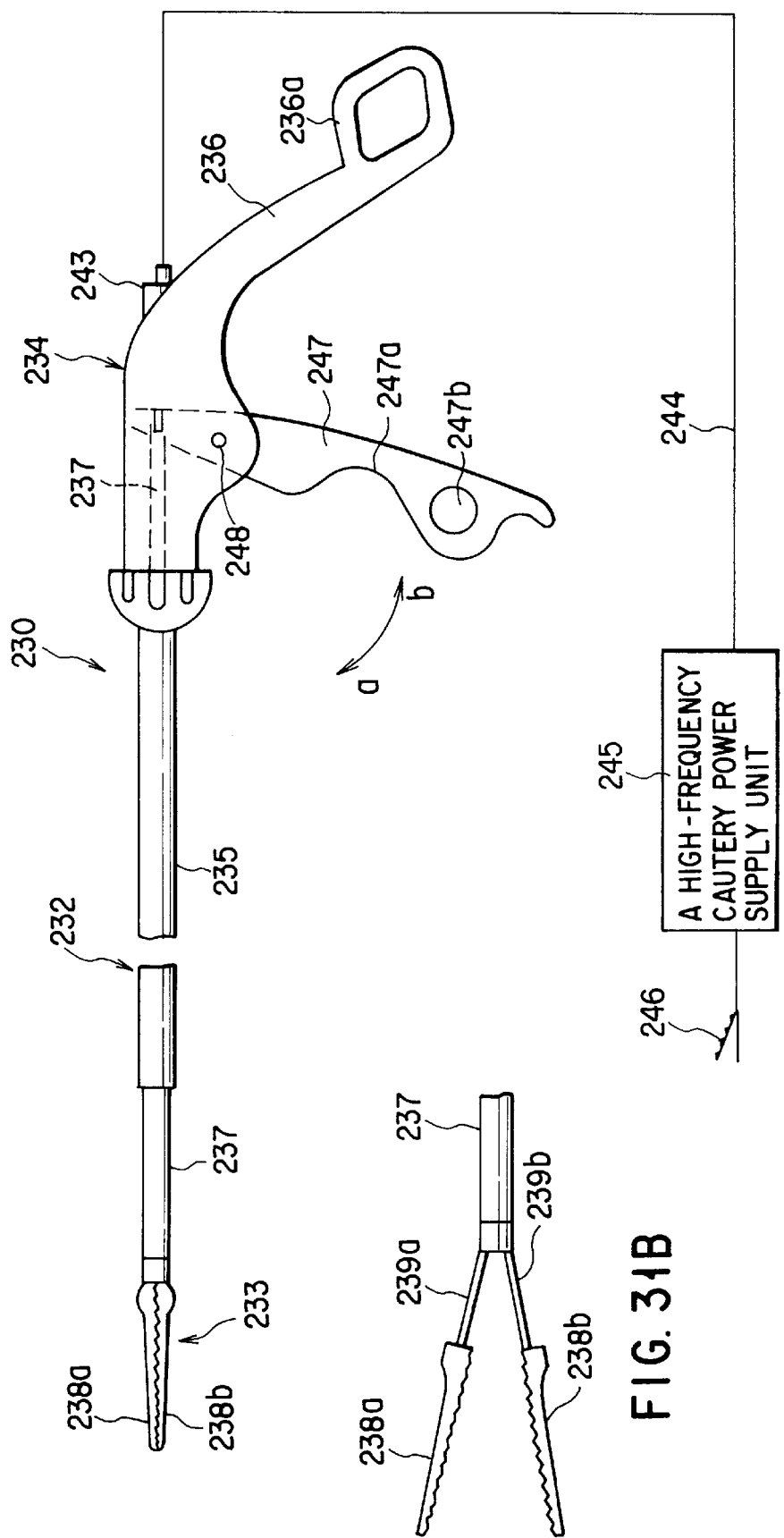
FIG. 31A is a side view of a high-frequency treatment tool according to the 14th embodiment of the present invention in the closed state.
FIG. 31B is a side view of the high-frequency treatment tool shown in FIG. 31A in the open state.

FIGS. 31A to 34B show the 14th embodiment of the present invention. As shown in FIGS. 31A and 31B, a bipolar forceps 230 as a high-frequency treatment tool of this embodiment comprises a long insertion portion 232 to be inserted into the body cavity of a patient, a treatment portion 233 attached to the distal end portion of the insertion portion 232 to grip vital tissue and coagulate or incise it, and an operation portion 234 coupled to the proximal end portion of the insertion portion 232.

The operation portion 234 has a grip 236 which can be gripped with a hand. The grip 236 has a finger hook portion 236a on which the operator places the thumb. The grip 236 also has a trigger 247 as a forceps operation means. This trigger 247 is pivotally coupled to the upper end portion of the grip 236 through a pivot pin 248. The trigger 247 has finger hook portions 247a and 247b on which the operator places the index and middle fingers, respectively.

The operation portion 234 has a connector receptacle 243. A cable 244 extending from a high-frequency cautery power supply unit 245 is connected to the connector receptacle 243. The high-frequency cautery power supply unit 245 has a foot switch 246 for turning on/off the power supply unit 245.

The insertion portion 232 is comprised of a rotatable outer sheath 235 and an inner sheath 237 inserted in the outer sheath 235 to move back and forth. The inner sheath 237 is inserted into the grip 236 of the operation portion 234. The proximal end portion of the inner sheath 237 is coupled to the trigger 247.

A holding member having electrical insulating properties is fitted in the inner sheath 237. A pair of elastic members 239a and 239b are stationarily held by the holding member. The elastic members 239a and 239b are comprised of conductive rods formed from a spring steel or the like. Each conductive rod is covered with an insulating tube. The proximal end portions of the conductive rods of the elastic members 239a and 239b are connected to the connector receptacle 243 of the operation portion 234, and the distal end portions project from the distal end of the inner sheath 237. The elastic members 239a and 239b have jaws 238a and 238b forming the treatment portion 233 at their distal ends, respectively, and always bias the jaws 238a and 238b in the opening direction.

In this arrangement, when the trigger 247 is pulled to the grip 236 side (in a direction b in FIG. 31A), the inner sheath 237 moves forward in the axial direction, and the elastic members 239a and 239b are relatively retracted into the inner sheath 237 (FIG. 31A). At this time, the elastic members 239a and 239b are pressed inward by the inner wall of the inner sheath 237 to close the jaws 238a and 238b. On the other hand, when the trigger 247 is pivoted and separated from the grip 236 (in a direction a in FIG. 31A), the elastic members 239a and 239b relatively project from the inner sheath 237, so the jaws 238a and 238b are opened by the restoring force of the elastic members 239a and 239b (FIG. 31B).

Figure 32A:
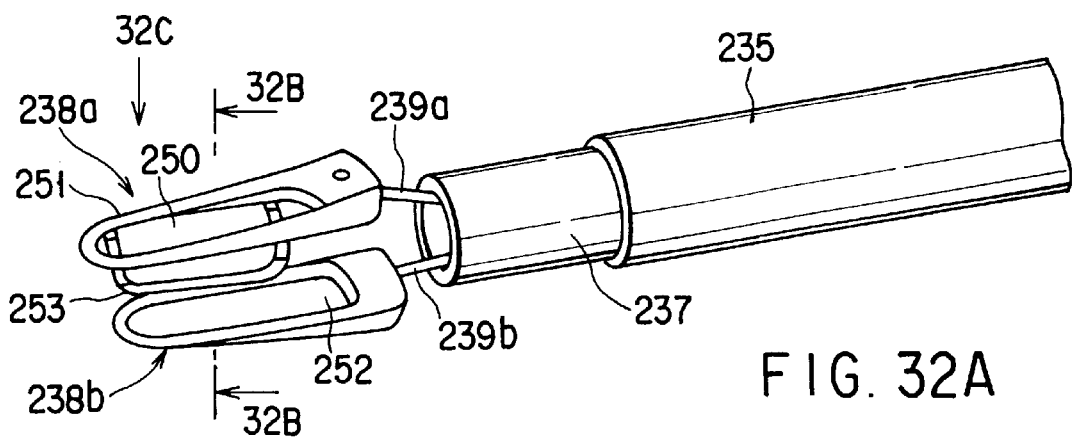
FIG. 32A is a perspective view of the distal end side of the high-frequency treatment tool shown in FIG. 31A.
Figure 32B:
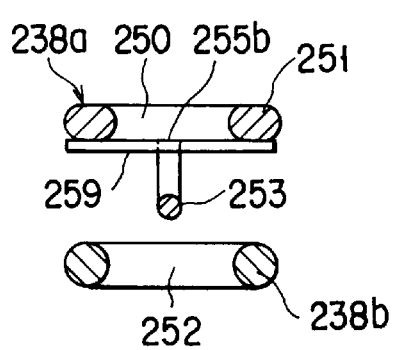
FIG. 32B is a sectional view taken along a line 32B—32B in FIG. 32A.
Figure 32C:
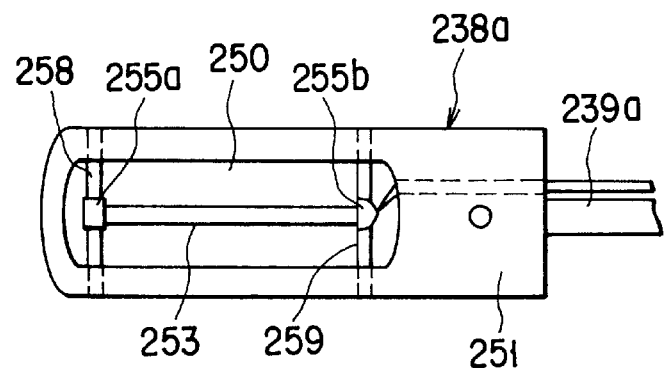
FIG. 32C is a view shown in a direction indicated by an arrow 32C in FIG. 32A.

As shown in FIGS. 32A to 32C in detail, the second jaw 238b at the distal end of the elastic member 239b is formed as the first electrode portion made of a conductive material. The first electrode portion 238b has an opening 252 extending in the longitudinal direction and therefore has a substantially loop shape.

The first jaw 238a at the distal end of the elastic member 239a has a second electrode portion 251 made of a conductive material and functioning as an incision electrode. The second electrode portion 251 has an opening 250 extending in the longitudinal direction and therefore has a substantially loop shape (almost the same shape as the first electrode portion 238b). A pair of support members 258 and 259 are stretched across the opening 250 of the second electrode portion 251. A third wire electrode portion 253 is stretched between the support members 258 and 259 through insulating members 255a, 255b. The third wire electrode portion 253 functioning as an incision electrode extends in the longitudinal direction of the second electrode portion 251 at almost the central position of the second electrode portion 251, project downward in a U shape from the gripping surface of the second electrode portion 251, and enters the opening 252 of the first electrode portion 238b (or extends through the opening 252) when the jaws 238a and 238b are closed.

The third electrode portion 253 is positioned inside the second electrode portion 251, as described above, to prevent tissue which is not coagulated by the second electrode portion 251 from being incised by the third electrode portion 253.

The electrode portions 238b, 251, and 253 are connected to the connector receptacle 243 of the operation portion 234 through the conductive rods of the elastic members 239a and 239b. A high-frequency current is supplied from the high-frequency cautery power supply unit 245 to these electrode portions through the cable 244.

Figure 33A:
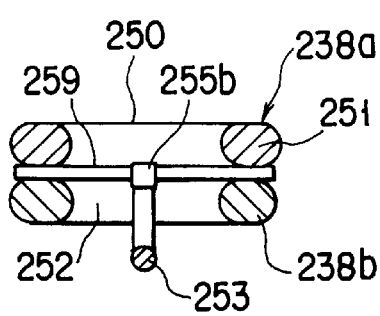
FIG. 33A is a sectional view of a treatment portion of the high-frequency current shown in FIG. 31A in the closed state.
Figure 33B:
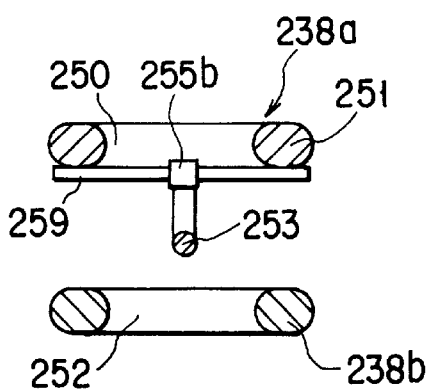
FIG. 33B is a sectional view of the treatment portion of the high-frequency current shown in FIG. 31A in the open state.

FIGS. 34A and 34B show steps of coagulating/incising vital tissue P using the jaws 238a and 238b having the above arrangement. FIG. 34A shows a state wherein the jaws 238a and 238b are opened, as shown in FIG. 33B, to insert the vital tissue P between the jaws 238a and 238b, and then, the jaws 238a and 238b are closed to sandwich the vital tissue P between the jaws 238a and 238b. When the third electrode portion 253 enters the opening 252 of the first electrode portion 238b, the tissue P is pressed against the first electrode portion 238b and reliably sandwiched and gripped by the jaws 238a and 238b. In this state, a coagulation current is flowed across the second electrode portion 251 as the coagulation electrode and the first electrode portion 238b to coagulate the vital tissue P.

Upon completing coagulation, the jaws 238a and 238b are further tightly closed, as shown in FIG. 34B, and an incision current is flowed across the third electrode portion 253 as the incision electrode and the first electrode portion 238b to incise the vital tissue P. At this time, since the third electrode portion 253 is a wire electrode portion, the contact area between the third electrode portion 253 and the tissue P is smaller than that between the electrode portion 251 and the tissue P in coagulation. Hence, the tissue P after coagulation can be easily incised.

As described above, the bipolar forceps 230 of this embodiment has the wire electrode portion 253 for incision, which projects downward in a U shape from the gripping surface of the first jaw 238a. When the wire electrode portion 253 enters the opening 252 of the second jaw 238b, the tissue can be sandwiched and gripped. Hence, the operator can reliably grip the tissue without missing it and incise/coagulate it.

In this embodiment as well, an electrical insulating portion may be formed on the gripping surface of at least one gripping portion (jaw 238a or 238b), as in the first to fifth embodiments. In this case, a predetermined gap is formed between the gripping surfaces of the gripping portions when the gripping portions are completely closed to make the electrical insulating portion abut against the gripping surface of the other gripping portion, thereby preventing a short circuit between the electrode portions of the gripping portions. In addition, as in the sixth to 10th embodiments, an electrical insulating portion may be formed on the gripping surface of one gripping portion (jaw 238a or 238b). In this case, a short circuit between the electrode portions of the gripping portions is prevented when the gripping portions are completely closed to bring the gripping surface of the other gripping portion into contact with only the electrical insulating portion. Furthermore, as in the 11th embodiment, an abutment portion 121 may be formed on the trigger 247, and a projecting portion 120 may be formed on the grip 236. When the projecting portion 120 abuts against the abutment portion 121, the treatment portion 233 is not closed anymore, and a predetermined gap C is formed between the first jaw 238a and the second jaw 238b.

FIGS. 35A and 35B show the first modification of the 14th embodiment. In the first jaw 238a, the third electrode portion 253 is directly attached to the second electrode portion 251 without interposing the support members 258 and 259. In this case, the third electrode portion 253 is electrically insulated from the second electrode portion 251 by an insulating member 255c. To prevent tissue which is not coagulated by the second electrode portion 251 from being incised by the third electrode portion 253, the third electrode portion 253 is bent at its connection portion to the second electrode portion 251. The arrangement of the remaining portions is the same as in the 14th embodiment.

FIGS. 36A and 36B show the second modification of the 14th embodiment. In the first jaw 238a, the third electrode portion 253 is attached to the second electrode portion 251 through an insulating member 255d having a T-shaped section and fitted in the opening 250 of the second electrode portion 251. The arrangement of the remaining portions is the same as in the 14th embodiment.

Figure 37A:
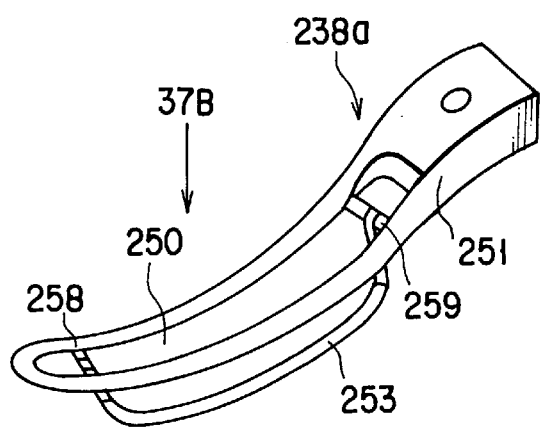
FIG. 37A is a perspective view showing the third modification of the treatment portion of the high-frequency treatment tool shown in FIG. 31A.
Figure 37B:
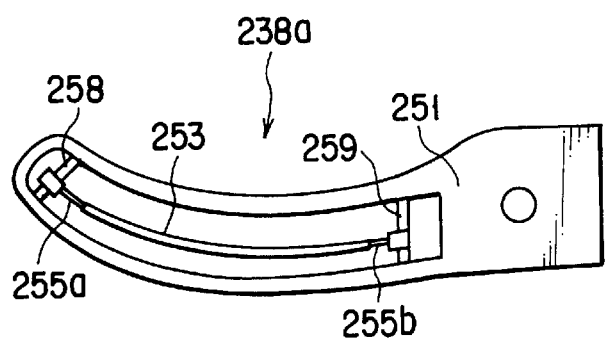
FIG. 37B is a view seen from a direction indicated by an arrow 37B in FIG. 37A.

FIGS. 37A and 37B show the third modification of the 14th embodiment. The first and second jaws 238a and 238b (FIGS. 37A and 38B show only the first jaw 238a) are formed as a Kelly clamp portion curved to one side. The arrangement of the remaining portions is the same as in the 14th embodiment.

Figure 38:
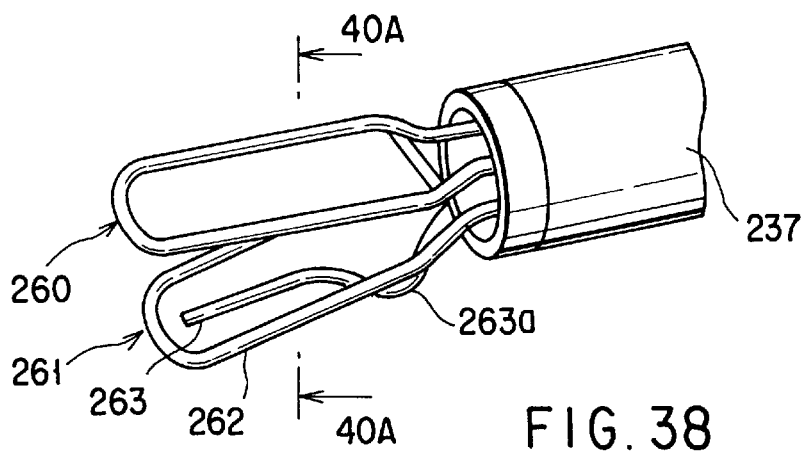
FIG. 38 is a perspective view of the treatment portion of a high-frequency treatment tool according to the 15th embodiment of the present invention.

FIGS. 38 to 41C show the 15th embodiment of the present invention. As shown in FIG. 38, a high-frequency treatment tool of this embodiment has a pair of jaws 260 and 261 for gripping vital tissue to coagulate or incise it. The jaws 260 and 261 are opened/closed by the same mechanism as in the 14th embodiment. The arrangements of an insertion portion and operation portion for gripping the jaws 260 and 261 are also the same as those of the insertion portion and operation portion of the 14th embodiment. The same reference numerals as in the 14th embodiment denote the same parts in the 15th embodiment, and a detailed description thereof will be omitted.

The first jaw 260 is formed as the first electrode portion having a loop shape and comprised of a conductive member. The second jaw 261 has a second electrode portion 262 having a loop shape and comprised of a conductive member, and a third wire electrode portion 263 having elasticity. The second electrode portion 262 functions as a coagulation electrode, and the third electrode portion 263 functions as an incision electrode.

Figure 39A:
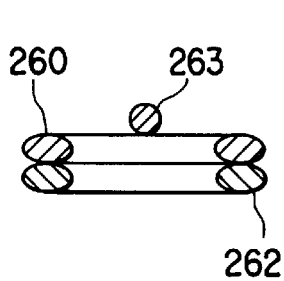
FIG. 39A is a sectional view of the treatment portion of the high-frequency treatment tool shown in FIG. 38 in the closed state.
Figure 39B:
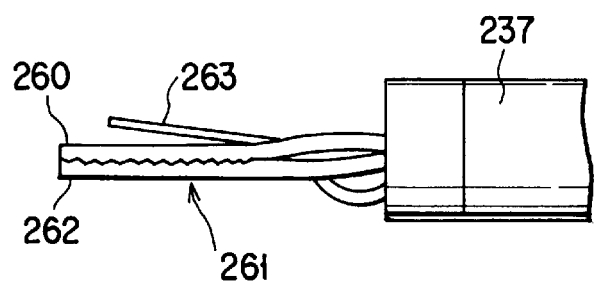
FIG. 39B is a side view of the treatment portion of the high-frequency treatment tool shown in FIG. 38 in the closed state.
Figure 40A:
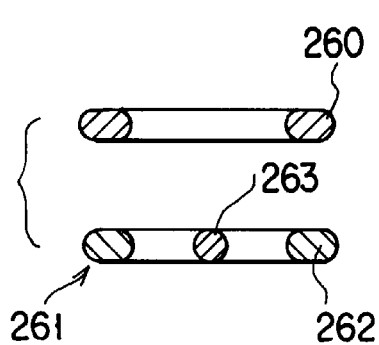
FIG. 40A is a sectional view showing the treatment portion taken along a line 40A—40A in FIG. 38 in the open state.
Figure 40B:
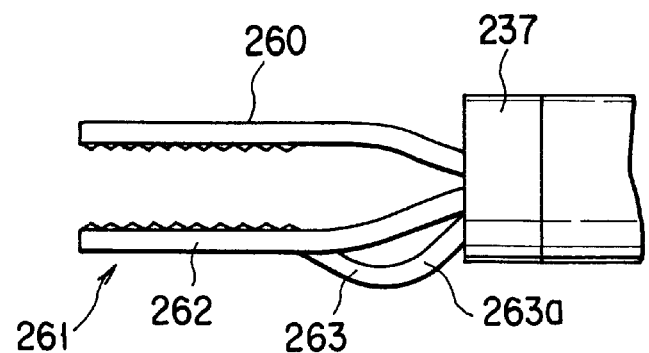
FIG. 40B is a side view of the treatment portion of the high-frequency treatment tool shown in FIG. 38 in the open state.

When an inner sheath 237 is retreated to the hand side to open the jaws 260 and 261 as shown in FIGS. 38 and 40A (FIG. 40B), the third wire electrode portion 263 projects and is bent outward from the distal end of the inner sheath 237 beyond the outer diameter of the sheath 237 almost at the central portion in the second electrode portion 262 and extends toward the opening of the second electrode portion 262 while the distal end side horizontally extends within the opening of the second electrode portion 262. When the inner sheath 237 moves forward to close the jaws 260 and 261, a bent portion 263a of the third electrode portion 263, which projects beyond the outer diameter of the sheath 237, is retracted into the sheath 237 and pressed against the inner wall of the sheath 237, as shown in FIGS. 39A and 39B. With this operation, the distal end side is biased inward to project from the opening of the first electrode portion 260.

The electrode portions 260, 262, and 263 are connected to a connector receptacle 243 of an operation portion 234 through the conductive rods of elastic members 239a and 239b. A high-frequency current is supplied from a high-frequency cautery power supply unit 245 to the electrode portions through a cable 244.

Figure 41A:
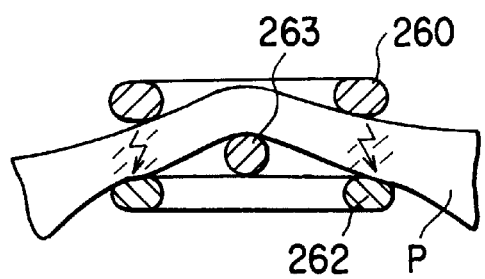
FIGS. 41A to 41C are sectional views showing a use form of the high-frequency treatment tool shown in FIG. 38.
Figure 41B:
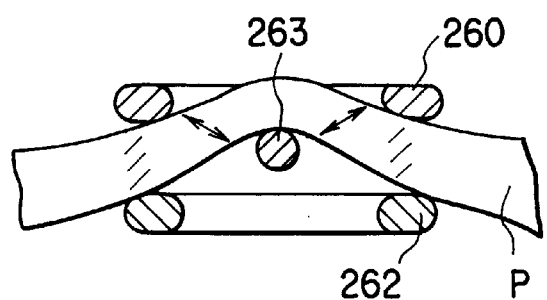
Figure 41C:
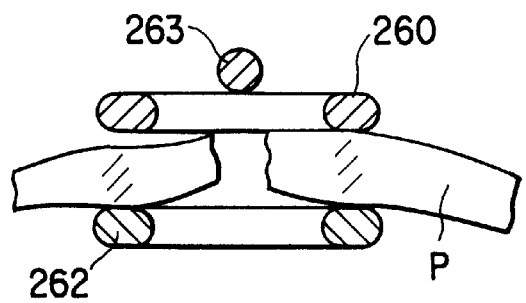

FIGS. 41A to 41C show steps of coagulating/incising vital tissue P using the jaws 260 and 261 having the above arrangement. FIG. 41A shows a state wherein the sheath 237 is moved forward to close the jaws 260 and 261 and sandwich the vital tissue P between the jaws 260 and 261. At this time, the bent portion 263a of the third electrode portion 263 is retracted into the sheath 237 and biased inward by the sheath 237, so the tissue P is pressed against the first electrode portion 260 by the distal end portion projecting from the opening of the second electrode portion 262. That is, the tissue P is sandwiched by the jaws 260 and 261 while being pushed into the opening of the first electrode portion 260 by the third electrode portion 263. In this state, a coagulation current is flowed across the second electrode portion 262 as a coagulation electrode and the first electrode portion 260 to coagulate the tissue P.

Upon completing coagulation, the jaws 260 and 261 are further tightly closed, as shown in FIG. 41B, and an incision current is flowed across the third electrode portion 263 as an incision electrode and the first electrode portion 260 to incise the vital tissue P. In this case, since the third electrode portion 263 is a wire electrode portion, the contact area between the third electrode portion 263 and the tissue P is smaller than that between the electrode portion 262 and the tissue P in coagulation. In addition, the third electrode portion 263 is biased by the sheath 237 in a direction for incising the tissue P. Hence, when the biased third electrode portion 263 projects from the opening of the first electrode portion 260, the tissue P after coagulation can be easily incised without particularly tightly gripping the tissue P for incision.

As described above, the high-frequency treatment tool of this embodiment has the wire electrode portion 263 for incision, which is biased in a direction for incising the tissue. By the function of the wire electrode portion 263, the tissue can be sandwiched and gripped by the jaws 260 and 261. Hence, the operator can reliably grip the tissue without missing it and coagulate/incise it. In addition, since the tissue is incised by moving the electrode portion 263 biased in the incision direction, incision can be reliably performed. Since the incision state can be confirmed by moving the electrode portion 263, excess power need not be supplied during incision (excess incision current need not be supplied), and burning of tissue to the incision electrode 263 can be minimized.

Figures 42A, 42B:
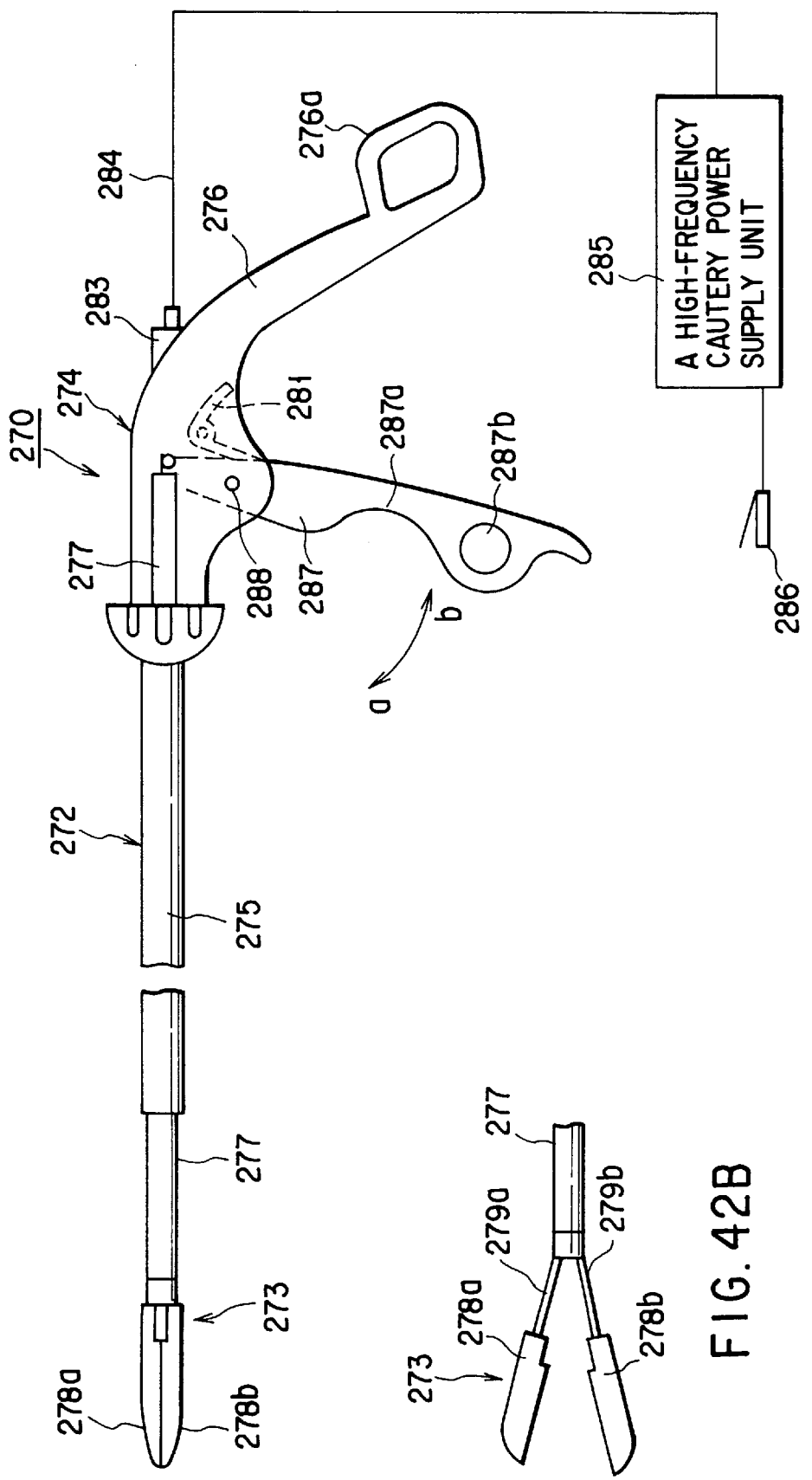
FIG. 42A is a side view of a high-frequency treatment tool according to the 16th embodiment of the present invention in the closed state.
FIG. 42B is a side view of the high-frequency treatment tool shown in FIG. 42A in the open state.

FIGS. 42A and 42B show the 16th embodiment of the present invention. As shown in FIGS. 42A and 42B, a bipolar forceps 270 as a high-frequency treatment tool of this embodiment comprises a long insertion portion 272 to be inserted into the body cavity of a patient, a treatment portion 273 attached to the distal end portion of the insertion portion 272 to grip vital tissue and coagulate or incise it, and an operation portion 274 coupled to the proximal end portion of the insertion portion 272.

The operation portion 274 has a grip 276 which can be gripped with a hand. The grip 276 has a finger hook portion 276a on which the operator places the thumb. The grip 276 also has a trigger 287 as a forceps operation means. This trigger 287 is pivotally coupled to the upper end portion of the grip 276 through a pivot pin 288. The trigger 287 has finger hook portions 287a and 287b on which the operator places the index and middle fingers, respectively.

The operation portion 274 has a connector receptacle 283. A cable 284 extending from a high-frequency cautery power supply unit 285 is connected to the connector receptacle 283. The high-frequency cautery power supply unit 285 has a foot switch 286 for turning on/off the power supply unit 285.

The insertion portion 272 is comprised of a rotatable outer sheath 275 and an inner sheath 277 inserted in the outer sheath 275 to move back and forth. The inner sheath 277 is inserted into the grip 276 of the operation portion 274. The proximal end portion of the inner sheath 277 is coupled to the trigger 287.

A holding member having electrical insulating properties is fitted in the inner sheath 277. A pair of elastic members 279a and 279b are stationarily held by the holding member. The elastic members 279a and 279b are comprised of conductive rods formed from a spring steel or the like. Each conductive rod is covered with an insulating tube. The proximal end portions of the conductive rods of the elastic members 279a and 279b are connected to the connector receptacle 283 of the operation portion 274, and the distal end portions project from the distal end of the inner sheath 277. The elastic members 279a and 279b have jaws 278a and 278b forming the treatment portion 273 at their distal ends, respectively, and always bias the jaws 278a and 278b in the opening direction.

The grip 276 has a spring 281 for biasing the trigger 287 in a direction in which the trigger 287 is separated from the grip 276. The first and second jaws 278a and 278b have the same arrangement as that of the gripping members 50 and 51 of the sixth embodiment.

In this arrangement, when the trigger 287 is pulled to the grip 276 side (in a direction b in FIG. 42A) against the biasing force of the spring 281, the inner sheath 277 moves forward in the axial direction, and the elastic members 279*a* and 279*b* are relatively retracted into the inner sheath 277 (FIG. 42A). The elastic members 279*a* and 279*b* are pressed inward by the inner wall of the inner sheath 277 to close the jaws 278*a* and 278*b*. On the other hand, when the grasping force of the trigger 287 is loosened, the trigger 287 is pivoted by the biasing force of the spring 281 in a direction in which the trigger 287 separates from the grip 276 (in a direction a in FIG. 42A). The elastic members 279*a* and 279*b* relatively project from the inner sheath 277, and the jaws 278*a* and 278*b* are opened due to the restoring force of the elastic members 279*a* and 279*b* (FIG. 42B).

According to the arrangement of this embodiment, the same function and effect as in the sixth embodiment can be obtained. In this embodiment, even when the operator grips the trigger 287 of the operation portion, the electrode portions do not short-circuit, so proper coagulation and incision can be performed. In addition, since the operation force of the trigger 287 need not be finely adjusted, the operability is good. Furthermore, in this embodiment, when the grasping force of the trigger 287 is loosened, the jaws 278*a* and 278*b* are opened by the action using the biasing force of the spring 281 to ensure a distance allowing arc discharge between a third electrode portion 294 for incision and tissue P. Hence, incision can be reliably performed.

Figure 43A:
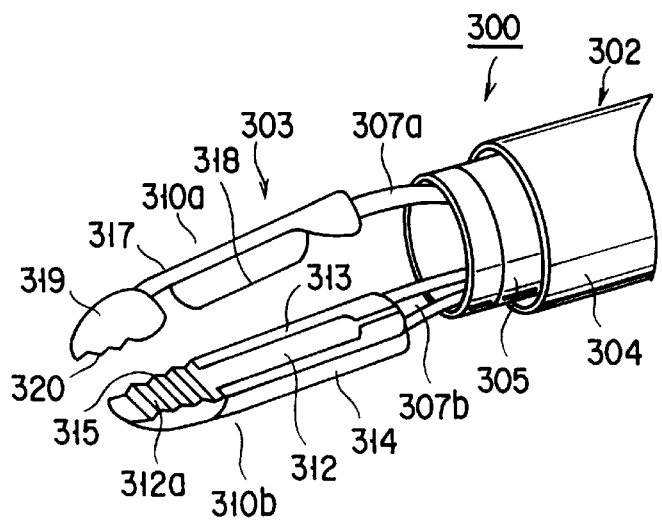
FIG. 43A is a perspective view of the treatment portion of a high-frequency treatment tool according to the 17th embodiment of the present invention.
Figure 43B:
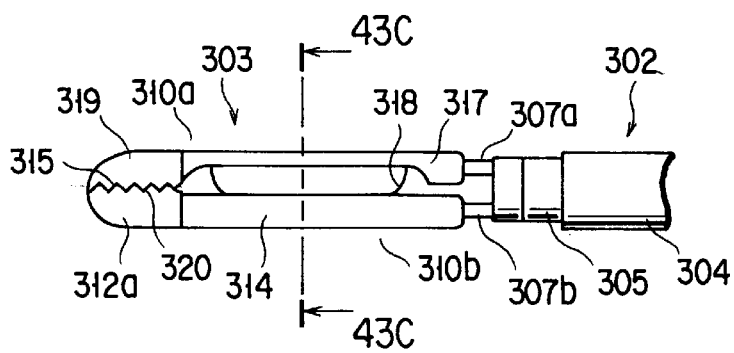
FIG. 43B is a side view of the treatment portion shown in FIG. 43A.
Figure 43C:
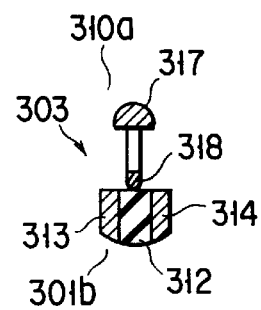
FIG. 43C is a sectional view taken along a line 43C—43C in FIG. 43B.

FIGS. 43A to 43C show the 17th embodiment of the present invention. As shown in FIGS. 43A to 43C, a bipolar forceps 300 as a high-frequency treatment tool of this embodiment comprises a long insertion portion 302 to be inserted into the body cavity of a patient, a treatment portion 303 attached to the distal end portion of the insertion portion 302 to grip vital tissue and coagulate or incise it, and an operation portion (not shown) coupled to the proximal end portion of the insertion portion 302.

The insertion portion 302 is comprised of a rotatable outer sheath 304 and an inner sheath 305 inserted in the outer sheath 304 to move back and forth. The inner sheath 305 is moved back and forth by operating the operation portion. A holding member having electrical insulating properties is fitted in the inner sheath 305. A pair of elastic members 307*a* and 307*b* are stationarily held by the holding member. The elastic members 307*a* and 307*b* are comprised of conductive rods formed from spring steel or the like. Each conductive rod is covered with an insulating tube. The proximal end portions of the conductive rods of the elastic members 307*a* and 307*b* are connected to a connector receptacle (not shown) of the operation portion, and the distal end portions are projected from the distal end of the inner sheath 305. The elastic members 307*a* and 307*b* have first and second jaws 310*a* and 310*b* at their distal ends, respectively, and always bias the jaws 310*a* and 310*b* in the opening direction.

In this arrangement, when the operation portion is operated in a predetermined direction, the inner sheath 305 moves forward in the axial direction, and the elastic members 307*a* and 307*b* are relatively retracted into the inner sheath 305 (FIG. 43B). At this time, the elastic members 307*a* and 307*b* are pressed inward by the inner wall of the inner sheath 305 to close the jaws 310*a* and 310*b*. When the operation portion is operated in the opposite direction, the elastic members 307*a* and 307*b* relatively project from the inner sheath 305, and the jaws 310*a* and 310*b* are opened by the restoring force of the elastic members 307*a* and 307*b* (FIG. 43A).

The second jaw 310*b* has two coagulation electrode portions 313 and 314 electrically insulated from each other by an insulating member 312. The first and second coagulation electrode portions 313 and 314 are positioned on both sides of the insulating member 312 to sandwich the insulating member 312 therebetween. A distal end portion 312*a* of the insulating member 312 extends from the distal end sides of the two electrode portions 313 and 314. A serrate uneven portion 315 is formed on the surface (surface opposing the first jaw 310*a*) of the distal end portion 312*a*.

The first jaw 310*a* comprises a main body portion 317 extending opposite to the second jaw 310*b*, a wire-shaped incision electrode portion 318 extending in the longitudinal direction of the main body portion 317 almost at the central portion of the main body portion 317 and projecting in a U shape from the main body portion 317 to the second jaw 310*b* side, and a gripping element 319 provided at the distal end portion of the main body portion 317 and opposing the distal end portion 312*a* of the insulating member 312 of the second jaw 310*b*. In this case, the incision electrode portion 318 comes into contact with only the insulating member 312 when the jaws 310*a* and 310*b* (treatment portion 303) are closed. The gripping element 319 is made of a material having electrical insulating properties and has, on its surface (surface opposing the second jaw 310*b*), a serrate uneven portion 320 meshing with the uneven portion 315 of the distal end portion 312*a* of the insulating member 312.

As described above, in the bipolar forceps 300 of this embodiment, when the treatment portion 303 is completely closed, the incision electrode portion 318 of the first jaw 310*a* comes into contact with only the insulating member 312 of the second jaw 310*b*. That is, when tissue is gripped, the conductive portions of the jaws 310*a* and 310*b* to which a high-frequency current is supplied do not come into contact with each other. Since no electrical short circuit occurs between the jaws 310*a* and 310*b*, even thin membranous tissue can be reliably coagulated or incised.

In the bipolar forceps 300 of this embodiment, the insulating member 312 is inserted between the two electrode portions 313 and 314 of the second jaw 310*b*, and the tissue can also be gripped by the insulating member 312. Hence, the operator can reliably grip the tissue without missing it and coagulate/incise it. Especially, in this embodiment, since the distal end portion 312*a* of the insulating member 312 and the gripping element 319 extend to project forward from the electrode portions 313, 314, and 318, and the uneven portions 315 and 320 are formed on the surfaces (part of the gripping surfaces for gripping tissue) of the distal end portion 312*a* and gripping element 319, the gripping area increases, and the tissue can be reliably gripped without any slip.

In this embodiment, only one of the gripping element 319 and the distal end portion 312*a* need be made of an insulating material. The gripping element 319 and distal end portion 312*a* need not be wholly formed from the insulating material. For example, the surfaces of the gripping element 319 and distal end portion 312*a* may be coated with Teflon or a ceramic.

Figure 44:
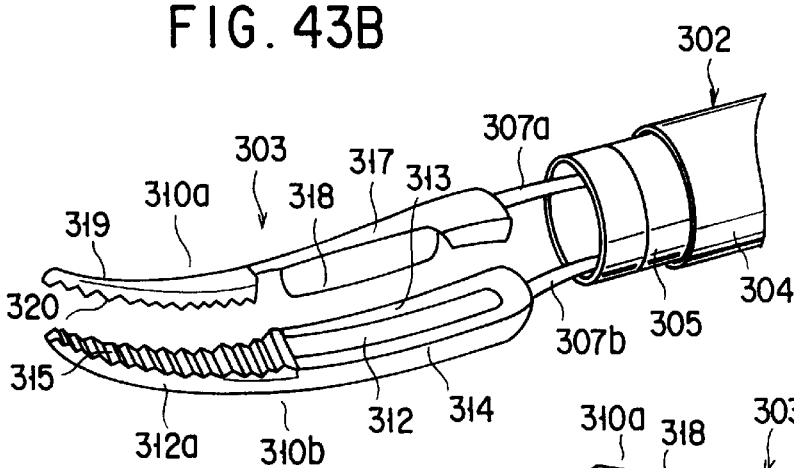
FIG. 44 is a perspective view of the treatment portion of a high-frequency treatment tool according to the first modification of the 17th embodiment.

FIG. 44 shows a modification of the 17th embodiment. The first and second jaws 310*a* and 310*b* are formed as a Kelly clamp portion curved to one side. The arrangement of the remaining portions is the same as in the 17th embodiment.

Figure 45:
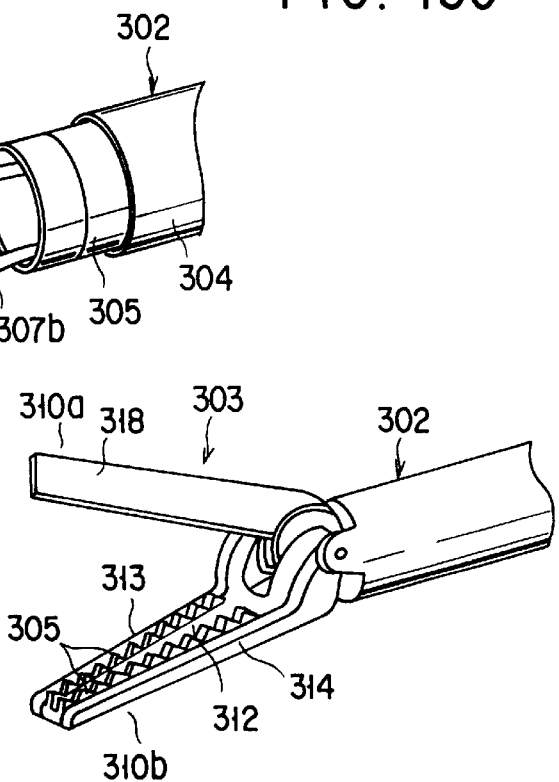
FIG. 45 is a perspective view of a treatment portion of a high-frequency treatment tool according to the second modification of the 17th embodiment.

In the 17th embodiment, the uneven portions 315 and 320 are formed partially on the gripping surfaces of the jaws 310*a* and 310*b*. In FIG. 45, the uneven portion 315 is formed throughout the total length of the insulating member 312 of the second jaw 310b. More specifically, the serrate uneven portion 315 is formed on both sides of the gripping surface of the second jaw 310b throughout the total length. In FIG. 45, although the treatment portion 303 is slightly different from the treatment portion (jaws 310a and 310b) of the 17th embodiment, the same reference numerals as in the 17th embodiment denote the same parts.

FIGS. 46A to 48B show the 18th embodiment of the present invention. As shown in FIGS. 46A and 46B, a bipolar forceps 401 as a high-frequency treatment tool comprises a long insertion portion 402 to be inserted into the body cavity of a patient, a treatment portion 403 attached to the distal end portion of the insertion portion 402 to grip vital tissue and coagulate or incise it in the body cavity, to which power can be supplied, and an operation portion 404 coupled to the proximal end portion of the insertion portion 402.

The insertion portion 402 has a sheath 406 rotatably supported by a rotary operation portion 405 of the operation portion 404. A driving shaft 407 extending into the operation portion 404 is inserted in the sheath 406 to move back and forth. First and second jaws 408a and 408b forming electrodes of the treatment portion 403 are provided at the distal end portion of the driving shaft 407 so as to be opened/closed.

The operation portion 404 has a fixed handle 411 integrated with an operation portion main body 409 and a movable handle 413 attached to the operation portion main body 409 through a pivot pin 412 as a fulcrum to freely pivot. By pivoting the movable handle 413, the driving shaft 407 can be moved back and forth to open/close the first and second jaws 408a and 408b.

As shown in FIGS. 47A to 47C, the first jaw 408a has an incision electrode 414 as a first electrode. The second jaw 408b has first and second coagulation electrodes 415a and 415b as second electrodes. For the incision electrode 414, a conductive wire such as a metal wire is bent in an almost U shape, and the two end portions are fixed to the front and rear ends of the first jaw 408a, thereby forming an incision portion 414a almost parallel to the first jaw 408a.

A flat insulating member 416 consisting of a ceramic or synthetic resin material is fixed to the second jaw 408b. Notched step portions 416a and 416b are formed at the edge portions on both sides of the upper surface of the insulating member 416. The first coagulation electrode 415a is fixed on one notched step portion 416a, and the second coagulation electrode 415b is fixed on the other notched step portion 416b. Hence, the first and second coagulation electrodes 415a and 415b are electrically insulated by the insulating member 416. The step difference of the notched step portions 416a and 416b substantially equals the height of the first and second coagulation electrodes 415a and 415b. The coagulation surfaces as the upper surfaces of the first and second coagulation electrodes 415a and 415b are flush with an upper surface 416c of the insulating member 416. The incision portion 414a of the incision electrode 414 opposes the upper surface 416c.

As for the length of the incision electrode 414 in the longitudinal direction, the far end of the incision electrode 414 is closer to the near-end side than that of the first and second coagulation electrodes 415a and 415b, so a shift amount L (L≧0) is present. This shift amount L is, e.g., 0.5 to 2.0 mm. The near end of the incision electrode 414 is closer to the far-end side than that of the first and second coagulation electrodes 415a and 415b, so the incision range is narrower than the coagulation range.

The function of the 18th embodiment will be described next with reference to FIGS. 48A and 48B.

The bipolar forceps 401 is electrically connected to a high-frequency cautery power supply unit (not shown), the insertion portion 402 of the bipolar forceps 401 is inserted into the body of a patient, and the treatment portion 403 at the distal end of the insertion portion 402 is placed near vital tissue A to be treated in the body. As shown in FIG. 48A, the vital tissue A to be treated is inserted between the opened first and second jaws 408a and 408b. When the movable handle 413 is pivoted to the fixed handle 411 side, the driving shaft 407 moves backward. Upon the backward movement of the driving shaft 407, the first and second jaws 408a and 408b are closed, so the vital tissue A is gripped between the incision electrode 414 and the first and second coagulation electrodes 415a and 415b.

In this state, a high-frequency current is flowed from the high-frequency cautery power supply unit. A coagulation current is flowed across the first coagulation electrode 415a and the second coagulation electrode 415b to coagulate the vital tissue A. A hatched portion corresponds to the coagulated portion. The coagulation range is represented by L1.

Subsequently, when an incision current is flowed to the incision electrode 414 and first and second coagulation electrodes 415a and 415b, and simultaneously, the movable handle 413 is further pivoted to the fixed handle 411 side, the incision electrode 414 and the first and second coagulation electrodes 415a and 415b are further closed, as shown in FIG. 48B. The coagulated vital tissue A is incised by the incision portion 414a of the incision electrode 414. At this time, since the far end of the incision electrode 414 is closer to the near-end side than that of the first and second coagulation electrodes 415a and 415b, and the shift amount L is present, an incision range L2 is narrower than the coagulation range L1. Bleeding can be prevented because incision is performed within the range of coagulated portion.

In this embodiment, when the treatment portion 403 is completely closed, the incision electrode 414 of the first jaw 408a comes into contact with only the insulating member 416 of the second jaw 408b. That is, when tissue is gripped by the jaws 408a and 408b, the conductive portions to which a high-frequency current is supplied do not come into contact with each other. Hence, no electrical short circuit occurs between the jaws 408a and 408b, and even thin film-shaped tissue can be reliably coagulated or incised.

Figure 78A:
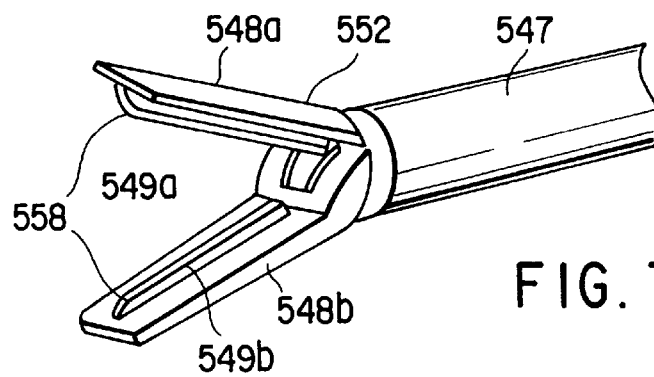
Figure 78B:
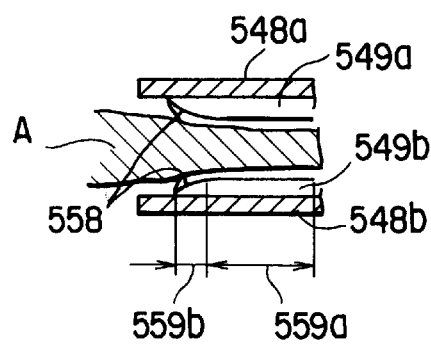
Figure 78C:
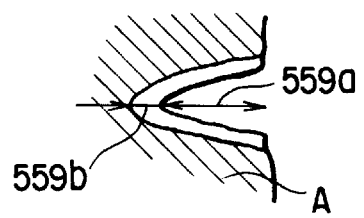

Generally, vital tissue is coagulated over a larger area than the area of the vital tissue in contact with the coagulation electrodes 415a and 415b (FIGS. 78B and 78C). Hence, in this embodiment, the shift amount L between the incision electrode 414 and the coagulation electrodes 415a and 415b may be 0.

FIGS. 49A and 49B show the 19th embodiment of the present invention. The same reference numerals as in the 18th embodiment denote the same parts in the 19th embodiment, and a detailed description thereof will be omitted.

A bipolar forceps of this embodiment has an incision electrode 417 having a thin flat knife-edged incision portion 417a. The far end of the incision electrode 417 is closer to the near-end side than that of first and second coagulation electrodes 415a and 415b, and a shift amount L is present. For this reason, the same function and effect as in the 18th embodiment can be obtained.

FIGS. 50A and 50B show the 20th embodiment of the present invention. The same reference numerals as in the 18th embodiment denote the same parts in the 20th embodiment, and a detailed description thereof will be omitted.

A bipolar forceps of this embodiment has an incision electrode 418 having a rod-like incision portion 418a formed by bending the distal end portion. The far end of the incision electrode 418 is closer to the near-end side than that of first and second coagulation electrodes 415a and 415b, and a shift amount L is present. For this reason, the same function and effect as in the 18th embodiment can be obtained.

Figure 53:
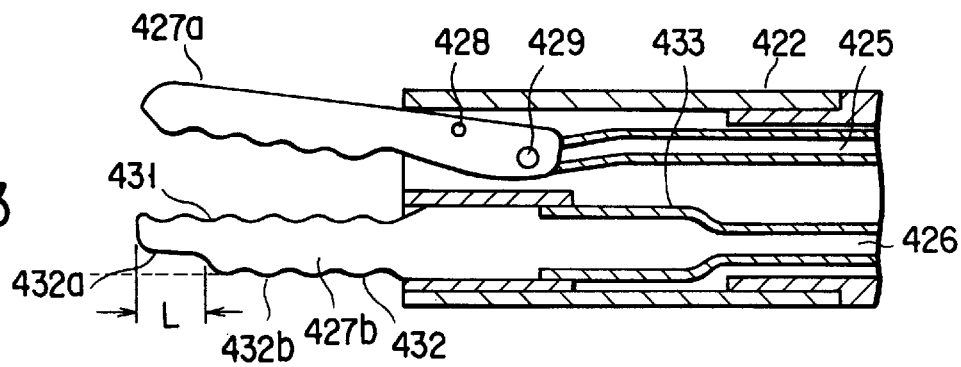
FIG. 53 is a partially longitudinally cutaway side view of the treatment portion of the high-frequency treatment tool shown in FIG. 51.

FIGS. 51 to 53 show the 21st embodiment of the present invention. A high-frequency treatment tool 421 of this embodiment has a tubular insertion portion 422, and an operation portion 423 provided on the hand side of the insertion portion 422. The operation portion 423 has an insertion portion rotation knob 424 for rotating the insertion portion 422 about its axial center.

An operation shaft 425 and a rotary shaft 426 are inserted into the insertion portion 422 to move back and forth in the axial direction. A first jaw 427a forming a gripping portion is attached to the distal end portion of the insertion portion 422 to freely pivot about a pivot pin 428 as a fulcrum. The proximal end portion of the first jaw 427a is coupled to the operation shaft 425 through a coupling pin 429, and the distal end portion projects from the front end of the insertion portion 422. The proximal end portion of the operation shaft 425 is coupled to a movable handle 430 of the operation portion 423.

The distal end portion of the rotary shaft 426 projects from the front end of the insertion portion 422. A second jaw 427b forming a gripping portion is integrated with the projecting portion. The first and second jaws 427a and 427b constitute a treatment portion for gripping and treating vital tissue A.

As shown in FIGS. 52A and 52B, the second jaw 427b has a trapezoidal or almost triangular cross section. A coagulation electrode 431 is formed at the base portion, and an incision electrode 432 is formed at the vertex portion. More specifically, when the rotary shaft 426 is rotated about its axial center to grip the vital tissue A by the second jaw 427b with the coagulation electrode 431 facing up to oppose the first jaw 427a, as shown in FIG. 52A, the vital tissue A can be coagulated. When the rotary shaft 426 is rotated about its axial center to grip the vital tissue A by the second jaw 427b with the incision electrode 432 facing up to oppose the first jaw 427a, as shown in FIG. 52B, the vital tissue A can be incised.

As shown in FIG. 53, a notched portion 432a is formed at the distal end portion of the incision electrode 432 of the second jaw 427b. An incision portion 432b is made shorter in the longitudinal direction by the notched portion 432a. More specifically, the far end of the incision portion 432b of the incision electrode 432 is closer to the near-end side than that of the coagulation electrode 431, and a shift amount L is present.

The rotary shaft 426 integrated with the second jaw 427b is rotatably supported by a support pipe 433 in the insertion portion 422. The proximal end portion of the rotary shaft 426 is coupled to a jaw rotation knob 434 of the operation portion 423. When the jaw rotation knob 434 is operated, the direction of the second jaw 427b can be arbitrarily changed.

The function of the 21st embodiment will be described next.

First, the jaw rotation knob 434 is rotated to rotate the rotary shaft 426 and set the coagulation electrode 431 of the second jaw 427b upward and oppose the first jaw 427a. In this state, when the movable handle 430 is operated to move the operation shaft 425 backward, the first jaw 427a pivots about the pivot pin 428 as a fulcrum to grip the vital tissue A together with the coagulation electrode 431 of the second jaw 427b, as shown in FIG. 52A. When a coagulation current is flowed across the first and second jaws 427a and 427b, the vital tissue A is coagulated.

Subsequently, the first and second jaws 427a and 427b are temporarily opened. The jaw rotation knob 434 is operated to rotate the rotary shaft 426 through 180° to set the incision electrode 432 of the second jaw 427b upward and opposite to the first jaw 427a and grip the vital tissue A. The vital tissue A is gripped between the first jaw 427a and the incision electrode 432 of the second jaw 427b. When an incision current is flowed across the first and second jaws 427a and 427b, the vital tissue A is incised.

At this time, the far end of the incision portion 432b of the incision electrode 432 is closer to the near-end side than that of the coagulation electrode 431, and the shift amount L is present. For this reason, the same function and effect as in the 18th embodiment can be obtained.

In this embodiment as well, an electrical insulating portion may be formed on the gripping surface of at least one gripping portion (jaw 427a or 427b), as in the first to fifth embodiments. In this case, a predetermined gap is formed between the gripping surfaces of the gripping portions when the gripping portions are completely closed to make the electrical insulating portion abut against the gripping surface of the other gripping portion, thereby preventing a short circuit between the electrode portions of the gripping portions. In addition, as in the 11th embodiment, an abutment portion 121 may be formed on the movable handle 430, and a projecting portion 120 may be formed on the grip. When the projecting portion 120 abuts against the abutment portion 121, the treatment portion is not closed anymore, and a predetermined gap C is formed between the first and second jaws 427a and 427b.

Figure 54A:
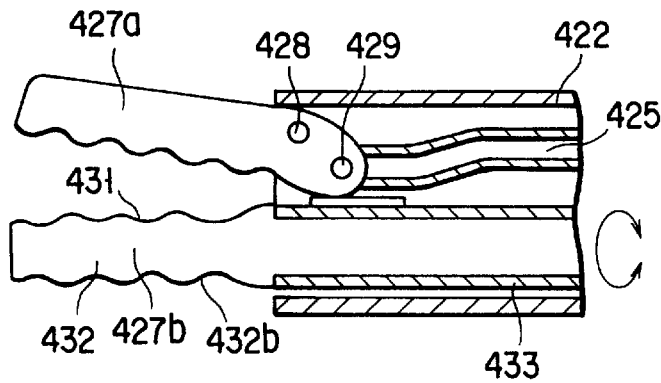
FIG. 54A is a partially longitudinally cutaway side view of a treatment portion of a high-frequency treatment tool according to the 22nd embodiment of the present invention upon coagulating tissue.
Figure 54B:
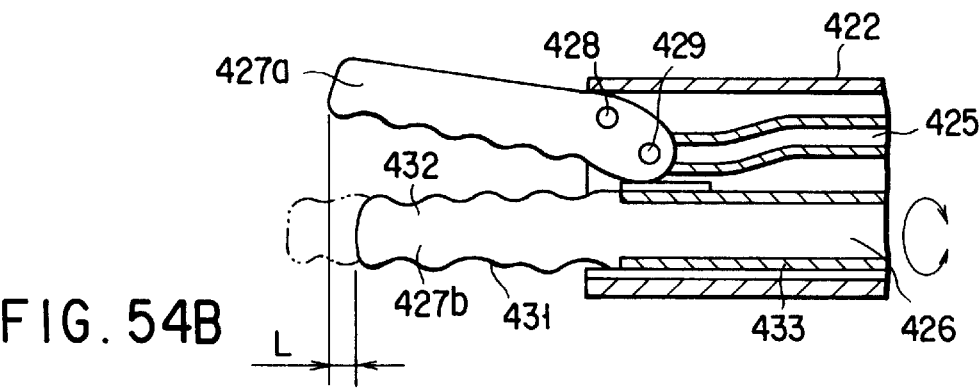
FIG. 54B is a partially longitudinally cutaway side view of the treatment portion shown in FIG. 54A upon incising tissue.
Figure 55:
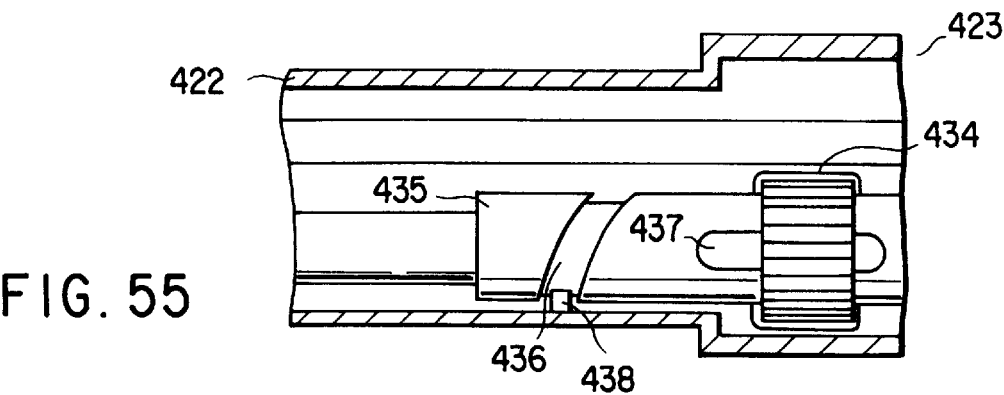
FIG. 55 is a longitudinal sectional view of an operation portion of the high-frequency treatment tool shown in FIG. 54A.

FIGS. 54A to 55 show the 22nd embodiment of the present invention. The same reference numerals as in the 21st embodiment denote the same parts in the 22nd embodiment, and a detailed description thereof will be omitted.

In this embodiment, an incision electrode 432 has no notched portion 432a, and an incision portion 432b is formed throughout the total length of the incision electrode 432. In addition, a large-diameter portion 435 is integrated with the proximal end portion of a rotary shaft 426 coupled to a second jaw 427b and rotatably supported by a support pipe 433. The large-diameter portion 435 has a cam groove 436 in the outer surfaces and a key groove 437 in the axial direction. A cam pin 438 projecting from the inner wall of the support pipe 433 engages with the cam groove 436, and the jaw rotation knob 434 engages with the key groove 437.

When the jaw rotation knob 434 is operated, the direction of the second jaw 427b can be changed through the rotary shaft 426. Upon rotating the rotary shaft 426, the rotary shaft 426 moves backward in the axial direction due to the cam groove 436 engaging with the cam pin 438, so the second jaw 427b is retracted to the hand side.

During coagulation, the second jaw 427b projects, and a wide range is coagulated by a coagulation electrode 431. When the jaw rotation knob 434 is operated during incision, the rotary shaft 426 moves backward in the axial direction along the cam groove 436 engaging with the cam pin 438, and the second jaw 427b is retracted to the hand side. Hence, the incision range by the incision electrode 432 of the second jaw 427b is narrower than the coagulation range by the retraction amount of the second jaw 427b. Since incision is always performed within the coagulated range, bleeding can be prevented. More specifically, since the far end of the incision electrode 432 is closer to the near-end side than that of the coagulation electrode 431 during incision, and a shift amount L is present, the same function and effect as in the 18th embodiment can be obtained.

FIGS. 56A to 57D show the 23rd embodiment of the present invention. The same reference numerals as in the 18th embodiment denote the same parts in the 23rd embodiment, and a detailed description thereof will be omitted.

In this embodiment, a second jaw 408b has first and second coagulation electrodes 440a and 440b as second electrodes. The height of the first and second coagulation electrodes 440a and 440b is larger than the step difference of notched step portions 416a and 416b. The upper surfaces of the first and second coagulation electrodes 440a and 440b project from an upper surface 416c of an insulating member 416. An incision portion 414a of an incision electrode 414 opposes the lower upper surface 416c.

The coagulation surfaces of the first and second coagulation electrodes 440a and 440b are notched into an arcuated shape at the far end to form chamfered portions 441. The two corner portions of the coagulation surfaces are notched into an arcuated shape at the far end to form chamfered portions 442. The outer ridge portion of each of the first and second coagulation electrodes 440a and 440b and the ridge portion opposing the upper surface 416c of the insulating member 416 are notched into an arcuated shape to form chamfered portions 443 and 444, respectively.

The function of the 23rd embodiment will be described below with reference to FIGS. 57A to 57D.

As in the 18th embodiment, a coagulation current is flowed across the first coagulation electrode 440a and the second coagulation electrode 440b to coagulate vital tissue A. After this, as shown in FIG. 57A, incision is started by flowing an incision current across the incision electrode 414 and the first and second coagulation electrodes 440a and 440b. The movable handle 413 is pivoted to the fixed handle 411 side, the incision electrode 414 and first and second coagulation electrodes 440a and 440b are further closed, as shown in FIGS. 57B and 57D. Hence, the coagulated vital tissue A is incised by the incision portion 414a of the incision electrode 414.

At this time, a tensile force for stretching the vital tissue A to both sides of the incision electrode 414 is applied by the chamfered portions 443 and 444 formed at the ridge portions of the first and second coagulation electrodes 440a and 440b. The tensile force acting on the far-end side is efficiently transmitted to the near-end side by the chamfered portions 441 and 442 of the first and second coagulation electrodes 440a and 440b. Hence, an incisional wound a of the vital tissue A is separated from the incision electrode 414 while gradually stretching as incision progresses. As shown in FIG. 57C, a terminal b of the incisional wound a of the vital tissue A slips on the chamfered portions 441 and 442 at the far end of the first and second coagulation electrodes 440a and 440b and is separated from the incision electrode 414, as indicated by an arrow. For this reason, the end of incision is easy to determine, and the treatment portion 403 can be easily separated from the vital tissue A.

In this embodiment, the chamfered portions 441 to 444 of the first and second coagulation electrodes 440a and 440b have arcuated shapes. However, they may have substantially triangular shapes. The chamfered portions 443 and 444 are formed at the outer and inner ridge portions of each of the first and second coagulation electrodes 440a and 440b. However, the chamfered portion need only be formed on at least one of the ridge portions. A tripolar high-frequency treatment tool has been described above. However, this embodiment can also be applied to a bipolar high-frequency treatment tool.

FIGS. 58A and 58B show the 24th embodiment of the present invention. The same reference numerals as in the 23rd embodiment denote the same parts in the 24th embodiment, and a detailed description thereof will be omitted.

In this embodiment, serrate uneven portions 445 are formed on the coagulation surfaces of first and second coagulation electrodes 440a and 440b. When the uneven portions 445 are formed on the coagulation surfaces, vital tissue A can be prevented from escaping to the far-end side of a treatment portion 403 during coagulation or incision. Hence, in addition to the effect of the 23rd embodiment, the target portion of the vital tissue A can be reliably gripped.

In DE 4032471 C2 described above as a prior art, the incision electrode and the pair of coagulation electrodes of the gripping portion of the high-frequency treatment tool are formed by bending a wire. Hence, the incision electrode and coagulation electrodes may short-circuit due to twist or deformation of the distal end portion of the high-frequency treatment tool, or the target portion at the center of the coagulation range cannot be incised when the incision electrode is closed, and bleeding may occur. FIG. 10 of Jpn. Pat. Appln. KOKAI Publication No. 10-000199 shows a structure in which an insulating member is inserted between the electrodes. However, the same problem as described above is posed because the incision electrode does not align to the center of the insulating member during incision.

FIGS. 59, 60A, and 60B show the 25th embodiment capable of solving this problem. A high-frequency treatment tool of the 25th embodiment has the same basic arrangement as that of the 18th embodiment, and a detailed description thereof will be omitted.

A first jaw 451a constituting a gripping portion 450 for gripping vital tissue A has an incision electrode 452 as the first electrode. A second jaw 451b has first and second coagulation electrodes 453a and 453b as the second electrodes. The incision electrode 452 is constituted by a plate element 454 with its surface coated with an insulating material, and a conductive wire 455 formed by bending a metal wire or the like into a substantially U shape and fixing the two end portions to the front and rear ends of the plate element 454.

The second jaw 451b is constituted by a plate element 456 with its surface being coated with an insulating material, and an insulating member 457 consisting of a ceramic or a synthetic resin material and fixed at the central portion of the plate element 456. The first and second coagulation electrodes 453a and 453b are fixed on both sides of the insulating member 457. That is, the first and second coagulation electrodes 453a and 453b are electrically insulated from each other by the insulating member 457.

The upper surface of the insulating member 457 is substantially flush with the coagulation surfaces of the first and second coagulation electrodes 453a and 453b. A wide-angled V-shaped guide portion 458 for guiding the incision electrode 452 is formed on the upper surface of the insulating member 457. When the first and second jaws 451a and 451b are closed, the incision electrode 452 is aligned to the axial center between the first and second coagulation electrodes 453a and 453b.

The function of the 25th embodiment will be described next with reference to FIGS. 60A and 60B.

As shown in FIG. 60A, when vital tissue A to be treated is sandwiched and gripped by the first and second jaws 451a and 451b, the vital tissue A is gripped between the incision electrode 452 and the first and second coagulation electrodes 453a and 453b including the insulating member 457. Since the wide-angled V-shaped guide portion 458 is formed on the upper surface of the insulating member 457, the vital tissue A has also a wide-angled V shape along the guide portion 458.

In this state, when a high-frequency current is flowed from a high-frequency cautery power supply unit, a coagulation current flows across the first coagulation electrode 453a and the second coagulation electrode 453b to coagulate the vital tissue A. Subsequently, when an incision current is flowed across the incision electrode 452 and the first and second coagulation electrodes 453a and 453b, and the incision electrode 452 and first and second coagulation electrodes 453a and 453b are further closed, the coagulated vital tissue A is incised by the incision electrode 452.

At this time, the incision electrode 452 is aligned to the center between the first and second coagulation electrodes 453a and 453b by the guide portion 458 formed on the upper surface of the insulating member 457. That is, even when the incision electrode 452 slightly deforms to the left or right, the position of the conductive wire 455 is corrected by the guide portion 458 to the center between the first and second coagulation electrodes 453a and 453b. Hence, the short circuit between the incision electrode 452 and the first and second coagulation electrodes 453a and 453b can be prevented, and the target portion of the vital tissue A can be reliably incised.

In this embodiment, the wide-angled V-shaped guide portion 458 is formed on the upper surface of the insulating member 457. However, a recessed arcuated guide portion 459 may be formed, as shown in FIG. 61A. Alternatively, an inverted trapezoidal guide portion 460 may be formed, as shown in FIG. 61B. In FIG. 61C, the coagulation surfaces of the first and second coagulation electrodes 453a and 453b are set at slightly higher level than the upper surface of the insulating member 457 to form a step difference H. With this arrangement, a tensile force is applied to the vital tissue A, so the vital tissue A can be easily incised, and the incisional wound can be easily separated from the incision electrode 452.

FIG. 62 shows a disclosure example of a treatment portion comprising an incision jaw 461 and a coagulation jaw 462. Electrode support portions 463a and 463b project at the far end and near end of the incision jaw 461. A conductive wire 464 as an incision electrode is kept taut between the electrode support portions 463a and 463b. Clearance grooves 465a and 465b opposing the distal end portions of the electrode support portions 463a and 463b and fitted on the electrode support portions 463a and 463b are formed at the far end and near end of the coagulation jaw 462. According to this disclosure example, the rigidity of the incision electrode increases, so deformation during incision can be prevented.

FIGS. 63A to 64B show the 26th embodiment of the present invention. As shown in FIGS. 63A to 63C, a bipolar forceps 501 as a high-frequency treatment tool comprises a long insertion portion 502 to be inserted into the body cavity of a patient, a treatment portion 503 attached to the distal end portion of the insertion portion 502 to grip vital tissue and coagulate or incise it in the body cavity, to which power can be supplied, and an operation portion 504 coupled to the proximal end portion of the insertion portion 402.

The insertion portion 502 has a rotatable outer sheath 505. An inner sheath 507 of the outer sheath 505 is inserted in a grip 506 constituting the operation portion 504. The treatment portion 503 has a long rod (not shown) inserted in the outer sheath 505. At the distal end portion of the rod, a pair of jaws 508a and 508b as electrodes constituting the treatment portion 503 are fixed to elastic members 509a and 509b for biasing the jaws 508a and 508b in the opening direction. The elastic members 509a and 509b are formed from spring steel or the like and covered with insulating members.

Figure 64A:
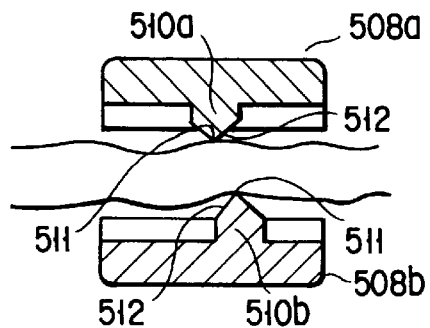
FIG. 64A is a sectional view showing a state wherein tissue is gripped by the treatment portion of the high-frequency treatment tool shown in FIG. 63A.
Figure 64B:
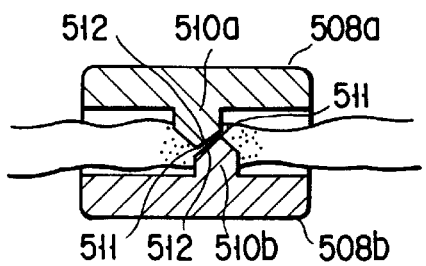
FIG. 64B is a sectional view showing a state wherein tissue is coagulated/incised by the high-frequency treatment tool shown in FIG. 63A.

As shown in FIGS. 64A and 64B, the jaws 508a and 508b have serrate portions which mesh with each other when the jaws 508a and 508b are closed, so vital tissue A can be reliably gripped. Incision projections 510a and 510b as projecting portions are integrated with the jaws 508a and 508b along the longitudinal direction at substantially middle portions in the direction of width of the mesh portions of the jaws 508a and 508b.

Each of the incision projections 510a and 510b has a substantially V-shaped section and an acute-angled portion 511 at the distal end portion and oblique surfaces 512 on both sides of the distal end portion. The incision projection 510a on the jaw 508a side is formed at the middle portion in the direction of width of the jaw 508a. The incision projection 510b on the jaw 508b side is shifted to one side in the direction of width of the jaw 508b. When the jaws 508a and 508b are closed, the acute-angled portions 511 do not abut against each other. Instead, the incision projections 510a and 510b lap to joint the right and left oblique surfaces 512 with each other.

As shown in FIGS. 63A to 63C, a conductive member (not shown) connected to the jaws 508a and 508b of the treatment portion 503 is connected to a connector receptacle 513 of the operation portion 504 through the outer sheath 505 of the insertion portion 502. The connector receptacle 513 is connected to a high-frequency cautery power supply unit 515 through a cable 514. The high-frequency cautery power supply unit 515 has a foot switch 516.

The grip 506 has a trigger 517 as a forceps operation means. The trigger 517 is coupled to the upper end portion of the grip 506 to freely pivot about a pivot pin 518. The upper end portion of the pivot fulcrum of the trigger 517 is coupled to the proximal end portion of the inner sheath 507.

The grip 506 has a finger hook portion 506a on which the operator places the thumb. The trigger 517 has finger hook portions 517a and 517b on which the operator places the index and middle fingers, respectively. When the trigger 517 is opened in a direction indicated by an arrow a, the inner sheath 507 moves backward to open the jaws 508a and 508b. When the trigger 517 is closed in a direction indicated by an arrow b, the inner sheath 507 moves forward to close the jaws 508a and 508b.

The function of the 26th embodiment will be described next.

The cable 514 is connected to the connector receptacle 513 of the bipolar forceps 501 to electrically connect the bipolar forceps 501 to the high-frequency cautery power supply unit 515. In the initial state, the trigger 517 of the operation portion 504 is pivoted to the direction indicated by the arrow a. In this state, the pair of elastic members 509a and 509b of the treatment portion 503 project from the inner sheath 507 to open the jaws 508a and 508b, as shown in FIG. 63B.

When the finger hook portions 517a and 517b of the trigger 517 are pulled to the grip 506 side against the spring force of the biasing members in the grip 506, the inner sheath 507 moves forward in the axial direction. As the inner sheath 507 moves forward, the elastic members 509a and 509b are relatively retracted into the inner sheath 507 to close the jaws 508a and 508b, as shown in FIG. 63A.

In this state, the insertion portion 502 of the bipolar forceps 501 is inserted into the body of a patient, and the treatment portion 503 at the distal end of the insertion portion 502 is placed near the vital tissue A to be treated in the body. When the trigger 517 is released, the trigger 517 returns to the home position by the spring force of the biasing member in the grip 506. The elastic members 509a and 509b relatively project from the inner sheath 507, and the jaws 508a and 508b are opened by the elastic restoring force of the elastic members 509a and 509b.

After the vital tissue A is inserted between the opened jaws 508a and 508b, the finger hook portions 517a and 517b of the trigger 517 are pulled to the grip 506 side to move the inner sheath 507 forward in the axial direction. As the inner sheath 507 moves forward, the elastic members 509a and 509b are relatively retracted into the inner sheath 507 to close the jaws 508a and 508b. The vital tissue A is gripped between the pair of jaws 508a and 508b, as shown in FIG. 64A.

Since the jaws 508a and 508b have serrate portions which mesh with each other when the jaws 508a and 508b are closed, the vital tissue A is reliably gripped. In this state, a high-frequency current flows from the high-frequency cautery power supply unit 515 to the connector receptacle 513 through the cable 514. A coagulation current flows across the jaws 508a and 508b to coagulate the vital tissue A.

Subsequently, when the finger hook portions 517a and 517b of the trigger 517 are further pulled to the grip 506 side, the jaws 508a and 508b are further closed, and an incision current flows across the jaws 508a and 508b. The incision projections 510a and 510b move close to each other. Since the incision projections 510a and 510b lap to joint the oblique surfaces 512 with each other without making the acute-angled portions 511 abut against each other, the vital tissue A is incised by the pair of jaws 508a and 508b, as shown in FIG. 64B.

The coagulation current generally has load characteristics representing that when the impedance of the vital tissue A increases upon coagulation, the output decreases, as indicated by a broken line in FIG. 63C. In this embodiment, however, power control is performed in a constant power output mode in which even when the impedance increases, the output does not decrease, as indicated by a solid line in FIG. 63C. Hence, power can be concentrated in a short time to incise the vital tissue A. That is, incision can be performed simultaneously with coagulation without switching between the coagulation current and the incision current.

When coagulation and incision are complete, the trigger 517 is pivoted in the direction indicated by the arrow a. The inner sheath 507 moves backward, and the elastic members 509a and 509b are opened by the elastic restoring force. The jaws 508a and 508b are released from the vital tissue A.

To peel the vital tissue A, while the jaws 508a and 508b are closed using the trigger 517, and the distal end portions of the jaws 508a and 508b are pressed against the portion of the vital tissue A to be peeled, the trigger 517 is pivoted in the direction indicated by the arrow a. The inner sheath 507 moves backward, and the jaws 508a and 508b are opened by the elastic restoring force of the elastic members 509a and 509b. By repeatedly opening/closing the jaws 508a and 508b, the vital tissue A can be peeled.

According to this embodiment, gripping, coagulation, and incision of the vital tissue A can be performed by one bipolar forceps 501. Cumbersome exchange of the bipolar forceps 501 can be reduced during the operation to shorten the operation time. In addition, the tissue can be easily coagulated/incised by the series of operations of the operation portion 504 without any mechanical switching for tissue coagulation and incision.

In this embodiment as well, an electrical insulating portion may be formed on the gripping surface of at least one gripping portion (jaw 508a or 508b), as in the first to fifth embodiments. In this case, a predetermined gap is formed between the gripping surfaces of the gripping portions when the gripping portions are completely closed to make the electrical insulating portion abut against the gripping surface of the other gripping portion, thereby preventing a short circuit between the electrode portions of the gripping portions. In addition, as in the 11th embodiment, an abutment portion 121 may be formed on the trigger 517, and a projecting portion 120 may be formed on the grip 506. When the projecting portion 120 abuts against the abutment portion 121, the treatment portion 503 is not closed anymore, and a predetermined gap C is formed between the first jaw 508a and the second jaw 508b.

Figure 65:
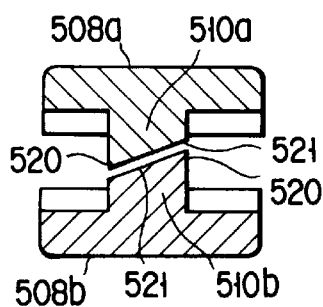
FIG. 65 is a sectional view of the treatment portion of a high-frequency treatment tool according to the 27th embodiment of the present invention.

FIG. 65 shows the 27th embodiment of the present invention. In this embodiment, the distal end portions of incision projections 510a and 510b are formed into a knife-edge shape. An acute-angled portion 520 is formed at the distal end portion, and an oblique surface 521 is formed on one side. When jaws 508a and 508b are closed, the acute-angled portions 520 do not abut against each other. Instead, the incision projections 510a and 510b lap to joint the right and left oblique surfaces 512 with each other.

Figure 66:
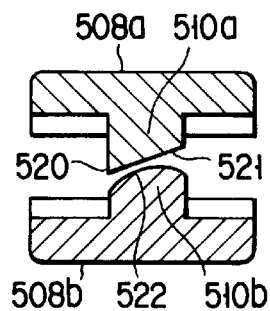
FIG. 66 is a sectional view of the treatment portion of a high-frequency treatment tool according to the 28th embodiment of the present invention.

FIG. 66 shows the 28th embodiment of the present invention. In this embodiment, the distal end portion of one incision projection 510a is formed into a knife-edge shape. An acute-angled portion 520 is formed at the distal end portion, and an oblique surface 521 is formed on one side. The distal end portion of the other incision projection 510b is formed into an arcuated portion 522. When jaws 508a and 508b are closed, the acute-angled portions 520 do not abut against the arcuated portion 522. Instead, the incision projections 510a and 510b lap to joint the oblique surface 512 with the arcuated portion 522.

Figure 67:
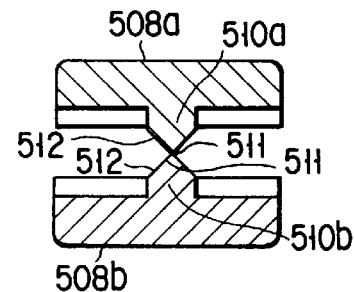
FIG. 67 is a sectional view of the treatment portion of a high-frequency treatment tool according to the 29th embodiment of the present invention.

FIG. 67 shows the 29th embodiment of the present invention. In this embodiment, each of incision projections 510a and 510b has a substantially V-shaped section and an acute-angled portion 511 at the distal end portion and oblique surfaces 512 on both sides of the acute-angled portion 511. The incision projections 510a and 510b oppose each other. When jaws 508a and 508b are closed, the acute-angled portions 511 abut against each other to incise tissue. This embodiment is effective to incise a thin film or the like because the acute-angled portions 511 abut against each other.

Figure 68:
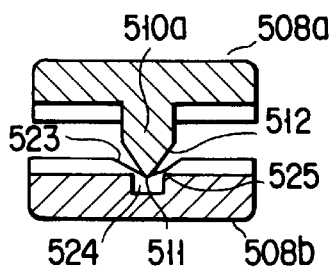
FIG. 68 is a sectional view of the treatment portion of a high-frequency treatment tool according to the 30th embodiment of the present invention.

FIG. 68 shows the 30th embodiment of the present invention. In this embodiment, one incision projection 510a has a substantially V-shaped section and an acute-angled portion 511 at the distal end portion and oblique surfaces 512 on both sides of the acute-angled portion 511. A jaw 508b has a wide-angled V-shaped groove 523 and a recessed groove 524 continuously formed at the bottom portion of the wide-angled V-shaped groove 523. Edge portions 525 are formed between the wide-angled V-shaped groove 523 and the recessed groove 524. When jaws 508a and 508b are closed, the acute-angled portion 511 of one incision projection 510a enters the recessed groove 524, and the two oblique surfaces 512 simultaneously abut against the edge portions 525 to incise tissue.

Figure 69:
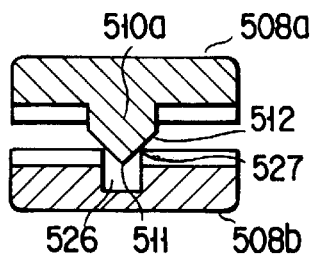
FIG. 69 is a sectional view of the treatment portion of a high-frequency treatment tool according to the 31st embodiment of the present invention.

FIG. 69 shows the 31st embodiment of the present invention. In this embodiment, one incision projection 510a has a substantially V-shaped section and an acute-angled portion 511 at the distal end portion and oblique surfaces 512 on both sides of the acute-angled portion 511. A jaw 508b has a recessed groove 526. Edge portions 527 are formed at the edges of the recessed groove 526. When jaws 508a and 508b are closed, the acute-angled portion 511 of one incision projection 510a enters the recessed groove 526, and the two oblique surfaces 512 simultaneously abut against the edge portions 527 to incise tissue.

According to the 30th and 31st embodiments, by forming the recessed grooves 524 and 526 in the jaws 508b, respectively, the tissue contact area can be decreased, and the current density can be increased.

Figure 70:
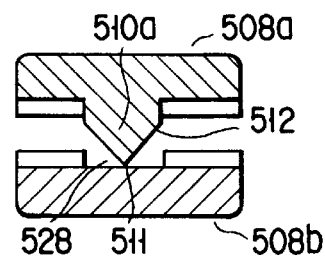
FIG. 70 is a sectional view of the treatment portion of a high-frequency treatment tool according to the 32nd embodiment of the present invention.

FIG. 70 shows the 32nd embodiment of the present invention. In this embodiment, one incision projection 510a has a substantially V-shaped section and an acute-angled portion 511 at the distal end portion and oblique surfaces 512 on both sides of the acute-angled portion 511. A jaw 508b has a flat surface 528. When jaws 508a and 508b are closed, the acute-angled portion 511 of one incision projection 510a abuts against the flat surface 528 to incise tissue. A projecting arcuated surface may be formed in place of the flat surface 528.

Figure 71A:
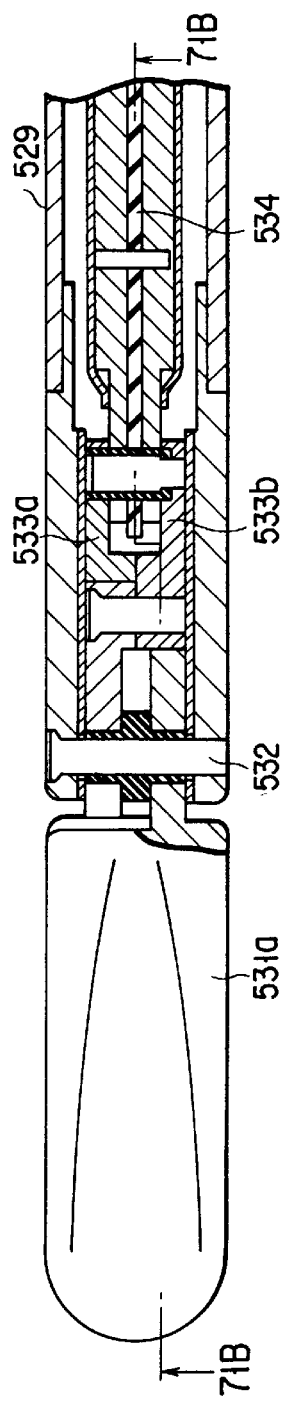
FIG. 71A is a partially longitudinally cutaway plan view of the distal end portion of a high-frequency treatment tool according to the 33rd embodiment of the present invention.
Figure 71B:
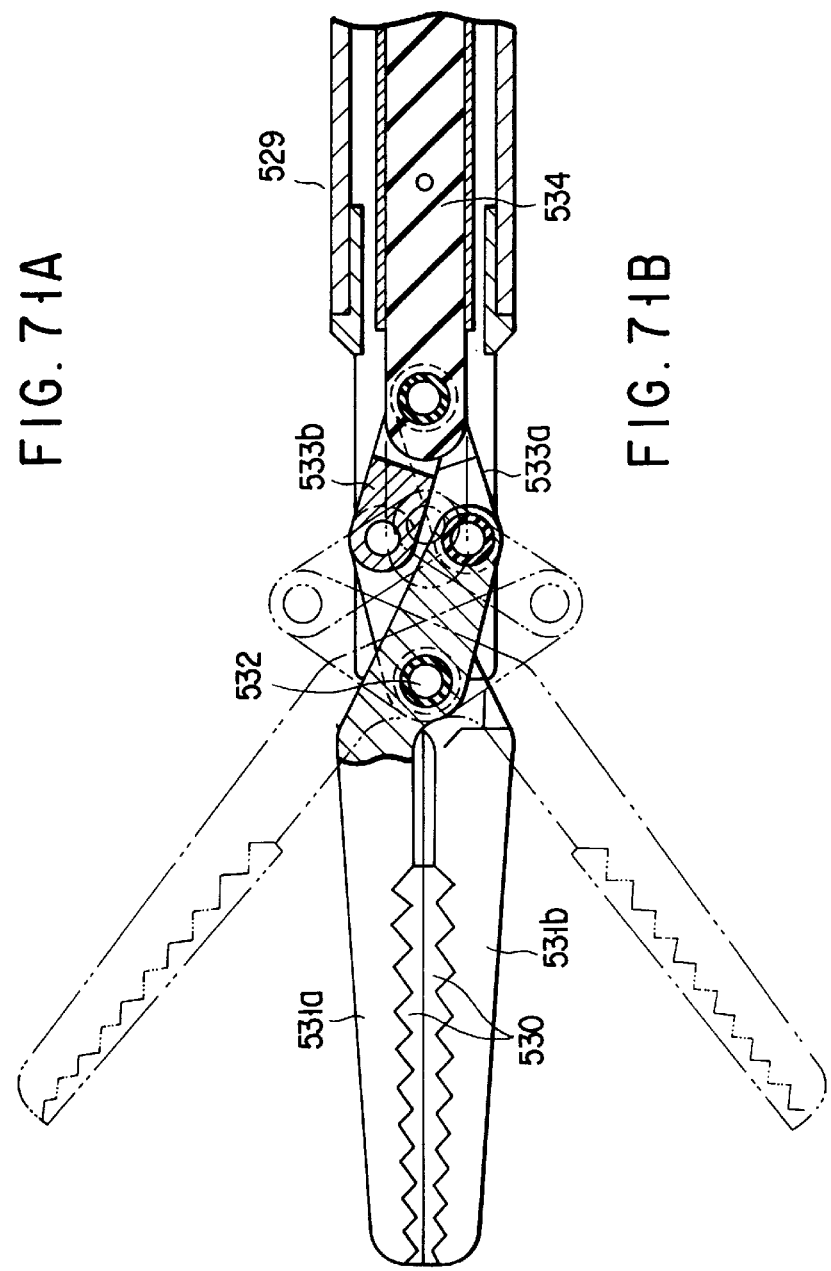
FIG. 71B is a sectional view taken along a line 71B—71B in FIG. 71A.

FIGS. 71A and 71B show the 33rd embodiment of the present invention. A high-frequency treatment tool of this embodiment has a treatment portion opened/closed by a driving portion using a link. Jaws 531a and 531b having incision projections 530 are attached to the distal end portion of an insertion portion 529. The jaws 531a and 531b are pivotally supported by a pivot shaft 532. The proximal end portions of the jaws 531a and 531b are coupled to an operation rod 534 inserted into the insertion portion 529 to freely move back and forth through links 533a and 533b.

When the operation rod 534 moves forward, the jaws 531a and 531b are opened upon pivoting about the pivot shaft 532. When the operation rod 534 moves backward, the jaws 531a and 531b are closed upon pivoting about the pivot shaft 532.

To peel vital tissue A, while the jaws 531a and 531b are closed, and the distal end portions of the jaws 531a and 531b are pressed against the portion of the vital tissue A to be peeled, the operation rod 534 is moved forward to open the jaws 531a and 531b upon pivoting about the pivot shaft 532. The operation rod 534 is moved backward again to close the jaws 531a and 531b upon pivoting about the pivot shaft 532. By repeatedly opening/closing the jaws 531a and 531b, the vital tissue A can be peeled.

In this embodiment as well, an electrical insulating portion may be formed on the gripping surface of at least one gripping portion (jaw 531a or 531b), as in the first to fifth embodiments. In this case, a predetermined gap is formed between the gripping surfaces of the gripping portions when the gripping portions are completely closed to make the electrical insulating portion abut against the gripping surface of the other gripping portion, thereby preventing a short circuit between the electrode portions of the gripping portions.

FIGS. 72A and 72B show the 34th embodiment of the present invention. A high-frequency treatment tool of this embodiment has a treatment portion opened/closed by a driving portion using a cam. Jaws 531a and 531b having incision projections 530 and opened/closed by a cam are attached to the distal end portion of an insertion portion 529. The jaws 531a and 531b are pivotally supported by a pivot shaft 532. Cam shafts 535a and 535b are provided at the proximal end portions of the jaws 531a and 531b. A cam plate 537 is attached to the distal end portion of an operation rod 536 inserted into the insertion portion 529 to freely move back and forth. Cam grooves 538a and 538b engaging with the cam shafts 535a and 535b, respectively, are formed in the cam plate 537.

When the operation rod 536 moves forward, the cam shafts 535a and 535b are guided by the cam grooves 538a and 538b, respectively, to press the cam shaft 535a downward and the cam shaft 535b upward, so the jaws 531a and 531b are opened upon pivoting about the pivot shaft 532. When the operation rod 536 moves backward, the jaws 531a and 531b are closed upon pivoting about the pivot shaft 532.

To peel vital tissue A, while the jaws 531a and 531b are closed, and the distal end portions of the jaws 531a and 531b are pressed against the portion of the vital tissue A to be peeled, the operation rod 536 is moved forward to open the jaws 531a and 531b upon pivoting about the pivot shaft 532. The operation rod 536 is moved backward again to close the jaws 531a and 531b upon pivoting about the pivot shaft 532. By repeatedly opening/closing the jaws 531a and 531b, the vital tissue A can be peeled.

FIGS. 73A to 73D show the 35th embodiment of the present invention. A high-frequency treatment tool of this embodiment is a ventromy forceps. A forceps main body 540 basically has the form of a scissors. A pair of forceps members 541a and 541b having the same shape are pivotally coupled to each other through a pivot shaft 542 at an almost middle portion. The pair of forceps members 541a and 541b have jaws 542a and 542b at their distal end portions. The jaws 542a and 542b have mesh portions which mesh with each other when the jaws 542a and 542b are closed, so vital tissue A can be reliably gripped. In addition, incision projection 543a and 543b as projecting portions integrated with the mesh portions of the jaws 542a and 542b, respectively, are formed at almost middle portions in the direction of width along the longitudinal direction.

Finger hook portions 544a and 544b are formed at the proximal end portions of the pair of forceps members 541a and 541b, respectively. Cables 545a and 545b connected to a high-frequency cautery power supply unit (not shown) are connected to the finger hook portions 544a and 544b, respectively.

Each of the pair of finger hook portions 544a and 544b and pivot shaft 542 is covered with an insulating member 546. Only the incision projection 543a and 543b formed on the jaws 542a and 542b as projecting portions, respectively, are exposed from the insulating members 546.

When the operators places the fingers on the finger hook portions 544a and 544b to perform the opening/closing operation, the jaws 542a and 542b can be opened/closed to grip vital tissue. When a coagulation current or incision current is flowed to the incision projections 543a and 543b of the jaws 542a and 542b, the vital tissue can be coagulated or incised.

In this embodiment as well, an electrical insulating portion may be formed on the gripping surface of at least one gripping portion (jaw 542a or 542b), as in the first to fifth embodiments. In this case, a predetermined gap is formed between the gripping surfaces of the gripping portions when the gripping portions are completely closed to make the electrical insulating portion abut against the gripping surface of the other gripping portion, thereby preventing a short circuit between the electrode portions of the gripping portions.

Figure 74A:
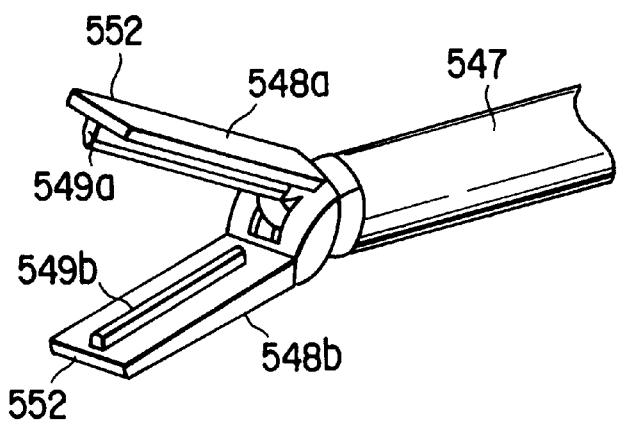
FIG. 74A is a perspective view of the treatment portion of a high-frequency treatment tool according to the 36th embodiment of the present invention.
Figure 74B:
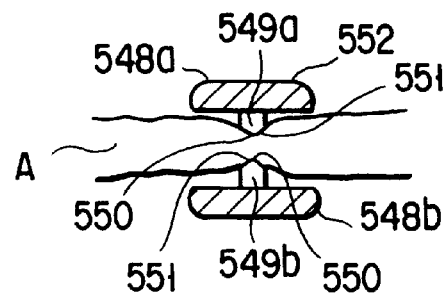
FIG. 74B is a sectional view showing a state wherein tissue is gripped by the treatment portion shown in FIG. 74A.

FIGS. 74A and 74B show the 36th embodiment of the present invention. In this embodiment, jaws 548a and 548b opened/closed by a cam are attached to the distal end portion of an insertion portion 547. Incision projections 549a and 549b as projecting portions integrated with the jaws 548a and 548b are formed on opposing surfaces of the jaws 548a and 548b, respectively, at almost middle portions in the direction of width along the longitudinal direction. Each of the incision projections 549a and 549b has a substantially V-shaped section and an acute-angled portion 550 at the distal end portion and oblique surfaces 551 on both sides of the distal end portion.

The entire surfaces of the jaws 548a and 548b except the incision projections 549a and 549b are covered with insulating layers 552. The insulating layer 552 may be formed by Teflon coating, insulating coating, or insulating tubes. Alternatively, the jaws 548a and 548b themselves may be formed from an insulating ceramic or synthetic resin.

According to this embodiment, when the jaws 548a and 548b are closed, the incision projections 549a and 549b move close to each other to grip vital tissue A. When a coagulation current is flowed to the jaws 548a and 548b, the vital tissue A can be coagulated. In addition, when an incision current is flowed, the vital tissue A can be incised. Since the entire surfaces of the incision projections 549a and 549b are covered with the insulating layers 552, the incision current is concentrated to the incision projections 549a and 549b, and incision can be easily performed.

Figure 75:
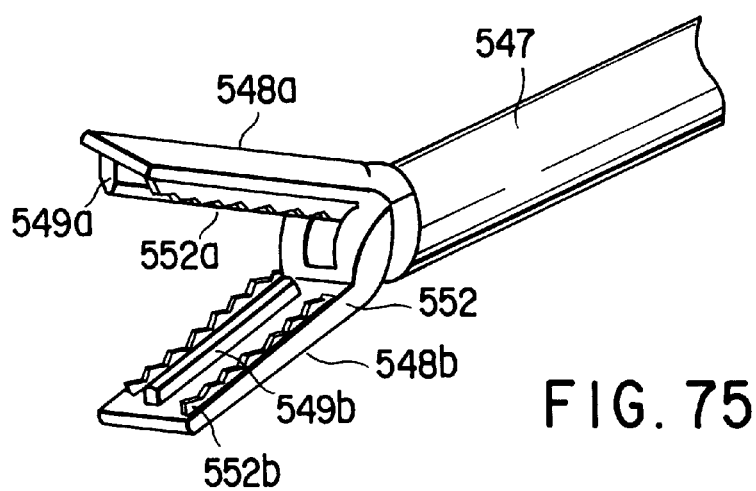
FIG. 75 is a perspective view of the treatment portion of a high-frequency treatment tool according to the 37th embodiment of the present invention.

FIG. 75 shows the 37th embodiment of the present invention. In this embodiment, on the opposing surfaces of jaws 548a and 548b of the 36th embodiment, insulating gripping portions 552a and 552b having uneven portions are formed at the two edge portions in the direction of width along incision projections 549a and 549b, respectively. According to this embodiment, vital tissue A gripped by the insulating gripping portions 552a and 552b having uneven portions can be prevented from slipping, and the target portion can be reliably gripped.

Figure 76:
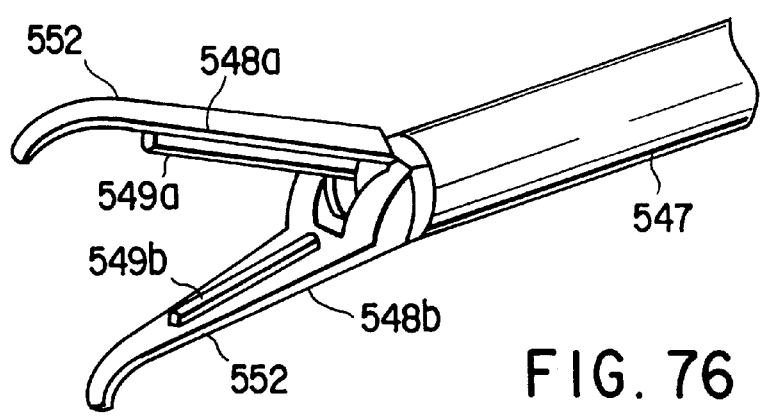
FIG. 76 is a perspective view of the treatment portion of a high-frequency treatment tool according to the 38th embodiment of the present invention.

FIG. 76 shows the 38th embodiment of the present invention. In this embodiment, jaws 548a and 548b of the 36th embodiment are gradually tapered toward the distal end portions, and the distal end portions of the jaws 548a and 548b are bent in one direction to form a Kelly clamp. According to this embodiment, since the distal end portions of the jaws 548a and 548b are bent, the operability in peeling vital tissue A is improved. Incision projections 549a and 549b may be formed to the bent portions of the distal end portions of the jaws 548a and 548b.

Figure 77:
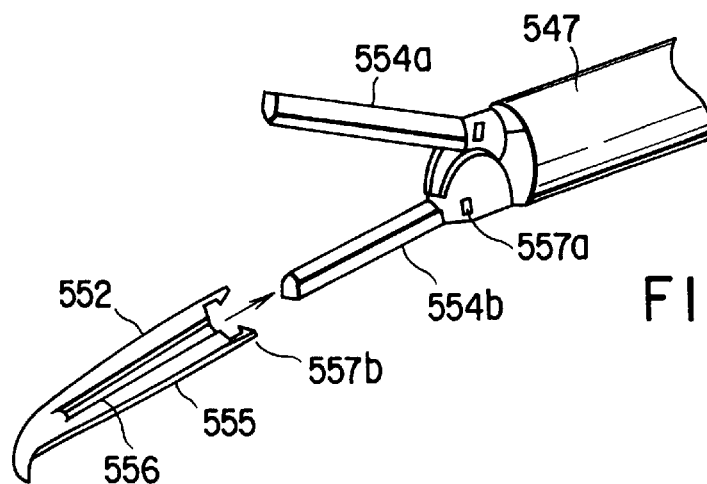
FIG. 77 is a perspective view of the treatment portion of a high-frequency treatment tool according to the 39th embodiment of the present invention.

FIG. 77 shows the 39th embodiment of the present invention. In this embodiment, each of jaws 554a and 554b is divided into a conductive incision projection 554 and an insulating gripping portion 555, and the insulating gripping portion 555 is detachably attached to the conductive incision projection 554. The incision projection 554 has a rod shape. The gripping portion 555 has an engaging groove 556 engaging with the incision projection 554. An engaging hole 557a is formed at the proximal end portion of the incision projection 554. An engaging portion 557b engaging with the engaging hole 557a is formed at the proximal end portion of the gripping portion 555.

According to this embodiment, when a plurality of types of gripping portions 555 with different shapes and sizes are prepared, the shapes and sizes of the jaws 554a and 554b can be changed. In addition, damaged jaws can also be easily exchanged. Furthermore, since the gripping portion 555 is curved, the operability in peeling vital tissue A is improved.

FIGS. 78A to 78C show the 40th embodiment of the present invention. In this embodiment, curved surface portions 558 are formed at the front end portions of incision projections 549a and 549b of jaws 548a and 548b of the 37th embodiment. When the curved surface portions 558 are formed, the incision projections 549a and 549b at the curved surface portions 558 do not come into contact with each other during coagulation/incision of vital tissue A. For this reason, the vital tissue A is only coagulated and not incised. A region 559a where coagulation/incision is performed at the basic portions of the incision projections 549a and 549b can be discriminated from a region 559b where only coagulation is performed at the curved surface portions 558, so bleeding from the incised end portion can be prevented.

FIGS. 79A to 81B show the 41st embodiment of the present invention. The same reference numerals as in the 26th embodiment denote the same parts in the 41st embodiment, and a detailed description thereof will be omitted.

FIG. 79A is a view showing the overall arrangement of a high-frequency treatment tool as an endoscopic operation tool. As shown in FIG. 79A, a bipolar forceps 501 as a high-frequency treatment tool comprises a long insertion portion 502 to be inserted into the body cavity of a patient, a treatment portion 503 attached to the distal end portion of the insertion portion 502 to grip vital tissue and coagulate or incise it in the body cavity, to which power can be supplied, and an operation portion 504 coupled to the proximal end portion of the insertion portion 502.

The insertion portion 502 has a rotatable outer sheath 505. An inner sheath 507 of the outer sheath 505 is inserted in a grip 506 constituting the operation portion 504. The treatment portion 503 has a long rod (not shown) inserted in the outer sheath 505. At the distal end portion of the rod, a pair of jaws 560a and 560b as electrodes constituting the treatment portion 503 are fixed to elastic members 509a and 509b for biasing the jaws 560a and 560b in the opening direction. The elastic members 509a and 509b are formed from spring steel or the like and covered with insulating tubes 561a and 561b, respectively.

Figure 80B:
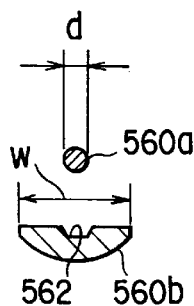
Figure 80A:
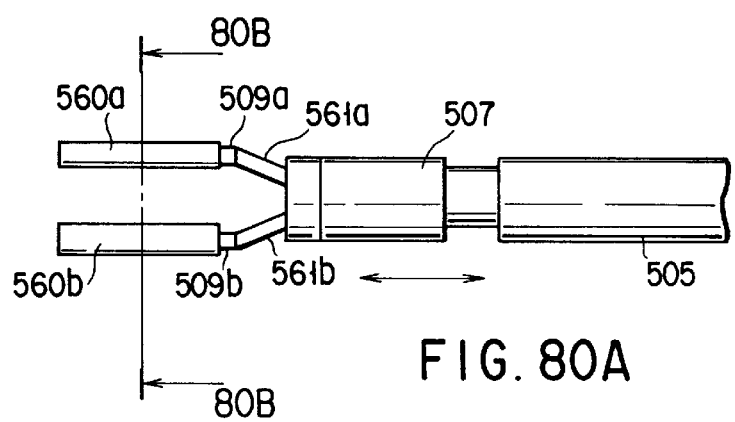

As shown in FIGS. 80A and 80B, of the pair of jaws 560a and 560b, the upper jaw 560a is a wire-shaped electrode having a diameter d of 0.5 to 2.5 mm and, more preferably, 1 to 2 mm and capable of simultaneously coagulating and incising vital tissue A. The lower jaw 560b has a flat plate shape. A width w of the tissue gripping surface is about 5 mm, and a recessed groove 562 in which the upper jaw 560a can fit is formed at almost the central portion of the tissue gripping surface.

A conductive member (not shown) connected to the jaws 560a and 560b of the treatment portion 503 is connected to a connector receptacle 513 of the operation portion 504 through the outer sheath 505 constituting the insertion portion 502. The connector receptacle 513 is connected to a high-frequency cautery power supply unit 515 through a cable 514. The high-frequency cautery power supply unit 515 has a foot switch 516.

The grip 506 has a trigger 517 as a forceps operation means. The trigger 517 is coupled to the upper end portion of the grip 506 to freely pivot about a pivot pin 518. The upper end portion of the pivot fulcrum of the trigger 517 is coupled to the proximal end portion of the inner sheath 507.

The grip 506 has a finger hook portion 506a on which the operator places the thumb. The trigger 517 has finger hook portions 517a and 517b on which the operator places the index and middle fingers, respectively. When the trigger 517 is opened in a direction indicated by an arrow a, the inner sheath 507 moves backward to open the jaws 560a and 560b. When the trigger 517 is closed in a direction indicated by an arrow b, the inner sheath 507 moves forward to close the jaws 560a and 560b.

The function of the 41st embodiment will be described next.

The cable 514 is connected to the connector receptacle 513 of the bipolar forceps 501 to electrically connect the bipolar forceps 501 to the high-frequency cautery power supply unit 515. In the initial state, the trigger 517 of the operation portion 504 is pivoted to the direction indicated by the arrow a. In this state, the pair of elastic members 509a and 509b of the treatment portion 503 project from the inner sheath 507 to open the jaws 560a and 560b, as shown in FIG. 79B.

When the finger hook portions 517a and 517b of the trigger 517 are pulled to the grip 506 side against the spring force of the biasing members in the grip 506, the inner sheath 507 moves forward in the axial direction. As the inner sheath 507 moves forward, the elastic members 509a and 509b are relatively retracted into the inner sheath 507 to close the jaws 560a and 560b, as shown in FIG. 79A.

In this state, the insertion portion 502 of the bipolar forceps 501 is inserted into the body of a patient, and the treatment portion 503 at the distal end of the insertion portion 502 is placed near the vital tissue A to be treated in the body. When the trigger 517 is released, the trigger 517 returns to the home position by the spring force of the biasing member in the grip 506. The elastic members 509a and 509b relatively project from the inner sheath 507, and the jaws 560a and 560b are opened by the elastic restoring force of the elastic members 509a and 509b.

Figure 81A:
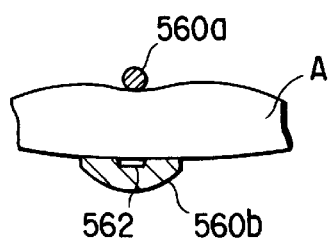

After the vital tissue A is inserted between the opened jaws 560a and 560b, the finger hook portions 517a and 517b of the trigger 517 are pulled to the grip 506 side to move the inner sheath 507 forward in the axial direction. As the inner sheath 507 moves forward, the elastic members 509a and 509b are relatively retracted into the inner sheath 507 to close the jaws 560a and 560b. The vital tissue A is gripped between the pair of jaws 560a and 560b, as shown in FIG. 81A.

In this state, a high-frequency current is flowed from the high-frequency cautery power supply unit 515 to the connector receptacle 513 through the cable 514. A coagulation current is flowed across the jaws 560a and 560b to coagulate the vital tissue A.

Figure 81B:
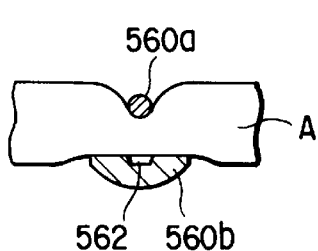

Subsequently, when the finger hook portions 517a and 517b of the trigger 517 are further pulled to the grip 506 side, the jaws 560a and 560b are further closed, and an incision current is flowed across the jaws 560a and 560b, and the vital tissue A is incised by the pair of jaws 560a and 560b, as shown in FIG. 81B.

When coagulation and incision are complete, the trigger 517 is pivoted in the direction indicated by the arrow a. The inner sheath 507 moves backward, and the elastic members 509a and 509b are opened by the elastic restoring force. The jaws 560a and 560b are released from the vital tissue A.

In this case, the incision current may be flowed upon determining that the vital tissue is completely coagulated on the basis of a change in impedance. More specifically, the coagulation current generally has load characteristics representing that when the impedance increases upon cautery, the output decreases, as shown in FIG. 82A. However, the incision current has a constant power output mode in which even when the impedance increases, the output does not decrease, as shown in FIG. 82B. As shown in FIG. 82C, in impedance control, when the generator determines that coagulation is complete at a point a when the impedance which has temporarily decreased increases again as the cautery time elapses, i.e., after coagulation is reliably performed, the incision current is flowed to incise the vital tissue A. That is, the coagulation current and the incision current can be automatically switched.

According to the findings in experiments conducted by the present inventors, for a bipolar structure, as in this embodiment, when the ratio of the projected areas of the jaws 560a and 560b (ratio of areas of portions in contact with the gripped tissue) is 1:10 to 1:2 (the upper jaw 560a has a diameter d of 0.5 to 2.5 mm, and the lower jaw 560b has a width w of 5 mm), the tissue can be satisfactorily coagulated/incised (when the tissue is gripped and coagulated by setting the coagulation output of a high-frequency oscillator at 30 W, and then, incised by setting the incision output at 30 W). On the other hand, when one of the jaws of a tripolar structure has an insulating portion, the tissue can be satisfactorily coagulated/incised under the following conditions (when the tissue is gripped and coagulated by setting the coagulation output of a high-frequency oscillator at 30 W, and then, incised by setting the incision output at 30 W). As shown in FIGS. 84A and 84B, in a tripolar structure in which a first jaw 600 has first and second coagulation electrodes 605 and 606 electrically insulated from each other by an insulating portion 604, and a second jaw 601 has, e.g., an incision wire electrode 603 (in this example, when the jaws 600 and 601 are completely closed, the incision electrode 603 abuts against the insulating portion 604 to prevent a short circuit between the electrodes) fixed on a support rod 602, when the ratio of the projected areas of the electrode portions 603, 605, and 606 of the jaws 600 and 601 (ratio of areas of portions in contact with the gripped tissue) is 1:10 to 1:2, the tissue can be satisfactorily coagulated/incised. More specifically, let a be the diameter of the incision electrode 603, c be the width of the insulating portion 604, and b be the width of the first jaw 600. When a:(b−c)=1:10 to 1:2, the tissue can be satisfactorily coagulated/incised.

In the 41st embodiment shown in FIGS. 81A and 81B, the tissue is coagulated and incised by performing the gripping operation once. However, the tissue may be coagulated and incised by performing the gripping operation twice, as shown in FIGS. 83A to 83C. More specifically, the jaws 560a and 560b are closed by pulling the finger hook portions 517a and 517b of the trigger 517 to the grip 506 side. In this state, the insertion portion 502 of the bipolar forceps 501 is inserted into the body of a patient, and the treatment portion 503 at the distal end of the insertion portion 502 is guided near the vital tissue A to be treated in the body. When the trigger 517 is released, the trigger 517 returns to the home position by the spring force of the biasing member in the grip 506. The elastic members 509a and 509b relatively project from the inner sheath 507, and the jaws 560a and 560b are opened by the elastic restoring force of the elastic members 509a and 509b.

After the vital tissue A is inserted between the opened jaws 560a and 560b, the finger hook portions 517a and 517b of the trigger 517 are pulled to the grip 506 side to move the inner sheath 507 forward in the axial direction. As the inner sheath 507 moves forward, the elastic members 509a and 509b are relatively retracted into the inner sheath 507 to close the jaws 560*a* and 560*b*. The vital tissue A is gripped between the pair of jaws 560*a* and 560*b*, as shown in FIG. 83A.

In this state, a high-frequency current flows from the high-frequency cautery power supply unit 515 to the connector receptacle 513 through the cable 514. A coagulation current flows across the jaws 560*a* and 560*b* to coagulate the vital tissue A. In this case, a small gripping force is applied to the trigger 517 in accordance with a change in vital tissue A upon coagulation.

Subsequently, when the trigger 517 is released, the trigger 517 returns to the home position by the spring force of the biasing member in the grip 506. The elastic members 509*a* and 509*b* relatively project from the inner sheath 507, and the jaws 560*a* and 560*b* are opened by the elastic restoring force of the elastic members 509*a* and 509*b*. The jaws 560*a* and 560*b* are temporarily opened and separated from the vital tissue A, as shown in FIG. 83B.

The finger hook portions 517*a* and 517*b* of the trigger 517 are further pulled to the grip 506 side to close the jaws 560*a* and 560*b* until they come into contact with each other. At the same time, an incision current is flowed across the jaws 560*a* and 560*b*. The vital tissue A is incised by the pair of jaws 560*a* and 560*b*, as shown in FIG. 83C.

Upon completing coagulation and incision, the trigger 517 is pivoted in the direction indicated by the arrow a, the inner sheath 507 moves backward, and the elastic members 509*a* and 509*b* are opened by the elastic restoring force, so the jaws 560*a* and 560*b* are released from the vital tissue A.

FIGS. 85A to 86D show the 42nd embodiment of the present invention. The same reference numerals as in the 41st embodiment denote the same parts in the 42nd embodiment, and a detailed description thereof will be omitted. In this embodiment, of a pair of jaws 563*a* and 563*b* of a treatment portion 503, the upper jaw 563*a* is formed as a wire electrode having a triangular section. The lower jaw 563*b* has a flat shape. A recessed groove 564 opposing the jaw 563*a* is formed on the gripping surface, and serrate portions 565 are formed on both sides of the recessed groove 564. The arrangement of the remaining portions is the same as in the 41st embodiment. In this embodiment, since the upper jaw 563*a* has a sharp edge portion, the ability of incising vital tissue A is excellent, and the operation force for a trigger 517 can be reduced.

FIGS. 87A and 87B show the 43rd embodiment of the present invention. The same reference numerals as in the 41st embodiment denote the same parts in the 43rd embodiment, and a detailed description thereof will be omitted. In this embodiment, of a pair of jaws 566*a* and 566*b* of a treatment portion 503, the upper jaw 566*a* is formed into a knife shape having a triangular section to form a sharp portion 567 and has a hollow portion 568 at the central portion. The lower jaw 566*b* has a flat shape, and a serrate portion 565 is formed on the gripping surface. The arrangement of the remaining portions is the same as in the 41st embodiment. In this embodiment, since the upper jaw 566*a* has the sharp portion 567, the ability of incising vital tissue A is excellent, and the operation force for a trigger 517 can be reduced.

FIGS. 88A and 88B show the 44th embodiment of the present invention. The same reference numerals as in the 41st embodiment denote the same parts in the 44th embodiment, and a detailed description thereof will be omitted. In this embodiment, of a pair of jaws 569*a* and 569*b* of a treatment portion 503, the upper jaw 569*a* is formed as an electrode having a prism-shaped section and a sharp portion 570 on one side. The lower jaw 569*b* has a flat shape, and a recessed groove 571 is formed in the gripping surface opposing the jaw 569*a*. The arrangement of the remaining portions is the same as in the 41st embodiment. In this embodiment, since the upper jaw 569*a* has the sharp portion 570, the ability of incising vital tissue A is excellent, and the operation force for a trigger 517 can be reduced.

For the pairs of jaws in the 42nd to 44th embodiments, each of the upper jaw 563*a*, 566*a*, and 569*b* is formed as an electrode having a width of 1 to 2 mm to incise the vital tissue A simultaneously with coagulation, and each of the lower jaw 563*b*, 566*b*, and 569*b* having a flat shape has a tissue gripping surface width of about 5 mm and a ratio of 1:10 to 1:2, as in the 41st embodiment.

FIGS. 89A to 90C show the 45th embodiment of the present invention. The same reference numerals as in the 26th embodiment denote the same parts in the 45th embodiment, and a detailed description thereof will be omitted.

FIGS. 89A and 89B are views showing the overall arrangement of a high-frequency treatment tool as an endoscopic operation tool. As shown in FIGS. 89A and 89B, a bipolar forceps 501 as a high-frequency treatment tool comprises a long insertion portion 502 to be inserted into the body cavity of a patient, a treatment portion 503 attached to the distal end portion of the insertion portion 502 to grip vital tissue and coagulate or incise it in the body cavity, to which power can be supplied, and an operation portion 504 coupled to the proximal end portion of the insertion portion 502.

The insertion portion 502 has a rotatable outer sheath 505. A tip cover 580 is attached to the distal end portion of the outer sheath 505, as shown in FIG. 90A. The tip cover 580 has a pin 581 for attaching the treatment portion 503. An operation rod 582 with its proximal end portion being inserted to a grip 506 of the operation portion 504 and its distal end portion being coupled to the treatment portion 503 is inserted into the outer sheath 505.

The operation rod 582 comprises two electrodes 583*a* and 583*b* having substantially semicircular sections and electrically insulated from each other, an insulating member 584 having a substantially rectangular section, and an insulating tube 585 covering these members. The electrodes 583*a* and 583*b* are coupled through a pin 589. The distal end portions of the electrodes 583*a* and 583*b* are coupled to links 586*a* and 586*b* through a pin 590. The links 586*a* and 586*b* are coupled to a pair of jaws 508*a* and 508*b* pivotally supported by the pin 581, respectively.

The pins 581, 589, and 590 are insulated by insulating members 581*a*, 589*a*, and 590*a*. A connector receptacle 513 is connected to a high-frequency cautery power supply unit 515 through a cable 514. The high-frequency cautery power supply unit 515 has a foot switch 516.

A fixed grip 587 of the operation portion 504 has a movable grip 588. The movable grip 588 is coupled to the upper end portion of the fixed grip 587 to pivot about a pivot pin 591. The upper end portion of the pivot fulcrum of the movable grip 588 is coupled to the proximal end portion of the operation rod 582. The movable grip 588 has a finger hook portion 588*a* on which the operator places the thumb. The fixed grip 587 has finger hook portions 587*a* and 587*b* on which the operator places the index and middle fingers, respectively. When the movable grip 588 is closed in a direction indicated by an arrow a, the operation rod 582 moves backward to close the jaws 508*a* and 508*b* through the links 586*a* and 586*b*. When the movable grip 588 is opened in a direction in indicated by an arrow b, the operation rod 582 moves forward to open the jaws 508*a* and 508*b*.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A high-frequency treatment tool comprising:

an insertion portion for insertion into a body;

a pair of gripping portions arranged at a distal end portion of said insertion portion and having gripping surfaces for gripping vital tissue;

a driving mechanism for opening/closing said pair of gripping portions between a closing position where said pair of gripping portions abut against each other and an open position where said pair of gripping portions are separated from each other;

electrode portions formed on the gripping surfaces of said gripping portions, to which a high-frequency current is flowed to coagulate/incise the vital tissue gripped by said gripping portions; and short circuit prevention means for preventing a short circuit between said electrode portions of said pair of gripping portions when said pair of gripping portions are placed at least at the closing positions, said short circuit prevention means being a solid insulating member coupled to at least one of said pair of gripping portions, said solid insulating member having a thickness at at least one point which is equal to a thickness of the at least one of said pair of gripping portions so to preclude electrical contact between said pair of gripping portions.

2. A high-frequency treatment tool according to claim 1, wherein when said pair of gripping portions are in the closing position said gripping surfaces of said pair of gripping portions are separated from each other by a predetermined gap.

3. A high-frequency treatment tool according to claim 1, wherein said short circuit prevention means is formed at a distal end portion of said one of said pair of gripping portions.

4. A high-frequency treatment tool according to claim 3, wherein said short circuit prevention means is formed by forming the distal end portion of said one of said pair of gripping portions from a material having electrical insulating properties.

5. A high-frequency treatment tool according to claim 4, wherein the distal end portion of said one of said pair of gripping portions is ceramic.

6. A high-frequency treatment tool according to claim 3, wherein said short circuit prevention means further comprises forming an insulating coating on at least a gripping surface at the distal end portion of said one of said pair of gripping portions.

7. The high-frequency treatment tool according to claim 1 wherein said short circuit prevention means is disposed at a distal end portion of said pair of gripping portions.

8. The high-frequency treatment tool according to claim 1 wherein said short circuit prevention means includes serrated surfaces.

9. A high-frequency treatment tool comprising:

an insertion portion which can be inserted into a body;

a pair of gripping portions arranged at a distal end portion of said insertion portion and having gripping surfaces for gripping vital tissue;

a driving mechanism for opening/closing said gripping portions between closing positions where said gripping portions abut against each other and open positions where said gripping portions are separated from each other;

electrode portions formed on the gripping surfaces of said gripping portions, to which a high-frequency current is flowed to coagulate/incise the vital tissue gripped by said gripping portions; and a short circuit preventor which prevents a short circuit between said electrode portions of said pair of gripping portions when said pair of gripping portions are placed at least at the closing positions, said short circuit preventor forming an entire distal end of at least one of said pair of gripping portions.

10. The high-frequency treatment tool according to claim 9 wherein said short circuit preventor includes serrated surfaces.

* * * * *